(12) United States Patent
Jagtiani

(10) Patent No.: US 11,400,452 B2
(45) Date of Patent: Aug. 2, 2022

(54) DEVICES, CARTRIDGES, AND SENSORS FOR ANALYZING A BIOLOGICAL SAMPLE

(71) Applicant: Chronus Health, Inc., Mountain View, CA (US)

(72) Inventor: Ashish Jagtiani, San Francisco, CA (US)

(73) Assignee: CHRONUS HEALTH, INC., Mountain View, CA (US)

( * ) Notice: Subject to any disclaimer, the term of this patent is extended or adjusted under 35 U.S.C. 154(b) by 0 days.

(21) Appl. No.: 17/677,711

(22) Filed: Feb. 22, 2022

(65) Prior Publication Data

US 2022/0176378 A1 Jun. 9, 2022

Related U.S. Application Data

(63) Continuation of application No. 15/734,916, filed as application No. PCT/US2019/035548 on Jun. 5, 2019.

(Continued)

(51) Int. Cl.
*B01L 3/00* (2006.01)
*G01N 27/08* (2006.01)
(Continued)

(52) U.S. Cl.
CPC .... *B01L 3/502792* (2013.01); *G01N 15/0656* (2013.01); *G01N 27/08* (2013.01);
(Continued)

(58) Field of Classification Search
CPC ....... B01L 3/502792; B01L 2300/0636; B01L 2300/0645; B01L 2400/027; G01N 27/08; G01N 33/48707

See application file for complete search history.

(56) References Cited

U.S. PATENT DOCUMENTS 2,656,508 A 10/1953 Coulter
6,089,078 A 7/2000 Chelveder et al.
(Continued)

FOREIGN PATENT DOCUMENTS

EP 2182345 B1 6/2013
WO 2008131609 A1 11/2008
(Continued)

OTHER PUBLICATIONS

Barat, D. et al. (2012). "Simultaneous High Speed Optical and Impedance Analysis of Single Particles With a Microfluidic Cytometer," Lab on a Chip 12(1):118-126.
(Continued)

*Primary Examiner* — Christopher Adam Hixson
(74) *Attorney, Agent, or Firm* — Morrison & Foerster LLP

(57) ABSTRACT

Described herein are cartridges and devices for operating said cartridges for analyzing a biological sample, such as a blood or saliva sample. Also described herein is an impedance sensor for analyzing a biological sample. Further described herein are methods of determining a cell count or detecting an analyte in a biological sample, which can include transporting the biological sample through a sensor comprising a channel or pore; applying an electrical current or voltage to the channel or pore; detecting an impedance within the channel or pore; and determining a cell count or detecting the analyte based on the detected impedance. Also described herein is an electrowetting electrode array that is configured to transport aqueous solutions using low voltage, such as about 50 volts or less. Further described herein are methods of transporting an aqueous liquid using electrowetting electrodes.

30 Claims, 27 Drawing Sheets

Related U.S. Application Data

(60) Provisional application No. 62/756,007, filed on Nov. 5, 2018, provisional application No. 62/756,011, filed on Nov. 5, 2018, provisional application No. 62/680,993, filed on Jun. 5, 2018, provisional application No. 62/680,989, filed on Jun. 5, 2018, provisional application No. 62/680,992, filed on Jun. 5, 2018.

(51) Int. Cl.
 *G01N 33/487* (2006.01)
 *G01N 15/06* (2006.01)
(52) U.S. Cl.
 CPC ............... *G01N 33/48707* (2013.01); *B01L 2300/0636* (2013.01); *B01L 2300/0645* (2013.01); *B01L 2400/0427* (2013.01)

(56) References Cited

U.S. PATENT DOCUMENTS

| | | | |
|---|---|---|---|
| 6,169,394 | B1 | 1/2001 | Frazier et al. |
| 6,437,551 | B1 | 8/2002 | Krulevitch et al. |
| 6,911,132 | B2 | 6/2005 | Pamula et al. |
| 7,329,545 | B2 | 2/2008 | Pamula et al. |
| 7,777,476 | B2 | 8/2010 | Hu et al. |
| 8,329,437 | B1 | 12/2012 | Ayliffe |
| 8,642,287 | B2 | 2/2014 | Wang et al. |
| 8,852,875 | B2 | 10/2014 | Toner et al. |
| 9,863,962 | B1 | 1/2018 | Eissa et al. |
| 10,267,720 | B2 | 4/2019 | Spencer et al. |
| 10,359,351 | B2 | 7/2019 | Spencer et al. |
| 2003/0072549 | A1 | 4/2003 | Facer et al. |
| 2003/0085719 | A1 | 5/2003 | Yoon et al. |
| 2007/0238112 | A1 | 10/2007 | Sohn et al. |
| 2010/0143905 | A1 | 6/2010 | Lane et al. |
| 2011/0275111 | A1 | 11/2011 | Pettigrew et al. |
| 2012/0064567 | A1* | 3/2012 | Stakenborg ........ G01N 15/1245 435/306.1 |
| 2012/0142032 | A1 | 6/2012 | Morgan et al. |
| 2012/0310541 | A1 | 12/2012 | Katz et al. |
| 2014/0190830 | A1 | 7/2014 | Sturmer et al. |
| 2016/0045144 | A1 | 2/2016 | Bansal et al. |
| 2020/0124519 | A1 | 4/2020 | Javanmard et al. |
| 2020/0333235 | A1 | 10/2020 | Javanmard et al. |
| 2021/0229102 | A1 | 7/2021 | Jagtiani |

FOREIGN PATENT DOCUMENTS

| | | |
|---|---|---|
| WO | 2013131411 A1 | 9/2013 |
| WO | 2014170625 A1 | 10/2014 |
| WO | 2016109569 A1 | 7/2016 |
| WO | 2017123742 A1 | 7/2017 |
| WO | 2020058681 A1 | 3/2020 |

OTHER PUBLICATIONS

Chang, J.-H. et al. (Nov. 4, 2009). "Driving Characteristics of the Electrowetting-on-Dielectric Device Using Atomic-Layer-Deposited Aluminum Oxide as the Dielectric," Microfluidics Nanofluidics 8:269-273.

Cho, S.K.. et al. (Feb. 2003). "Creating, Transporting, Cutting, and Merging Liquid Droplets by Electrowetting-Based Actuation for Digital Microfluidic Circuits," Journal of Microelectromechanical Systems 12(1):70-80.

Extended European Search Report, dated Feb. 8, 2022, for European Patent Application No. 19815885.9, 12 pages.

Gawad, S. et al. (2007, e-pub. May 29, 2007). "Impedance Spectroscopy Using Maximum Length Sequences: Application to Single Cell Analysis," Review of Scientific Instruments 78(54301):1-8.

Hadwen, B. et al. (2012). "Programmable Large Area Digital Microfluidic Array With Integrated Droplet Sensing for Bioassays," Lab on a Chip 12(18):3305-3313.

Hassan, U. et al. (Dec. 2015). "A Microfluidic Biochip for Complete Blood Cell Counts at the Point-of-Care," Technology (Singap World Sci) 3(4):201-213, 25 pages.

Hoffman, R.A. et al. (May 1981). "Flow Cytometric Electronic Direct Current Volume and Radiofrequency Impedance Measurements of Single Cells and Particles," Cytometry 1(6):377-384.

Holmes, D. et al. (2009, e-pub. Aug. 7, 2009). "Leukocyte Analysis and Differentiation Using High Speed Microfluidic Single Cell Impedance Cytometry," Lab Chip 9(20):2881-2889.

Holmes, D. et al. (2010). "Single Cell Impedance Cytometry for Identification and Counting of CD4 T-Cells in Human Blood Using Impedance Labels," Analytical Chemistry 82:1455-1461.

International Preliminary Report on Patentability, dated Dec. 8, 2020, for PCT Application No. PCT/US2019/035548, filed Jun. 5, 2019, 10 pages.

International Search Report and Written Opinion, dated Sep. 23, 2019, for PCT Application No. PCT/US2019/035548, filed Jun. 5, 2019, 14 pages.

Jagtiani, A.V. et al. (Apr. 21, 2011). "A Microfluidic Multichannel Resistive Pulse Sensor Using Frequency Division Multiplexing for High Throughput Counting of Micro Particles," Journal of Microelectromechanics and Microengineering 21:065004, 10 pages.

Jagtiani, A.V. et al. (Mar. 24, 2011). "An Impedimetric Approach for Accurate Particle Sizing Using a Micro Coulter Counter," Journal of Microelectromechanics and Microengineering 21:045036, 10 page.

Koch, M. et al. (1999). "Design and Fabrication of a Micromachined Coulter Counter," Journal of Micromechanics and Microengineering 9(2):159-161.

Malleo, D. et al. (2010, e-pub. Dec. 10, 2009). "Continuous Differential Impedance Spectroscopy of Single Cells," Microfluidics and Nanofluidics 9(2-3):191-198.

Moon, H. et al. (Oct. 1, 2002). "Low Voltage Electrowetting-on-Dielectric," Journal of Applied Physics 92(7):4080-4807.

Sun, T. et al. (2007). "High Speed Multi-Frequency Impedance Analysis of Single Particles in a Microfluidic Cytometer Using Maximum Length Sequences," Lab on a Chip 7(8):1034-1040.

Sun, T. et al. (2007, e-pub. Dec. 15, 2006). "Dielectric Spectroscopy of Single Cells: Time Domain Analysis Using Maxwell's Mixture Equation," Journal of Physics D: Applied Physics 40:1-8.

Sun, T. et al. (2010, e-pub. Oct. 21, 2009). "Single-Colloidal Particle Impedance Spectroscopy: Complete Equivalent Circuit Analysis of Polyelectrolyte Microcapsules," Langmuir 26(6):3821-3828.

Sun, T. et al. (Jun. 14, 2008). "Digital Signal Processing Methods for Impedance Microfluidic Cytometry," Microfluidics and Nanofluidics 6:179-187.

Sun, T. et al. (Mar. 6, 2008). "Analytical and Numerical Modeling Methods for Impedance Analysis of Single Cells On-Chip," Nano 3(1):55-63.

Sun, T. et al. (Oct. 2007). "Analytical Electric Field and Sensitivity Analysis for Two Microfluidic Impedance Cytometer Designs," IET Nanobiotechnology 1(5):69-79.

U.S. Appl. No. 62/748,362, Javanmard et al., filed Oct. 19, 3018. (Copy not submitted herewith pursuant to the waiver of 37 C.F.R. § 1 98(a)(2)(iii) issued by the Office on Sep. 21, 2004.).

U.S. Appl. No. 62/836,838, Javanmard et al., filed Apr. 22, 2019. (Copy not submitted herewith pursuant to the waiver of 37 C.F.R. § 1 98(a)(2)(iii) issued by the Office on Sep. 21, 2004.).

* cited by examiner

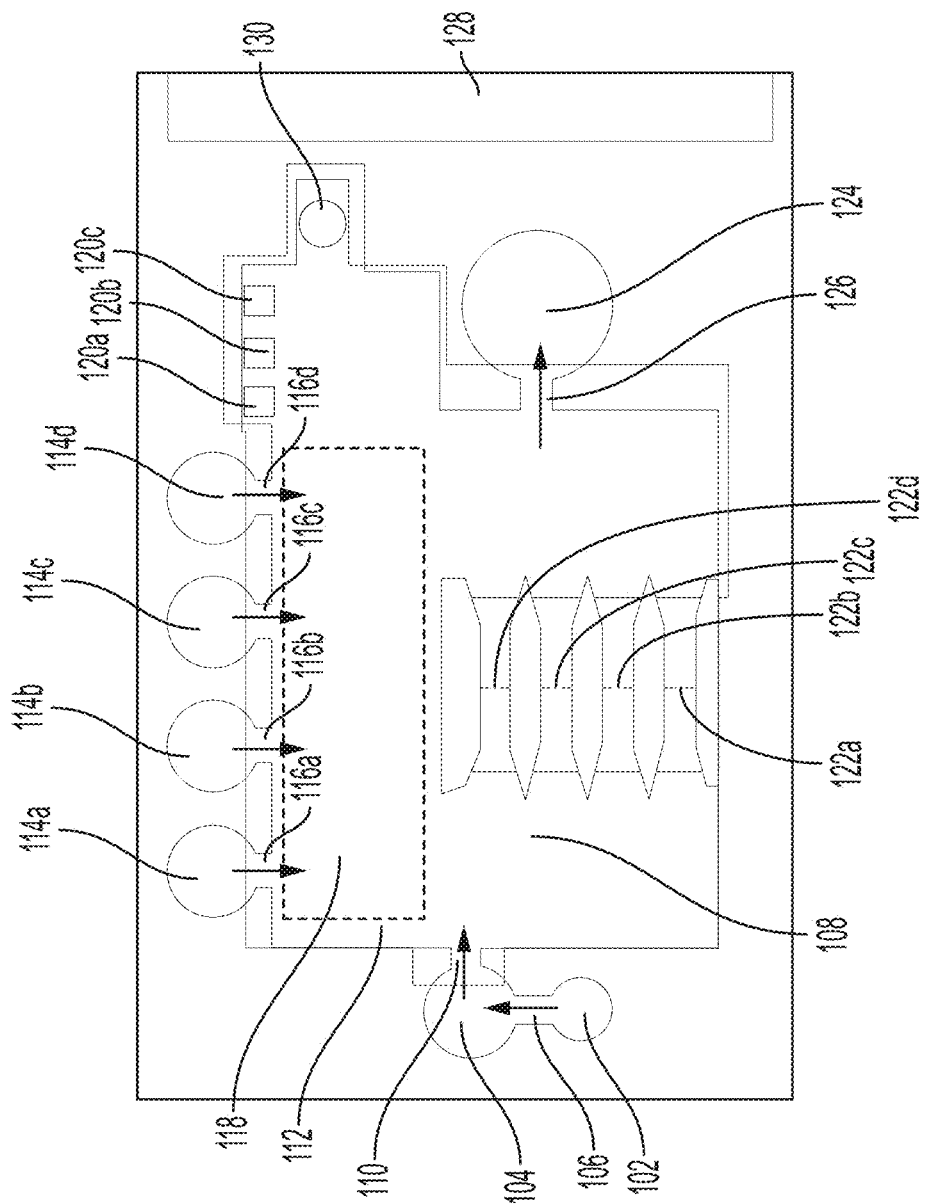

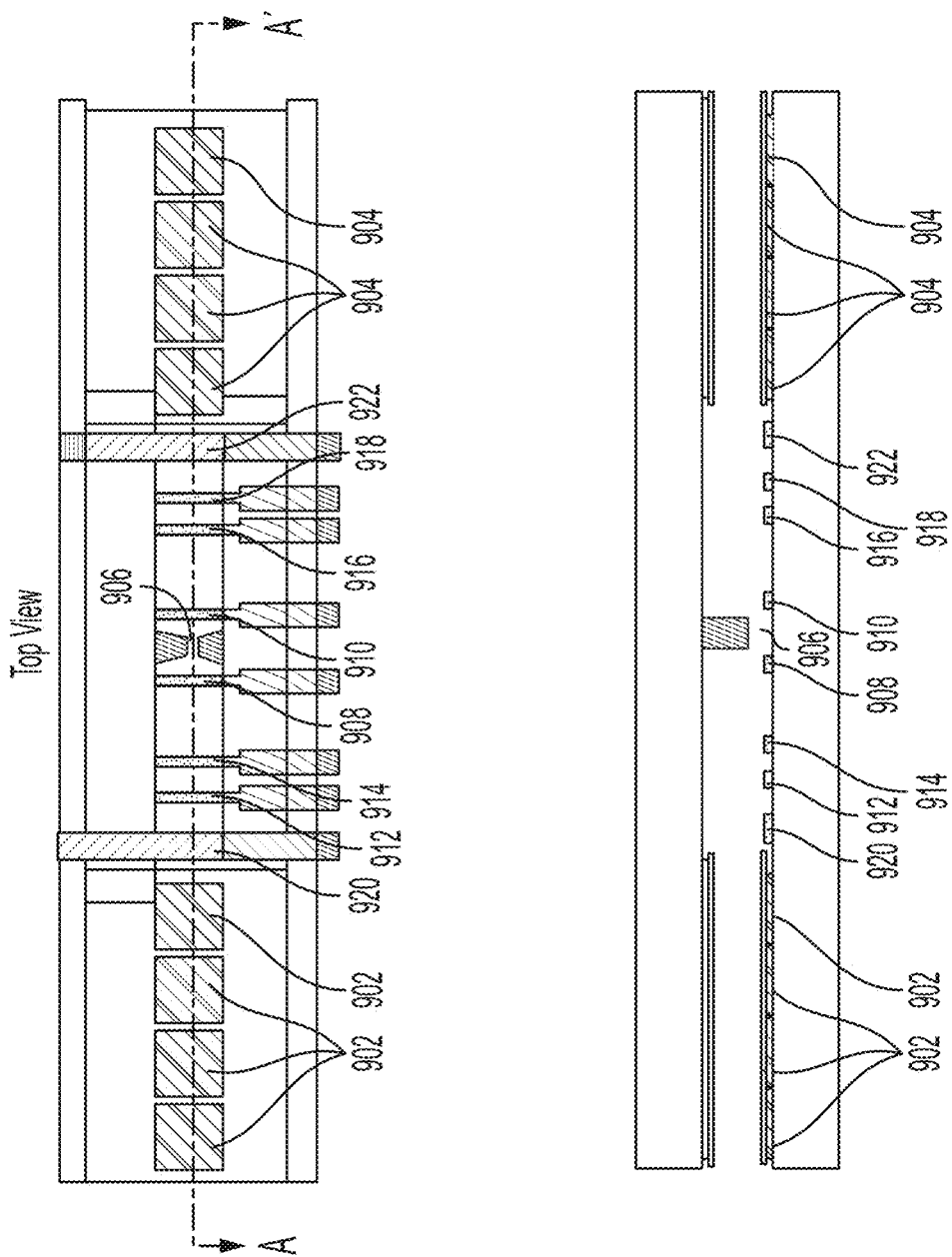

1. Electrowetting (EW) goverened flow introduces fluid into channels
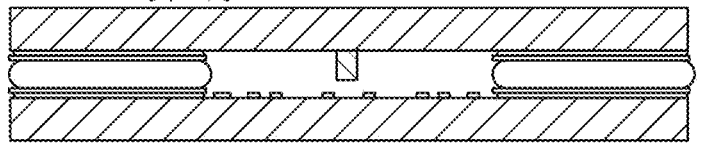
2. EW creates pressure driven flow into hydrophillic channel - drives capillary flow
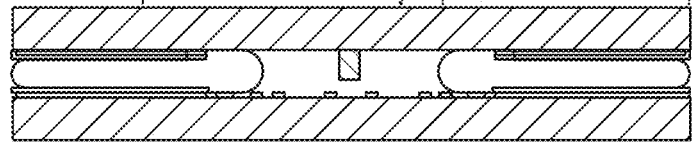
3. Fluid filled in channel
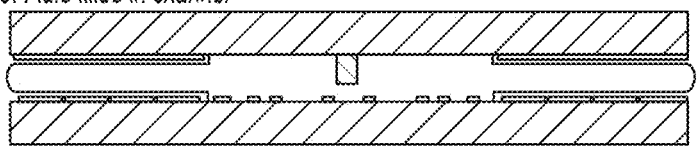
4. Air bubble or fluid with different conductivity introduced to separate particle mixtures
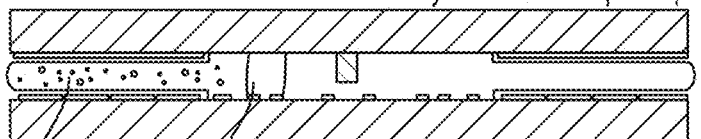
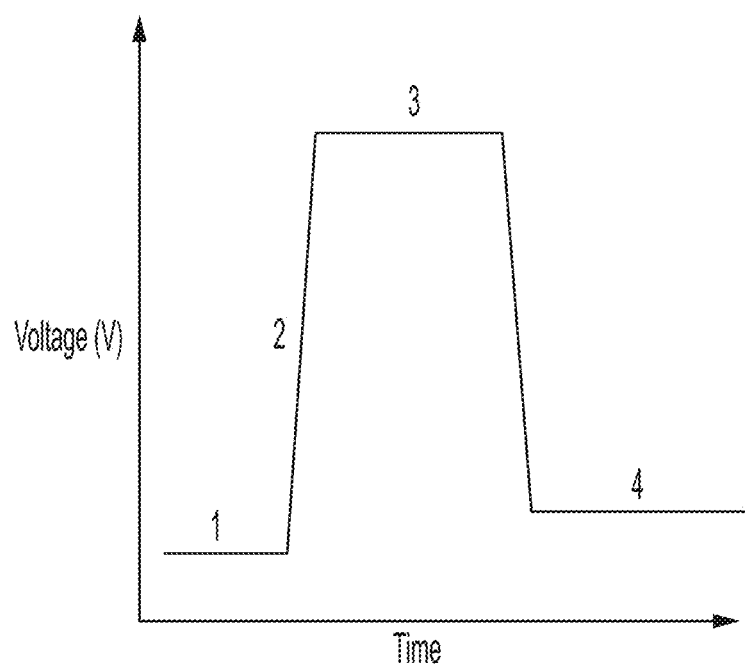
FIG. 10

Lymphocytes

Monocytes

Neutrophils

Platelets

Red Blood Cells

DEVICES, CARTRIDGES, AND SENSORS FOR ANALYZING A BIOLOGICAL SAMPLE

CROSS-REFERENCE TO RELATED APPLICATIONS

This application is a continuation of U.S. application Ser. No. 15/734,916, filed Dec. 3, 2020, which is a national stage application under 35 U.S.C. § 371 of International Application No. PCT/US2019/035548, filed internationally on Jun. 5, 2019; which claims the priority benefit of U.S. Provisional Patent Application No. 62/680,989, filed Jun. 5, 2018; U.S. Provisional Patent Application No. 62/680,992, filed Jun. 5, 2018; U.S. Provisional Patent Application No. 62/680,993, filed Jun. 5, 2018; U.S. Provisional Patent Application No. 62/756,007, filed Nov. 5, 2018; and U.S. Provisional Patent Application No. 62/756,011, filed Nov. 5, 2018; the disclosures of each of which are hereby incorporated herein by reference in their entirety.

TECHNICAL FIELD

Some aspects of the present invention relates to cartridges, systems, and methods for analyzing a biological sample. Some aspects of the invention relate to sensors for analyzing cells or analytes in a biological sample, as well as cartridges and systems that include such sensors. The invention further relates to methods of using the sensor, cartridge and system, as well as methods of analyzing a biological sample. Also provided are systems for controlling liquid movement by electrowetting using low-voltage electrowetting electrodes, and methods for controlling liquid movement using the low-voltage electrowetting electrodes.

BACKGROUND

Blood analysis for accurate medical diagnostics is typically performed in a clinical laboratory by a technician with specialized training using a complicated device. The blood sample needs to be carefully processed by mixing the sample with reagents before being analyzed by sensors or cell sorters to determine a blood count or to quantify protein, electrolyte or enzyme concentrations. This specialized training and equipment results in substantial patient expense and long wait times for important lab results. At-home or point-of-care blood analysis systems, such as a glucose meter, provide quick and convenient diagnostic results, but are often limited in accuracy or the scope of tests that can be performed.

Digital microfluidics using electrowetting electrodes is a developing field that explores actuation of liquid droplets by modulating hydrophobicity by applying an electrical field to the liquid. However, digital microfluidics applications are limited due to the relatively high voltage applied to the electrowetting electrodes to manipulate the liquid.

There continues to be a need for devices and systems that provide quick, accurate, and convenient blood analysis systems that do not require special training.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE INVENTION

Described herein is a cartridge for analyzing a biological sample, comprising: a sample receiving port configured to receive the biological sample; a sensor configured to analyze the biological sample; a cartridge space in fluid communication with the biological sample receiving port and the sensor; a plurality of electrowetting electrodes configured to transport the biological sample in the cartridge space, and combine the biological sample with one or more reagents; and a device interface configured to receive power from and communicate with a cartridge interface on a device, wherein the sensor and the plurality of electrowetting electrodes are in electrical communication with the device interface.

In some embodiments of the cartridge, the cartridge space is fluidly connected to one or more reagent reservoirs. In some embodiments, the one or more reagent reservoirs comprise a reagent. In some embodiments of the cartridge, the cartridge space comprises a reagent mixing region.

In some embodiments of the cartridge, the cartridge is a single-use cartridge.

In some embodiments of the cartridge, the cartridge comprises a waste reservoir configured to receive the biological sample after being analyzed by the sensor.

In some embodiments of the cartridge, the biological sample enters the sample receiving port through capillary action.

In some embodiments of the cartridge, the plurality of electrowetting electrodes comprises a plurality of coplanar electrodes. In some embodiments, the plurality of electrowetting electrodes further comprises a ground electrode on a surface opposite from the coplanar electrodes. In some embodiments, the ground electrode is common to two or more of the electrowetting electrodes. In some embodiments, at least one of the electrowetting electrodes is paired with an individual ground electrode.

In some embodiments of the cartridge, the electrowetting electrodes are coated with an insulating layer. In some embodiments, the insulating layer has a dielectric constant of about 3.9 or higher. In some embodiments, the insulating layer comprises hafnium oxide, barium strontium titanate, or strontium titanate, silica, or silicon nitride. In some embodiments, the insulating layer is coated on the electrode using atomic layer deposition, chemical vapor deposition, reactive ion beam deposition, sputter deposition, evaporation, spray deposition, spin coating, or sol-gel formation. In some embodiments, the insulating layer has a thickness of about 1 nm to about 5 µm. In some embodiments, the insulating layer is a fluid contacting surface. In some embodiments, the insulating layer comprises a nanostructured surface.

In some embodiments of the cartridge, the electrowetting electrodes are coated with a hydrophobic layer. In some embodiments, the hydrophobic layer is a fluid contacting layer. In some embodiments, the hydrophobic layer comprises a nanostructured surface. In some embodiments, the hydrophobic layer comprises a fluoropolymer, polydimethylsiloxane, a parylene, octadecanehydroxamic acid, stearic acid, octadecanephosphonic acid, 16-hydroryhexadecanehydroramic acid, or octadecanethiol. In some embodiments, the hydrophobic layer is coated over the insulating layer.

In some embodiments of the cartridge, the electrowetting electrodes comprise gold, silver, silver chloride, platinum, indium tin oxide, or a conductive carbon.

In some embodiments of the cartridge, the electrowetting electrodes are separated from a fluid contacting surface by about 1 nm to about 25 µm.

In some embodiments of the cartridge, the plurality of electrowetting electrodes is configured to transport the biological sample using a voltage of less than about 50 volts.

In some embodiments of the cartridge, the plurality of electrowetting electrodes is configured to transport the biological sample using a voltage of about 0.5 V to about 50V.

In some embodiments of the cartridge, the sensor is an impedance sensor. In some embodiments, the sensor is configured to detect a protein or measure an amount of the protein. In some embodiments, the sensor comprises a first sensing electrode functionalized with an affinity moiety, and a second sensing electrode paired with the first sensing electrode, wherein the sensor is configured to detect a change in impedance upon binding of an analyte or a protein to the affinity moiety. In some embodiments, the affinity moiety is an antibody, an antibody fragment, or an aptamer. In some embodiments, first sensing electrode is an electrowetting electrode. In some embodiments, the sensor further comprises a first electrowetting electrode and a second electrowetting electrode, wherein the first electrowetting electrode and the second electrowetting electrode are on opposite sides of the first sensing electrode or the second sensing electrode. In some embodiments, the first sensing electrode is an electrowetting electrode. In some embodiments, the plurality of electrowetting electrodes is configured to statically position at least a portion of the biological sample between the first sensing electrode and the second sensing electrode. In some embodiments, the first electrowetting electrode, the second electrowetting electrode, and the first sensing electrode are electrically connected to a voltage switching circuit configured to selectively activate one or none of the first electrowetting electrode, the second electrowetting electrode, or the first sensing electrode. In some embodiments, the voltage switching circuit is electrically connected to a switch configured to alternatively select an impedance sensing circuit or an electrowetting electrode supply circuit. In some embodiments, the impedance sensor comprises a pH-sensitive or ion-sensitive layer configured to modulate impedance based on pH or ion concentration. In some embodiments, the impedance sensor comprises a metal oxide semiconductor capacitor (MOSCap) sensor. In some embodiments, the MOSCap sensor is adjacent to the first sensing electrode and the second sensing electrode.

In some embodiments of the cartridge, the cartridge further comprises one or more optical windows.

In some embodiments of the cartridge, the sensor is a channel sensor, comprising: a first channel segment, a second channel segment, a pore or channel fluidly connecting the first channel segment and the second channel segment, and an electrode pair configured to apply an electrical current to the pore or channel, and to detect impedance within the pore or channel. In some embodiments, the electrode pair is configured to direct contact a liquid flowing through the channel sensor. In some embodiments, the channel sensor is a flow cytometer configured to count a number of cells in the biological sample. In some embodiments, the sensor is configured to differentiate between different types of cells. In some embodiments, the sensor is configured to differentiate between red blood cells, white blood cells, and platelets. In some embodiments, the sensor is configured to count a number of red blood cells, a number of white blood cells, or a number of platelets. In some embodiments, the sensor is configured to differentiate between eosinophils, basophils, neutrophils, monocytes, and lymphocytes. In some embodiments, the sensor is configured to count a number of eosinophils, a number of basophils, a number of neutrophils, a number of monocytes, or a number of lymphocytes. In some embodiments, the pore or channel is a micropore or a microchannel. In some embodiments, the electrical current is a multiplexed current comprising a plurality of alternating current components at different frequencies. In some embodiments, the electrical current is a multiplexed current comprising a (1) a direct current component or a low-frequency alternating current, and (2) a plurality of alternating current components at different frequencies. In some embodiments, the plurality of alternating current components comprises at least three alternating current components. In some embodiments, the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz. In some embodiments, the plurality of alternating current comprises at least five different alternating current components. In some embodiments, the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz. In some embodiments, the alternating current further comprises an additional alternating current at about 100 kHz or less, or about 50 kHz or less. In some embodiments, the electrode pair is configured to detect impedance at a sampling rate of about 100 kHz or more. In some embodiments, the electrode pair is configured to detect a real impedance component and an imaginary impedance component within the pore or channel. In some embodiments, the electrode pair is configured to detect a magnitude impedance component and a phase impedance component within the pore or channel. In some embodiments, the channel sensor is configured to detect an analyte concentration. In some embodiments, the analyte is a protein. In some embodiments, the cartridge comprises a reagent comprising an affinity moiety, and wherein the cartridge is configured to mix the reagent comprising the affinity moiety with the biological sample or a subsample derived therefrom, and transport the biological sample or subsample to the channel sensor. In some embodiments, the pore or channel is a nanopore or a nanochannel.

In some embodiments of the cartridge, the cartridge comprises a plurality of sensors.

In some embodiments of the cartridge, the biological sample is a blood sample.

Also provided herein is a system for analyzing a biological sample, comprising: any one of the above-described cartridges; and a device comprising a cartridge interface configured to interface with the cartridge, the device configured to power and operate the cartridge. In some embodiments, the device is configured to power and operate two or more different types of cartridges. In some embodiments, the device further comprises one or more processors and a non-transitory computer-readable storage medium storing one or more programs configured to be executed by the one or more processors, the one or more programs comprising instructions for (a) operating the plurality of electrowetting electrodes in the cartridge to transport the biological sample within the cartridge, and (b) operating the sensor. In some embodiments, the one or more programs comprise instructions for operating the plurality of electrowetting electrodes in the cartridge to continuously transport the biological sample through the sensor. In some embodiments, the one or more programs comprise instructions for operating the plurality of electrowetting electrodes in the cartridge to statically position the biological sample within the sensor. In some embodiments, the one or more programs comprise instructions for determining a cell count or an analyte concentration based on a multivariate pattern of a detected impedance signal at one or more frequencies. In some embodiments, the multivariate pattern comprises one or more of an impedance peak height, an impedance peak width, an impedance peak area, or an impedance peak half-width peak height. In some embodiments, the multivariate pattern comprises a real impedance component and an imaginary impedance component. In some embodiments, the multivariate pattern comprises of magnitude of the impedance component and phase of the impedance component. In some embodiments, the one or more programs comprise instructions for calibrating the sensor. In some embodiments, the device is a handheld device.

Further provided herein is a method of analyzing a biological sample, comprising: depositing a biological sample into a cartridge; transporting the biological sample within the cartridge using a plurality of electrowetting electrodes; analyzing the biological sample using one or more sensors within the cartridge to generate analytical data; and transmitting the analytical data from the cartridge. In some embodiments, the method comprises mixing the biological sample with one or more reagents within the cartridge. In some embodiments, the biological sample is received by the cartridge using capillary action. In some embodiments, the method further comprises transporting the biological sample into a waste reservoir within the cartridge after analyzing the biological sample. In some embodiments, the cartridge is disposed of after a single use. In some embodiments, analyzing the biological sample comprises counting a number of cells in the biological sample, wherein the analytical data relates to the number of cells. In some embodiments, analyzing the biological sample comprises comprising differentiating two or more different cell types. In some embodiments, analyzing the biological sample comprises comprising differentiating between red blood cells, white blood cells, and platelets. In some embodiments, analyzing the biological sample comprises counting white blood cells, counting red blood cells, or counting platelets. In some embodiments, analyzing the biological sample comprises differentiating between eosinophils, basophils, neutrophils, monocytes, and lymphocytes. In some embodiments, analyzing the biological sample comprises counting a number of eosinophils, a number of basophils, a number of neutrophils, a number of monocytes, or a number of lymphocytes. In some embodiments, analyzing the biological sample comprises applying an electrical current to the biological sample and recording a multiplexed impedance of the electrical current. In some embodiments, the electrical current is a mixed current comprising a plurality of alternating current components at different frequencies. In some embodiments, the electrical current is a mixed current comprising a direct current component and a plurality of alternating current components at different frequencies. In some embodiments, the electrical current is a mixed current comprising at least five alternating current components at different frequencies. In some embodiments, the method comprises self-calibrating at least one of the sensors to detect different cell sizes, material characteristics and/or concentration. In some embodiments, analyzing the biological sample comprises continuously flowing the biological sample through at least one of the sensors during analysis.

In some embodiments of the method, the biological sample is transported within the cartridge using a voltage of about 50V or less. In some embodiments, the biological sample is transported within the cartridge using a voltage of about 0.5 V to about 50V.

In some embodiments of the method, analyzing the biological sample comprises determining a concentration of an analyte or a protein within the biological sample. In some embodiments, analyzing the biological sample comprises statically positioning the biological sample on at least one of the sensors. In some embodiments, the biological sample is statically positioned on the sensor using electrowetting electrodes.

In some embodiments of the method, determining the concentration of the analyte or the protein within the biological sample comprises: binding the analyte or the protein to an affinity moiety bound to an electrode within one of the sensors, and measuring an impedance change resulting from the analyte or the protein binding to the affinity moiety. In some embodiments, the affinity moiety is an antibody, an antibody fragment, or an aptamer.

Also described herein is a sensor, comprising: a first channel segment; a second channel segment; a pore or a channel fluidly connecting the first channel segment and the second channel segment; an electrode pair configured apply a multiplexed electrical current or voltage to the pore or channel; and an electrode pair configured to detect impedance at a plurality of frequencies within the pore or channel, wherein the detected impedance comprises at least a first multivariate impedance pattern at a first frequency and a second multivariate impedance pattern at a second frequency; wherein the electrode pair configured to apply the multiplexed electrical current and the electrode pair configured to detect the impedance are the same electrode pair or different electrode pairs. In some embodiments, the first multivariate impedance pattern and the second multivariate impedance pattern each comprise a real impedance component and an imaginary component. In some embodiments, the first multivariate impedance pattern and the second multivariate impedance pattern each comprise a magnitude of the impedance component and a phase component.

Also provided herein is a cartridge, comprising the sensor described above, wherein the cartridge is configured to analyze a biological sample. In some embodiments, the cartridge comprises a plurality of electrowetting electrodes configured to transport one or more liquids within the cartridge. In some embodiments, the cartridge is configured to mix a reagent with the biological sample or a subsample derived therefrom, and transport the biological sample or subsample to the sensor. In some embodiments, the cartridge comprises a device interface electrically connected to the sensor.

Further provided herein is a device configured to interface with and operate the cartridge described above. In some embodiments, the device comprises one or more processors and a non-transitory computer-readable storage medium storing one or more programs configured to be executed by the one or more processors, the one or more programs comprising instructions for determining a cell count or an analyte concentration based on the detected impedance.

Also described herein is a system, comprising (a) a cartridge configured to analyze a biological sample, the cartridge comprising: (i) a sensor comprising: a first channel segment; a second channel segment; a pore or a channel fluidly connecting the first channel segment and the second channel segment; an electrode pair configured apply a multiplexed electrical current or voltage to the pore or channel; and an electrode pair configured to detect impedance at a plurality of frequencies within the pore or channel, wherein the electrode pair configured to apply the multiplexed electrical current and the electrode pair configured to detect the impedance are the same electrode pair or different electrode pairs; and (ii) a device interface electrically connected to the sensor; and (b) a device configured to interface with and operate the cartridge, comprising one or more processors and a non-transitory computer-readable storage medium storing one or more programs configured to be executed by the one or more processors, the one or more programs comprising instructions for determining a cell count or an analyte concentration based on the detected impedance at the plurality of frequencies. In some embodiments, the detected impedance comprises a real component and an imaginary component. In some embodiments, the detected impedance comprises a magnitude component and a phase component.

Also described herein is a system, comprising (a) a cartridge configured to analyze a biological sample, the cartridge comprising: (i) a sensor comprising: a first channel segment; a second channel segment; a pore or a channel fluidly connecting the first channel segment and the second channel segment; an electrode pair configured apply a multiplexed electrical current or voltage to the pore or channel; and an electrode pair configured to detect impedance at a plurality of frequencies within the pore or channel, wherein the electrode pair configured to apply the multiplexed electrical current and the electrode pair configured to detect the impedance are the same electrode pair or different electrode pairs; and (ii) a device interface electrically connected to the sensor; and (b) a device configured to interface with and operate the cartridge, comprising one or more processors and a non-transitory computer-readable storage medium storing one or more programs configured to be executed by the one or more processors, the one or more programs comprising instructions for determining a cell count or an analyte concentration based on the detected impedance, wherein the detected impedance comprises at least a first multivariate impedance pattern at a first frequency and a second multivariate impedance pattern at a second frequency. In some embodiments, the first multivariate impedance pattern and the second multivariate impedance pattern each comprise a real impedance component and an imaginary component. In some embodiments, the first multivariate impedance pattern and the second multivariate impedance pattern each comprise a magnitude impedance component and a phase component.

In some embodiments, the cartridge comprises a plurality of electrowetting electrodes configured to transport one or more liquids within the cartridge. In some embodiments, the cartridge is configured to mix a reagent with the biological sample or a subsample derived therefrom, and transport the biological sample or subsample to the sensor. In some embodiments, the cartridge comprises a device interface electrically connected to the sensor.

In some embodiments, the electrode pair configured to apply the multiplexed electrical current and the electrode pair configured to detect the impedance are the same electrode pair. In some embodiments, the electrode pair configured to apply the multiplexed electrical current and the electrode pair configured to detect the impedance are different electrode pairs.

In some embodiments, the multivariate impedance pattern comprises one or more of an impedance peak height, an impedance peak width, an impedance peak area, or an impedance peak half-width peak height.

In some embodiments, the electrode pair is in direct contact with an inner portion of the channel.

In some embodiments, the sensor is configured to count a number of cells in the biological sample. In some embodiments, the sensor is configured to differentiate between different types of cells. In some embodiments, the sensor is configured to differentiate between red blood cells, white blood cells, and platelets. In some embodiments, the sensor is configured to count a number of red blood cells, a number of white blood cells, or a number of platelets. In some embodiments, the sensor is configured to differentiate between eosinophils, basophils, neutrophils, monocytes, and lymphocytes. In some embodiments, the sensor is configured to count a number of eosinophils, basophils, neutrophils, monocytes, and lymphocytes.

In some embodiments, the pore or channel is a micropore or a microchannel.

In some embodiments, the sensor is configured to detect an analyte concentration. In some embodiments, the analyte is a protein. In some embodiments, the pore or channel is a nanopore or a nanochannel.

In some embodiments, the electrode pair configured to detect impedance comprises a first electrode within the first channel segment, and a second electrode within the second channel segment.

In some embodiments, the sensor comprises the channel, wherein the electrode pair configured to detect impedance is positioned within the channel In some embodiments, the electrode pair comprises a first electrode proximal to the first channel segment, and a second electrode proximal to the second channel segment. In some embodiments, the electrode pair comprises a first electrode on an upper surface of the channel, and a second electrode on a lower surface of the channel, and wherein the first electrode is positioned above the second electrode.

In some embodiments, the sensor further comprises an electrode pair configured to detect liquid flow within the sensor.

In some embodiments, the sensor comprises one or more isolation electrodes.

In some embodiments, the sensor comprises an entrance to the first channel segment proximal to an electrowetting electrode. In some embodiments, the sensor comprises an exit to the second channel segment proximal to an electrowetting electrode.

In some embodiments, the multiplexed electrical current comprises a plurality of alternating current components at different frequencies. In some embodiments, the multiplexed electrical current comprises a (1) a direct current component or a low-frequency alternating current, and (2) a plurality of alternating current components at different frequencies. In some embodiments, the plurality of alternating current components comprises at least three alternating current components. In some embodiments, the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz. In some embodiments, the plurality of alternating current components comprises at least five alternating current components. In some embodiments, the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz. In some embodiments, the current further includes an additional alternating current of about 100 kHz or less, such as about 50 kHz or less.

In some embodiments, the electrode pair configured to detect impedance is configured to detect impedance at a sampling rate of about 100 kHz or more.

Also provided herein is a method of determining a cell count in a biological sample, comprising: transporting the biological sample through a sensor comprising a channel or pore; applying a multiplexed electrical current or voltage to the channel or pore; detecting a multiplexed impedance within the channel or pore; and determining a cell count based on the detected multiplexed impedance. In some embodiments, the detected multiplexed impedance comprises a real component and an imaginary component at a plurality of different frequencies. In some embodiments, the detected multiplexed impedance comprises a magnitude component and a phase component at a plurality of different frequencies.

Further provided herein is a method of determining a cell count in a biological sample, comprising: transporting the biological sample through a sensor comprising a channel or pore; applying a multiplexed electrical current or voltage to the channel or pore; detecting a multiplexed impedance within the channel or pore, the multiplexed impedance comprising at least a first multivariate impedance pattern at a first frequency and a second multivariate impedance pattern at a second frequency; and determining a cell count based on the detected multiplexed impedance. In some embodiments, the first multivariate impedance pattern and the second multivariate impedance pattern each comprise a real impedance component and an imaginary component. In some embodiments, the first multivariate impedance pattern and the second multivariate impedance pattern each comprise a magnitude impedance component and a phase component. In some embodiments, the multivariate impedance pattern comprises one or more of an impedance peak height, an impedance peak width, an impedance peak area, or an impedance peak half-width peak height. In some embodiments, the biological sample directly contacts a pair of electrodes that detect the multiplexed impedance. In some embodiments, the method comprises differentiating between two or more different types of cells. In some embodiments, determining the cell count comprises determining a red blood cell count, a white blood cell count, or a platelet count in the biological sample. In some embodiments, determining the cell count comprises determining an eosinophil count, a basophil count, a neutrophil count, a monocyte count, and a lymphocyte count in the biological sample. In some embodiments, the method comprises transporting two or more subsamples of the biological sample through the sensor, wherein the two or more subsamples are processed at different pH levels or different electrolyte concentrations.

In some embodiments of the method described above, the method comprises transporting a marker into the sensor. In some embodiments, the marker is an air bubble or a low-conductivity solution. In some embodiments, the method comprises detecting the marker. In some embodiments, the marker triggers initiating or terminating recordation of the detected multiplexed impedance. In some embodiments, the method comprises determining a flow rate of the biological sample. In some embodiments, the method comprises using the determined flow rate to determine the cell count.

In some embodiments of the method described above, the method comprises filtering the biological sample.

In some embodiments of the method described above, the multiplexed electrical current comprises a plurality of alternating current components at different frequencies. In some embodiments, the multiplexed electrical current comprises a (1) a direct current component or a low-frequency alternating current, and (2) a plurality of alternating current components at different frequencies. In some embodiments, the plurality of alternating current components comprises at least three alternating current components. In some embodiments, the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz. In some embodiments, the plurality of alternating current components comprises at least five alternating current components. In some embodiments, the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz. In some embodiments, the current further includes an additional alternating current component of about 100 kHz or less, such as about 50 kHz or less.

Also provided herein is a method of detecting an analyte in a biological sample, comprising: transporting the biological sample through a sensor comprising a channel or pore, the biological sample comprising an analyte bound to an affinity moiety; applying an electrical current or voltage to the channel or pore; detecting an impedance within the channel or pore; and detecting the analyte based on the detected impedance. In some embodiments, the analyte is a protein or an electrolyte. In some embodiments, the affinity moiety is a multivalent affinity moiety. In some embodiments, the affinity moiety is charged. In some embodiments, the affinity moiety comprises an aptamer, an antibody, or an antibody fragment. In some embodiments, the affinity moiety comprises an aptamer bound to an avidin or an avidin derivative. In some embodiments, the method comprises mixing the biological sample with a reagent comprising the affinity moiety. In some embodiments, detecting the analyte based on the detected impedance comprises distinguishing between an affinity moiety bound to the analyte and an unbound affinity moiety.

In some embodiments of the method described above, the method comprises transporting a marker into the sensor. In some embodiments, the marker is an air bubble or a low-conductivity solution. In some embodiments, the method comprises detecting the marker. In some embodiments, the marker triggers initiating or terminating recordation of the detected multiplexed impedance. In some embodiments, the method comprises determining a flow rate of the biological sample. In some embodiments, the method comprises using the determined flow rate to determine a concentration of the analyte.

Also described herein is an electrowetting electrode array, comprising: a plurality of coplanar electrowetting electrodes coated with and spaced by an insulating layer; wherein the electrowetting array comprises a hydrophobic liquid contact surface, and wherein the electrowetting array is configured to transport an aqueous liquid using a voltage of about 50 volts or less. In some embodiments, the insulating layer comprises the hydrophobic liquid contact surface. In some embodiments, the insulating layer comprises a nanostructured surface. In some embodiments, the insulating layer is coated with a hydrophobic layer comprising the hydrophobic liquid contact surface. In some embodiments, the hydrophobic layer comprises a nanostructured surface. In some embodiments, the hydrophobic layer comprises a fluoropolymer, polydimethylsiloxane, a parylene, octadecanehydroxamic acid, stearic acid, octadecanephosphonic acid, 16-hydroryhexadecanehydroramic acid, or octadecanethiol. In some embodiments, the plurality of electrowetting electrodes is configured to transport the aqueous liquid using a voltage of about 0.5 volts to about 50 volts.

In some embodiments, the insulating layer has a dielectric constant of about 3.9 or higher. In some embodiments, the insulating layer comprises hafnium oxide, barium strontium titanate, or strontium titanate, silica, or silicon nitride. In some embodiments, the insulating layer is coated on the electrode using atomic layer deposition, chemical vapor deposition, reactive ion beam deposition, sputter deposition, evaporation, spray deposition, spin coating, or sol-gel formation. In some embodiments, the insulating layer has a thickness of about 1 nm to about 5 μm.

In some embodiments, the electrowetting electrodes comprise gold, silver, silver chloride, platinum, indium tin oxide, or a conductive carbon.

In some embodiments, the electrowetting electrodes are separated from the hydrophobic liquid contact surface by about 1 nm to about 25 μm.

In some embodiments, the plurality of electrowetting electrodes further comprises a ground electrode parallel to the coplanar electrowetting electrodes, wherein the hydrophobic liquid contact surface is between the ground electrode and the coplanar electrowetting electrodes. In some embodiments, the ground electrode is common to two or more of the electrowetting electrodes. In some embodiments, at least one of the electrowetting electrodes is paired with an individual ground electrode.

In some embodiments, the electrowetting electrode array comprises an impedance sensor comprising a sensing electrode and a functionalized liquid contact surface, wherein the functionalized liquid contact surface is functionalized with an affinity moiety that specifically binds a target analyte. In some embodiments, the sensor further comprises a second sensing electrode paired with the first sensing electrode, wherein the sensor is configured to detect a change in impedance upon binding of an analyte or a protein to the affinity moiety. In some embodiments, the target analyte is a protein. In some embodiments, the affinity moiety is an antibody, an antibody fragment, or an aptamer. In some embodiments, the impedance sensor further comprises a metal oxide semiconductor capacitor (MOSCap) sensor comprising a pH-sensitive or ion-sensitive layer configured to modulate impedance based on pH or ion concentration.

In some embodiments, the aqueous liquid comprises a biological sample. In some embodiments, the biological sample comprises a blood sample.

Also provided herein is a cartridge for analyzing a biological sample, comprising: a sample receiving port configured to receive the biological sample; a sensor configured to analyze the biological sample; a chamber or a channel in fluid communication with the biological sample receiving port and the sensor, the chamber or the channel comprising the electrowetting electrode array described above; and a device interface configured to receive power from and communicate with a cartridge interface on a device, wherein the sensor and the plurality of electrowetting electrodes are in electrical communication with the device interface. In some embodiments, the chamber or the channel is fluidly connected to one or more reagent reservoirs, wherein the electrowetting electrode array extends into the one or more reagent reservoirs. In some embodiments, the electrowetting electrode array comprises a reagent mixing region.

Further provided herein is a system for analyzing a biological sample, comprising: the cartridge described above; and a device comprising a cartridge interface configured to interface with the cartridge, the device configured to operate the electrowetting electrode array. In some embodiments, the device is a handheld device.

Also provided herein is a method of transporting a liquid, comprising: positioning an aqueous liquid on a first hydrophobic liquid contact surface above an inactivated first electrowetting electrode; and activating a second electrowetting electrode by applying a voltage of about 50 volts or less to the second electrowetting electrode, thereby transporting the aqueous liquid from the first hydrophobic liquid contact surface to a second hydrophobic liquid contact surface above the second electrowetting electrode; wherein the first electrowetting electrode and the second electrowetting electrode are coated with and separated by an insulating layer. In some embodiments, the aqueous liquid comprises a biological sample.

In some embodiments, the method comprises transporting a reagent to the second liquid contacting surface, thereby mixing the reagent with the aqueous liquid. In some embodiments, the reagent is transported by activating the second electrowetting electrode.

In some embodiments of the above method, the biological sample is transported within the cartridge using a voltage of about 0.5 V to about 50V.

In some embodiments of the above method, the first hydrophobic liquid contact surface or the second hydrophobic liquid contact surface is a nanostructured surface.

In some embodiments of the above method, the insulating layer comprises the first hydrophobic liquid contact surface and the second hydrophobic liquid contact surface.

In some embodiments of the above method, the insulating layer is coated with a hydrophobic layer comprising the first hydrophobic liquid contact surface and the second hydrophobic liquid contact surface. In some embodiments, the hydrophobic layer comprises a fluoropolymer, polydimethylsiloxane, a parylene, octadecanehydroxamic acid, stearic acid, octadecanephosphonic acid, 16-hydroryhexadecanehydroramic acid, or octadecanethiol.

In some embodiments of the above method, the insulating layer has a dielectric constant of about 3.9 or higher. In some embodiments, the insulating layer comprises hafnium oxide, barium strontium titanate, or strontium titanate, silica, or silicon nitride.

In some embodiments of the above method, the insulating layer has a thickness of about 1 nm to about 5 μm.

In some embodiments of the above method, the first electrowetting electrode is separated from the first hydrophobic liquid contact surface by about 1 nm to about 25 μm, and the second electrowetting electrode is separated from the second hydrophobic liquid contact surface by about 1 nm to about 25 μm.

BRIEF DESCRIPTION OF THE DRAWINGS

FIG. 1A illustrates an exemplary cartridge for analyzing a biological sample.

FIG. 9 illustrates a top view and a side view of a channel sensor that includes a pair of impedance detection electrodes, two pairs of flow detection electrodes and two isolation electrodes.

FIG. 10 shows initiation of operation of the channel sensor, with a plot below demonstrating DC voltage detected by the first pair of flow detection electrodes.

DETAILED DESCRIPTION OF THE INVENTION

Figure 1B:
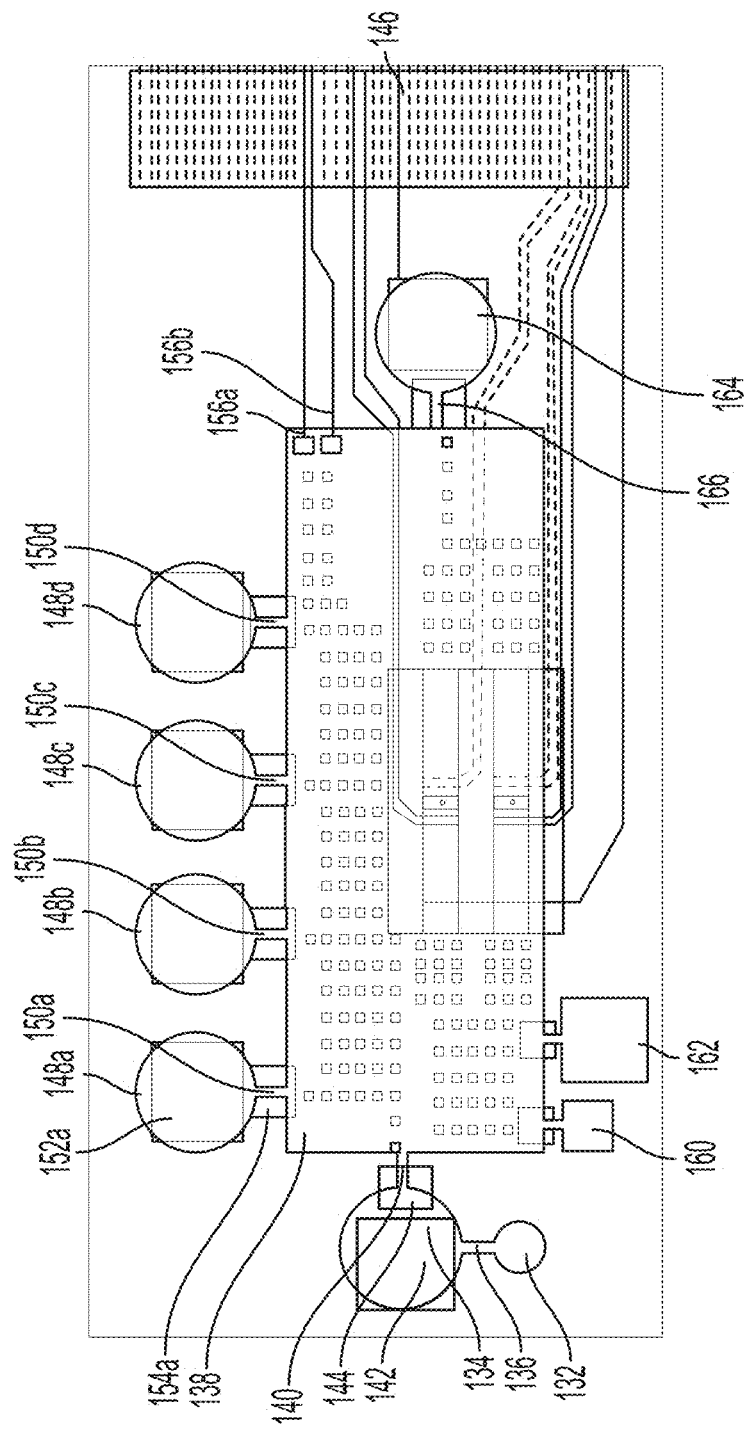
FIG. 1B illustrates another exemplary embodiment of the cartridge.

Cartridges and systems for analyzing a biological sample (such as a blood, serum, saliva, sweat, tears, mucus, urine, or any other biological sample or derivative suspended in a fluid), as was well as methods of analyzing a biological system, are described herein. Different types of cartridges can be used with a controlling device, and the different types of cartridges can be configured to perform different assays or assay panels of the biological sample. For example, in some embodiments, the cartridge is configured to perform a complete blood count (CBC) assay. The CBC assay can distinguish and count different blood cell types, such as red blood cells, platelets, and white blood cells (including eosinophils, basophils, neutrophils, monocytes, and lymphocytes). In some embodiments, the cartridge is configured to perform a comprehensive metabolic panel (CMP). The same controlling device can engage with the different cartridges, allowing for a single versatile device that can used to perform a plurality of assays by interfacing with a selected cartridge.

The cartridge includes a sample receiving port that can receive the biological sample, a sensor to analyze the sample, and a cartridge space that fluidly connects the biological sample receiving port to the sensor. A plurality of electrowetting electrodes can transport the biological sample in the cartridge space, and can optionally split the sample into smaller volume and/or further combine the biological sample with one or more reagents to processes the biological sample. The cartridge can interface to a device through a device interface on the cartridge, which is configured to receive power from and communicate with the device. The sensor and the plurality of electrowetting electrodes are in electrical communication with the device interface, thereby allowing the device to operate the cartridge.

The sensor is used to analyze the biological sample, and can be, for example, a sensor configured to detect a protein (which may be, for example, an enzyme) or electrolyte, or count a number and/or type of cells in the biological sample. In some embodiments, the cartridge includes two, three, four, or more sensors that may have the same or different functions. For example, the cartridge can include a first sensor for detecting a protein and a second sensor for counting a number of cells, or a hybrid sensor that can both detect a protein and count a number of cells.

The biological sample can be analyzed by depositing the biological sample into the cartridge, and transporting the biological sample within the cartridge using a plurality of electrowetting electrodes. The biological sample is introduced into the cartridge, for example by directly placing a fixed volume of the biological sample into the input port or through an interface which allows placement of a blood collection tube, thereby creating a fluid path from the tube to the input port. In some embodiments, the biological sample is prepared by splitting the blood samples into multiple droplets of a predetermined volume. The sample can be mixed with one or more reagents within the cartridge to process the biological sample, which is analyzed using one or more sensors within the cartridge to generate analytical data. The analytical data is then transmitted to the device.

The plurality of electrowetting electrodes in the cartridge allows the biological sample to be carefully transported within the cartridge using a low-voltage force. The cartridge can include reagent reservoirs, and a reagent within the reservoir can be combined with the biological sample on an electrowetting electrode before being transported to a sensor for analysis.

The cartridges are preferably single-use, disposable cartridge that includes the necessary reagents and correct volumes for processing the biological sample without user intervention. The user need only apply the biological sample on the cartridge, and the device can operate the cartridge to properly process and analyze the sample. Upon completion of the analysis, the cartridge can be disposed of. Different cartridge types can be manufactured that include different analytical tests depending on the sensor or sensors contained within the cartridge, and a single device may interface with different cartridge types.

Also described herein are sensors that use multiplexed impedance sensing to analyze biological samples. The biological samples can be analyzed, for example, to detect or quantify a protein (which may be, for example, an enzyme) or electrolyte, or count a number and/or type of cells (such as red blood cells, white blood cells, or platelets) in the biological sample. Such biological samples can include, for example, blood, serum, saliva, sweat, tears, mucus, urine, or any other biological sample or derivative suspended in a fluid. In some embodiments, the sensor is included on a cartridge that is configured to receive and analyze the biological sample. The cartridge can be part of a system that receives and operates the cartridge.

In some embodiments, the sensor includes an electrode pair configured to detect impedance at a plurality of frequencies within the pore or channel. The detected impedance can include a multivariate impedance pattern at one or more frequencies, and the one or more multivariate impedance patterns can be analyzed to count a number of cells and/or distinguish cell types. The multivariate impedance pattern can include, for example, a signal (such as amplitude) from a real component and a signal (such as amplitude) from an imaginary component of the impedance. Alternatively, the multivariate impedance pattern can include, for example, a signal (such as amplitude) from a magnitude component and a signal (such as amplitude) from a phase component of the impedance.

Further disclosed herein are methods for determining a cell count in a biological sample. The cell count can include counting a plurality of different types of cells, such as a count of white blood cells, a count of red blood cells, and/or a count of platelets in the biological sample. In some embodiments, the cell count can include a white blood differential, and can include a count of basophils, a count of eosinophils, a count of lymphocytes, a count of neutrophils, and/or a count of monocytes. The method can include transporting the biological sample (or a subsample) through a sensor that includes a channel or pore. A multiplexed electrical current or voltage is applied to the channel or pore, and a multiplexed impedance can be detected within the channel or pore. The multiplexed impedance includes at least a first multivariate impedance pattern at a first frequency and a second multivariate impedance pattern at a second frequency. The cell count can then be determined based on the detected multiplexed impedance. As further explained herein, the multiplexed impedance pattern can include features of the detected impedance signals as cells or other particles flow through the channel or pore. Such features can include, but are not limited to, one or more of an impedance peak height, an impedance peak width, an impedance peak area, or an impedance peak half-width peak height. The feature can be from a real component or an imaginary component of the impedance signal. The feature can be from a magnitude component or phase component of the impedance signal.

Also described herein is a method of method of detecting an analyte, such as a protein or electrolyte, in a biological sample. The method includes transporting the biological sample through a sensor that includes a channel or pore, applying an electrical current or voltage to the channel or pore, and detecting an impedance within the channel or pore. The biological sample includes an analyte bound to an affinity moiety, and the impedance is affected when the analyte bound to the affinity moiety passes through the channel or pore. Therefore, the analyte can be detected based on the detected impedance.

In some optional embodiments of the electrowetting electrode array described herein, the electrowetting electrode array is configured to transport an aqueous liquid (such as a biological sample or a processed biological sample) by applying a low voltage (about 50 volts or less) to an electrowetting electrode. The voltage applied to the electrode results in a change to the liquid contact angle, which actuates the liquid. By transporting the aqueous liquid using low voltage, the electrowetting electrode array can be used in low power devices and applications, such as point-of-care assay systems. The point-of-care assay system can include a cartridge with the electrowetting electrode array, which is configured to analyze a biological sample. The cartridge, include the electrowetting array within the cartridge, can be operated by a device, which may be a hand-held and/or battery powered device.

In some embodiments, an electrowetting electrode array includes a plurality of coplanar electrowetting electrodes coated with and spaced by an insulating layer; wherein the electrowetting array comprises a hydrophobic liquid contact surface, and wherein the electrowetting array is configured to transport an aqueous liquid using a voltage of about 50 volts or less. As further described herein, the hydrophobicity (i.e., contact angle) of the liquid contact surface, as well as the distance and/or materials separating the liquid contact surface and the electrode, are selected to lower the voltage needed to transport the aqueous liquid sample from one electrowetting electrode to another electrowetting electrode.

Liquid can be transported by positioning an aqueous liquid on a first hydrophobic liquid contact surface above an inactivated first electrowetting electrode; and activating a second electrowetting electrode by applying a voltage of about 50 volts or less to the second electrowetting electrode, thereby transporting the aqueous liquid from the first hydrophobic liquid contact surface to a second hydrophobic liquid contact surface above the second electrowetting electrode. The first electrowetting electrode and the second electrowetting electrode are coated with and separated by an insulating layer.

Cartridges for analyzing a biological sample (such as a blood, serum, saliva, sweat, tears, mucus, urine, or any other biological sample or derivative suspended in a fluid) can include the electrowetting electrode array to transport and/or process the biological sample within the cartridge. The cartridge can further include one or more sensors to analyze the biological sample. Different types of cartridges can be used with a controlling device, and the different types of cartridges can be configured to perform different assays or assay panels of the biological sample. The same controlling device can engage with the different cartridges, allowing for a single versatile device that can used to perform a plurality of assays by interfacing with a selected cartridge.

Definitions

As used herein, the singular forms "a," "an," and "the" include the plural reference unless the context clearly dictates otherwise.

Reference to "about" or "approximately" a value or parameter herein includes (and describes) variations that are directed to that value or parameter per se. For example, description referring to "about X" includes description of "X."

As used herein, the term "antibody" includes, but is not limited to, a monoclonal antibody, polyclonal, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies, a single chain antibody, and a Fc-containing polypeptide, such as an immunoadhesion. In some embodiments, the antibody may be of any heavy chain isotype (e.g., IgG, IgA, IgM, IgE, or IgD). In some embodiments, the antibody may be of any light chain isotype (e.g., kappa or gamma). The antibody may be non-human (e.g., from mouse, goat, or any other animal), fully human, humanized, or chimeric. In some embodiments, the antibody is a derivatized antibody.

The term "channel" refers to a tube, duct, or other passageway providing a linear liquid flow path.

It is understood that aspects and variations of the invention described herein include "consisting" and/or "consisting essentially of" aspects and variations.

A "high-kappa" or "high-κ" material is any material that has a dielectric constant of 3.9 or higher.

A "hydrophobic" material, surface, or layer is any material, surface, or layer that provides a water contact angle of 90 degrees or higher at 25° C.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

Analytical Cartridge

The cartridge receives a biological sample, which can be deposited by a user, and processes and analyzes the biological sample. The cartridge includes a sample receiving port configured to receive the biological sample; a sensor configured to analyze the biological sample; a chamber or a channel in fluid communication with the biological sample receiving port and the sensor; a plurality of electrowetting electrodes configured to transport the biological sample in the chamber or the channel, and combine the biological sample with one or more reagents; and a device interface configured to receive power from and communicate with a cartridge interface on a device, wherein the sensor and the plurality of electrowetting electrodes are in electrical communication with the device interface. The cartridge is preferably single-use cartridge, and a new cartridge can be used to analyze a different biological sample. In some embodiments, the plurality of electrowetting electrodes is configured to (1) transport the biological sample in the chamber or the channel, and (2) combine the biological sample with one or more reagents, within the cartridge.

Fluid actuation within the cartridge may be performed using electrowetting electrodes, although other modalities of liquid (e.g., sample) transport within the cartridge are considered. For example, in some embodiments, the cartridge includes one or mechanical pumps (such as syringe pumps, peristaltic pumps, and/or pneumatic pumps) to transport liquid within the cartridge. The one or more mechanical pumps may be used, for example, with one or more electronic fluidic valves. Thus, while certain embodiments, of the cartridge described herein use electrowetting electrodes for liquid movement and/or sample preparation, other liquid transport modalities may be used.

Exemplary biological samples that may be deposited into the cartridge include, but are not limited to, blood, plasma, serum, sweat, tear fluid, mucus, urine, or any other suitable liquid biological sample or biological sample derivative. In some embodiments, the sample has a volume of about 20 µL or more, such as a volume between about 20 µL and about 1 mL. For example, in some embodiments, the sample has a volume of about 20 µL to about 40 µL, about 40 µL to about 80 µL, bout 80 µL to about 150 µL, about 150 µL to about 300 µL, about 300 µL to about 600 µL, or about 600 µL to about 1 mL. The biological sample received by the cartridge may be divided within the cartridge to run different tests or to run redundant tests. The biological sample can be divided and/or metered (that is, to a predetermined volume) using the electrowetting electrodes. In some embodiments, the sample is divided to perform a redundant test 2, 3, 4, or more times (i.e., duplicate, triplicate, etc.). In some embodiments, the sample is divided to 2, 3, 4, 5, 6, 7, 8, 9, 10 or more different tests, which may each of which may or may not be redundantly performed. By way of example, a biological sample of 600 µL may be divided into 30 divided samples, each divided biological sample having 20 µL of the biological sample, which can be analyzed using 10 different analytical tests in triplicate.

The sample receiving port can include an inlet fluidly connected to a sample receiving chamber by a first sample port channel, and the sample receiving chamber can be fluidly connected to the chamber or channel of the cartridge through a second sample port channel. The volume of the sample receiving chamber determines the volume of sample received by the cartridge. Accordingly, in some embodiments, the volume of the sample receiving chamber is about 20 µL or more, such as between about 20 µL and about 1 mL. For example, in some embodiments, the sample receiving chamber has a volume of about 20 µL to about 40 µL, about 40 µL to about 80 µL, bout 80 µL to about 150 µL, about 150 µL to about 300 µL, about 300 µL to about 600 µL, or about 600 µL to about 1 mL. The sample deposited into the inlet flows into the sample receiving chamber through the first sample port channel through capillary action. The sample is retained in the sample receiving chamber until the plurality of electrowetting electrodes are operated to transport the sample from the sample receiving chamber. As further discussed herein, the electrowetting electrodes are preferably coated with a material that provides a hydrophobic fluid contact surface, which prevents the sample from flowing into the chamber or channel of the device through the second sample port channel without electrowetting actuation. The second sample port channel and/or sample receiving chamber may optionally include one or more of the electrowetting electrodes, which can aid in transferring the biological sample from the sample receiving chamber into the main chamber or channel. Also optionally, the cartridge can include a filter configured to filter the biological sample before it enters the main chamber. The filter may, for example, remove debris or larger particles from the biological sample before the sample is processed and analyzed in the cartridge. The filter can be positioned, for example within the second sample port channel or the first sample port channel.

The sample receiving port is fluidly connected to a main chamber or channel, which is fluidly connected to one or sensors or other cartridge components. If the cartridge includes a main channel to transport the biological sample throughout the cartridge, the channel is preferably sized to limit capillary movement of the sample within the channel. The lower portion of the chamber or channel includes a plurality of electrowetting electrodes, which may be coated as described herein. The main chamber or channel also includes a top and sidewalls to enclose the channel or chamber, although the sidewalls may optionally be rounded to avoid corners. The plurality of electrowetting electrodes is configured to transport the biological sample in the chamber or channel, for example to a reagent mixing region, a sensor, or a waste reservoir, through electrowetting actuation. In some configurations, the plurality of electrowetting electrodes are positioned on the bottom of the chamber or channel, and in some embodiments the plurality of electrowetting electrodes are positioned on the bottom and top of the chamber or channel Having a main chamber in the cartridge with an electrowetting array allows movement of fluids within the cartridge to be programmatically controlled using electrowetting electrodes, as opposed to a channel which forces linear movement of the fluids.

The chamber or the channel can be fluidly connected to one or more reagent reservoirs, which may be pre-loaded with a reagent to process the biological sample. The reagent reservoirs may be sized to contain the desired amount of reagent. The reagent reservoirs are connected to the main chamber or channel through a reservoir channel One or more of the reagent reservoirs and/or reservoir channels can optionally include one or more of the electrowetting electrodes to transport the reagent from the reagent chamber into the main chamber or channel. The electrowetting electrodes optionally transport the sample and a reagent into a reagent mixing region, thereby combining the biological sample with one or more reagents to form a processed biological sample. The reagents may be used, for example, to alter a pH, performed a chemical and/or biological reaction, or dilute (or serially dilute) the biological sample to form the processed biological sample. In some embodiments, one or more of the reagents are configured to modify or lyse cells in the sample or a subset of cells in the sample. For example, in some embodiments, a lysis reagent lyses cells in the sample, or only red blood cells in the sample. Targeted lysis of red blood cells in the sample is optionally performed, for example, to process the sample for counting white blood cells in the sample or to measure a hemoglobin content or concentration. In some embodiments, the one or more reagents can modify a cell surface (e.g., a cell membrane) with a marker (e.g., an affinity moiety marker, such as an aptamer or antibody (or fragment), which may be labeled), which specifically binds to the cell type for identification. In some embodiments, the one or more reagents includes a marker that can permeate into cells or a targeted subset of cells, which can modify the interior of the cell (e.g., the cytoplasm or nucleus of the cell), which can be used for cell type identification.

In some embodiments, one or more reagents includes a buffer, an anticoagulant (such as ethylenediaminetetraacetic acid (EDTA)), or a stabilizer (such as a stabilizer protein, for example albumin), and/or a viscosity adjusting agent (such as glycerol, e.g., from about 0.1% to about 50% glycerol).

Some reagents may be used to dilute the sample or a portion of the sample. In some embodiments, one or more reagents are added to the sample or portion of the sample to dilute the sample at a ratio of sample to dilution reagent at a ratio of about 1:1 to about 1:2000 (such as about 1:1 to about 1:5, about 1:5 to about 1:10, about 1:10 to about 1:20, about 1:20 to about 1:50, about 1:50 to about 1:100, about 1:100 to about 1:300, about 1:300 to about 1:500, about 1:500 to about 1:1000, or about 1:1000 to about 1:2000).

The cartridge includes one or more sensors that are fluidly connected to the chamber or channel. The cartridge may include 1, 2, 3, 4, 5 or more different sensors, and may include 1, 2, 3, 4, 5 or more redundant sensors of a given type of sensor. Exemplary sensors that can be used with the cartridge are described in further detail herein. In brief, exemplary sensors include optical sensors and impedance sensors, which can be configured to analyze the biological sample. In some embodiments, the sensor is configured to detect a protein or electrolyte, or measure a protein concentration or an electrolyte concentration in the biological sample. In some embodiments, the sensor is a channel sensor (e.g., a flow cytometer, which is configured to count a number of cells in the biological sample, or a flow analyte sensor, which is configured to detect or quantify an amount of an analyte such as a protein or enzyme). The flow cytometer may be able to distinguish between different cell types (e.g., red blood cells, white blood cells, or platelets), and is configured to count for one or more different types of cells.

The cartridge can include a waste reservoir configured to receive the biological sample after being analyzed by the one or more sensors. The waste reservoir is fluidly connected to the main chamber, for example by a waste channel. The electrowetting electrodes can transport the analyzed biological sample into the waste reservoir through electrowetting actuation. Optionally, the waste channel and/or the waste reservoir can include one or more electrowetting electrodes to control transport of the biological sample into the waste reservoir. In some embodiments, once the biological sample has been transported into the waste reservoir, it is retained in the waste reservoir through a hydrophobic effect. The electrowetting electrodes adjacent to the waste reservoir can be coated with a hydrophobic fluid contacting layer, and fluid in the waste reservoir remains there to avoid the hydrophobic fluid contacting layer when the electrowetting electrodes are not used.

The cartridge further includes a device interface, which is configured to receive power from and communicate with a cartridge interface on a device. The device interface includes a plurality of electrodes that are in electrical communication with the device electrodes with the cartridge and the device are engaged with each other. The one or more sensors and the electrowetting electrodes are in electrical communication with the device interface through the electrodes. This allows for communication between the device and the cartridge, and the device can operate the electrowetting electrodes to transport the biological sample within the cartridge, including egress from the sample receiving port and/or ingress into the waste reservoir. The device can further operate the electrowetting electrodes to transport the one or more reagents within the cartridge, and to combine the biological sample with the one or more reagents. The device can further operate the one or more sensors within the cartridge. The one or more sensors can generate analytical data by analyzing the biological sample, which is transmitted to the device through the device interface. In this manner, the device can receive the analytical data.

Optionally, the cartridge can include one or more (e.g., 1, 2, 3, 4, 5, or more) optical windows, which may be optically transparent on the top and/or bottom of the cartridge. These optical windows are used in combination with the impedance sensors or as standalone detectors. In both standalone or combination for detection of reaction with a reagent either through color change or fluorescence emission for selective detection of an analyte or protein binding. In some embodiments, when used in combination with the impedance sensors, the optical detection can be used to detect interfering substances not limited to Lipids, Bilirubin C, Bilirubin F, Chyle, Hemolytic Hemoglobin, Glucose and/or alternatively to detect the quality of the sample to apply a correction factor for measurements. Sample quality checks include measurement of sample turbidity. If the cartridge includes more than one optical window, the optical windows may be of the same size or of different sizes. The optical window is configured to allow light to pass through the sample, for example to capture an image of the sample or assay the sample using optical microscopy or spectroscopy (e.g., fluorescence, infrared (IR), Raman, or UV/Vis absorption spectroscopy). The electrowetting electrodes can transport the biological sample, or a portion thereof, to the optical window, and the sample can be assayed or an image of the sample captured. In some embodiments, the device that operates the cartridge includes a light source and an optical detector that aligns with the optical window when the cartridge is engaged with the cartridge. The device can than assay the biological sample using the light source and the optical detector. In some embodiments, the device includes a camera that aligns with the optical window of the cartridge, and the camera can image the biological sample through the optical window when the cartridge is engaged with the device.

FIG. 1A illustrates an exemplary cartridge for analyzing a biological sample. The cartridge includes a sample receiving port that includes an inlet 102 fluidly connected to a sample receiving chamber 104 through a first sample port channel 106. The biological sample is deposited into the inlet 102 and travels through the first sample port channel 106 into the receiving chamber 104 by way of capillary action. The sample receiving chamber 104 is fluidly connected to the main chamber 108 through a second sample port channel 110. Optionally, the cartridge includes a filter (not shown) between the inlet 102 and the main chamber 108, which may be positioned, for example, within the first sample port channel 106 or the second sample port channel 110. The filter, if present, can remove larger debris in the biological sample. The main chamber 108 includes a plurality of electrowetting electrodes 112, which continue into the second sample port channel 110. The cartridge further includes a plurality of reagent reservoirs 114a, 114b, 114c, and 114d, which are fluidly connected to the main chamber 108 through reservoir channels 116a, 116b, 116c, and 116d. Although the exemplary cartridge illustrated in FIG. 1A shows four reagent reservoirs, it is understood that the cartridge can include any number of reservoirs, as determined by the test or tests to be performed using the cartridge. The plurality of electrowetting electrodes 112 extend into the reservoir channels 116a, 116b, 116c, and 116d, and the electrowetting electrodes 112 can be operated to transport reagents in the reservoir channels 116a, 116b, 116c, and 116d into a mixing region 118 of the main chamber 108. The biological sample and the reagents are transported into the mixing region 118 and combined to form the processed biological sample. Optionally, the main chamber 108 of the cartridge can include a filter. The biological sample can be transported through the filter using the electrowetting electrodes 112, for example to separate components of the biological sample (for example to isolate serum from whole blood). The plurality of electrowetting electrodes 112 can be operated to transport the processed biological sample, or a portion of the processed biological sample, to one or more sensors within the cartridge. Optionally, the biological sample is analyzed by a sensor without processing. The exemplary cartridge illustrated in FIG. 1A includes three impedance sensors 120a, 120b, and 120c, which are configured to measure an amount of a protein within the biological sample. The impedance sensors may be of the same type (i.e., redundant impedance sensors that perform the same assay) or of different types. Although the exemplary cartridge illustrated in FIG. 1A includes three impedance sensors, it is understood that the cartridge can include any number of impedance sensors, which may depend on the number of assays or assay redundancies for the particular cartridge. The illustrated cartridge further includes four channel sensors 122a, 122b, 122c, and 122d, although other embodiments of the cartridge may have additional or fewer channel sensors, which may be redundant or non-redundant. The channel sensor may be, for example, a flow cytometer, or may be configured to detect or quantify a protein. In the illustrated example, the plurality of electrowetting electrodes 112 includes functionalized electrodes that are part of the impedance sensors 120a, 120b, and 120c. However, the plurality of electrowetting electrodes 112 does not extend into the channel sensors 122a, 122b, 122c, and 122d, which use capillary action to pass the processed biological sample through the sensors. The cartridge further includes a waste reservoir 124 fluidly connected to the main chamber 108 through a waste channel 126. The plurality of electrowetting electrodes extends into the waste channel 126, and can be operated to transport the processed biological sample into the waste reservoir 124. The cartridge further includes a device interface 128 in electrical communication with the plurality of electrowetting electrodes 112 and the sensors 120a, 120b, 120c, 122a, 122b, 122c, and 122d.

The cartridge optionally includes an optical window 130. The optical window includes a transparent window at the top of the cartridge and a transparent window at the bottom of the cartridge, which allows light to pass through. The optical window 130 is fluidly connected to the main chamber 108, and the biological sample can be transported to the optical window 130 using the electrowetting electrodes 112. When the cartridge engages the device (not shown in FIG. 1A), a light source and an optical detector are positioned on opposite sides of the optical window 130, and the biological sample positioned in the optical window can be assayed using the device.

FIG. 1B illustrates another embodiment of a cartridge, with a different orientation of sensors. The main chamber illustrates a plurality of electrowetting electrodes to demonstrate the array, although the size and/or spacing of the electrowetting electrodes may vary. The cartridge includes a sample receiving port that includes an inlet 132 fluidly connected to a sample receiving chamber 134 through a first sample port channel 136. The biological sample is deposited into the inlet 132 and travels through the first sample port channel 136 into the receiving chamber 134 by way of capillary action. The sample receiving chamber 134 is fluidly connected to the main chamber 138 through a second sample port channel 140. The receiving chamber 134 and the second sample port channel 140 include a first electrowetting electrode 142 and a second electrowetting electrode 144. The electrowetting electrodes can be operated to controllably transfer the biological sample from the sample receiving chamber 134, through the second sample port channel 140, and into the main chamber 138. Optionally, the cartridge includes a filter between the inlet 132 and the main chamber 138, which may be positioned, for example, within the first sample port channel 136 or the second sample port channel 140. For example, if the filter is positioned in the second sample port channel 140, the electrowetting electrodes can be used to transfer the biological sample through the filter into the main chamber 138. The filter, if present, can remove larger debris in the biological sample.

The main chamber 138 includes a plurality of electrowetting electrodes, which are electrically connected to a device interface 146 so that the electrowetting electrodes can be operated using a device when connected to the device. The cartridge further includes a plurality of reagent reservoirs 148a, 148b, 148c, and 148d, which are fluidly connected to the main chamber 138 through reservoir channels 150a, 150b, 150c, and 150d. Although the exemplary cartridge illustrated in FIG. 1B shows four reagent reservoirs, it is understood that the cartridge can include any number of reservoirs, as determined by the test or tests to be performed using the cartridge. The reagent reservoirs 148a, 148b, 148c, and 148d and/or the reservoir channels 150a, 150b, 150c, and 150d can include one or more electrowetting electrodes, which can be used to transport reagent contained within the reagent reservoirs into the main chamber. For example, reagent reservoir 148a and reagent channel 150a can include a first electrowetting electrode 152a and a second electrowetting electrode 154a.

The biological sample and the reagents are transported into the mixing region of the main chamber 138, and are combined to form the processed biological sample. Optionally, the main chamber 138 of the cartridge can include a filter. The biological sample can be transported through the filter using the electrowetting electrodes, for example to separate components of the biological sample (for example to isolate serum from whole blood). The plurality of electrowetting electrodes can be operated to transport the processed biological sample, or a portion of the processed biological sample, to one or more sensors within the cartridge. Optionally, the biological sample is analyzed by a sensor without processing.

The exemplary cartridge illustrated in FIG. 1B includes two impedance sensors 156a and 156b, which are configured to measure an amount of a protein within the biological sample. The impedance sensors may be configured to perform the same assay (i.e., redundant impedance sensors) or different assays. Although the exemplary cartridge illustrated in FIG. 1B includes two impedance sensors, it is understood that the cartridge can include any number of impedance sensors, which may depend on the number of assays or assay redundancies for the particular cartridge. The illustrated cartridge further includes two channel sensors 158a and 158b, although other embodiments of the cartridge may have additional or fewer channel sensors, which may be redundant or non-redundant. The channel sensor may be, for example, a flow cytometer, or may be configured to detect or quantify a protein. The electrodes from the impedance sensors 156a and 156b, as well as the channel sensors 158a and 158b, are electrically connected to the device interface 146. When the device operates the cartridge, the device can transmit electrical current and/or receive acquired data through the electrically connected sensors.

The cartridge illustrated in FIG. 1B includes optical window 160, and optical window 162, which may be of the same size or of different sizes. The optical window includes a transparent window at the top of the cartridge and a transparent window at the bottom of the cartridge, which allows light to pass through. The optical windows are each fluidly connected to the main chamber 138 through a channel, and the biological sample can be transported to the optical windows using the electrowetting electrodes. When the cartridge engages the device (not shown in FIG. 1B), a light source and an optical detector are positioned on opposite sides of the optical windows, and the biological sample positioned in the optical window can be assayed using the device.

The cartridge illustrated in FIG. 1B further includes a waste reservoir 164 fluidly connected to the main chamber 138 through a waste channel 166. The waste reservoir 164 and the waste channel 166 include electrowetting electrodes so that the analyzed biological sample can be transported from the main chamber 138 into the waste reservoir.

The cartridges can be configured to include various numbers of sensors and/or sensor types, depending on the assay or assay panels the cartridge is used to perform. For example, the cartridge can include one or more of a channel sensor (e.g., a flow cytometer, or a channel sensor configured to detect an analytes such as a protein), an optical window, and/or an impedance sensor. The cartridge can be configured to perform one or more assays or assay panels, depending on the configuration, reagents, and/or sensors included in the cartridge. For example, the cartridge may be configured to assay one or more of a cell count (e.g., a red blood cell count, a white blood cell count, and/or a platelet count), or detection or quantification of a protein (or an enzyme) or other analyte (such as an electrolyte). In some embodiments, the cartridge is configured to test the biological sample for a complete blood count (CBC) or a comprehensive metabolic panel (CMP). In some embodiments, the cartridge is configured to detect or quantify one or more of glucose, calcium, blood urea nitrogen (BUN), creatinine, sodium, potassium, chloride, carbon dioxide, serum total protein, albumin, total bilirubin, alkaline phosphatase (ALP), aspartate amino transferase (AST), alanine amino transferase (ALT), red blood cells, white blood cells, platelets, hemoglobin, or hematocrit.

Device for Operating the Cartridge

The device is configured to interface with and operate the cartridge described herein to form a system for analyzing the biological sample. As discussed, the device can interface and operate different cartridge types that are configured to perform different assays or assay panels on the biological sample. The device includes a cartridge interface that engages the device interface on the cartridge to power and communicate with the cartridge. In this regard, the device is configured to supply power to the cartridge to power one or more sensors and/or electrowetting electrodes, to receive analytical data from the one or more sensors in the cartridge, and to operate the one or more sensors in the cartridge. The device can include a processor (such as a microcontroller, finite-state machine, etc.) and a memory, which can be used to operate device in controlling the electrowetting electrodes or one or more sensors, and to receive the analytical data. In some embodiments the device interface on the cartridge is configured to insert into the cartridge interface on the device, and in some embodiments the cartridge interface on the device is configured to insert into the device interface on the cartridge. The device may be a handheld device, which may be powered by battery.

The device can be configured to power and communicate with different types of cartridges to perform different analysis on biological samples. For example, the device can engage a first type of cartridge with a first sensor, analyze a first biological sample using the first type of cartridge, disengage the first type of cartridge, engage a second type of cartridge with a second sensor different from the first sensor, and analyze a second biological sample using the second type of cartridge. The device can be configured to power and operate 1, 2, 3, 4, 5, 6, 7, 8, 9, 10 or more different types of cartridges.

In some embodiments, the device includes one or more processors and a non-transitory computer-readable storage medium storing one or more programs configured to be executed by the one or more processors (such as a microcontroller). The one or more programs can include instructions for operating the plurality of electrowetting electrodes in the cartridge to transport the biological sample and/or mix the biological sample with one or more reagents. The one or more programs can also include instructions for operating the one or more sensors. As further described herein, certain sensors may utilize a static placement of the biological sample within the sensor, and certain sensors may require continuous flow of the biological sample through the sensor. Accordingly, in some embodiments, the one or more programs comprise instructions for operating the plurality of electrowetting electrodes in the cartridge to continuously transport the biological sample through the sensor or to statically position the biological sample within the sensor.

The device includes hardware and circuitry to power different device components, including the plurality of electrowetting electrodes and the one or more sensors. For example the device can include one or more power circuits that provide energy to various cartridge components to operate the cartridge components. In some embodiments, the device is configured to operate the plurality of electrowetting electrodes using about 0.5 volts to about 1000 volts (such as about 0.5 volts to about 1 volt, about 1 volt to about 5 volts, about 5 volts to about 10 volts, about 10 volts to about 20 volts, about 20 volts to about 30 volts, about 30 volts to about 50 volts, about 50 volts to about 100 volts, about 100 volts to about 250 volts, about 250 volts to about 500 volts, or about 500 volts to about 1000 volts). Preferably, the plurality of electrowetting electrodes is operated using about 50 volts or less, or more preferably about 20 volts or less. The lower voltage for actuating the biological sample using the plurality of electrowetting electrodes allows for lower power usage, which can allow for the device to be powered by battery.

The device further includes electronic circuitry and/or one or more programs to power, operate, and receive data from the one or more sensors. For example, the device can include an integrated circuit (e.g., a field-programmable gate array (FPGA) or an application-specific integrated circuit (ASIC)) to operate the sensor, which may include transmitting and/or receiving data using a data acquisition circuit (DAQ). The device may also include a digital signal processor (DSP) and/or a digital signal synthesizer (DSS).

The device may further include electronic circuitry to allow for information display or data export and/or communication. For example, the device may include an input/output port (I/O port) and/or wired or wireless communication device (such as WiFi or Bluetooth communication devices).

Figure 2:
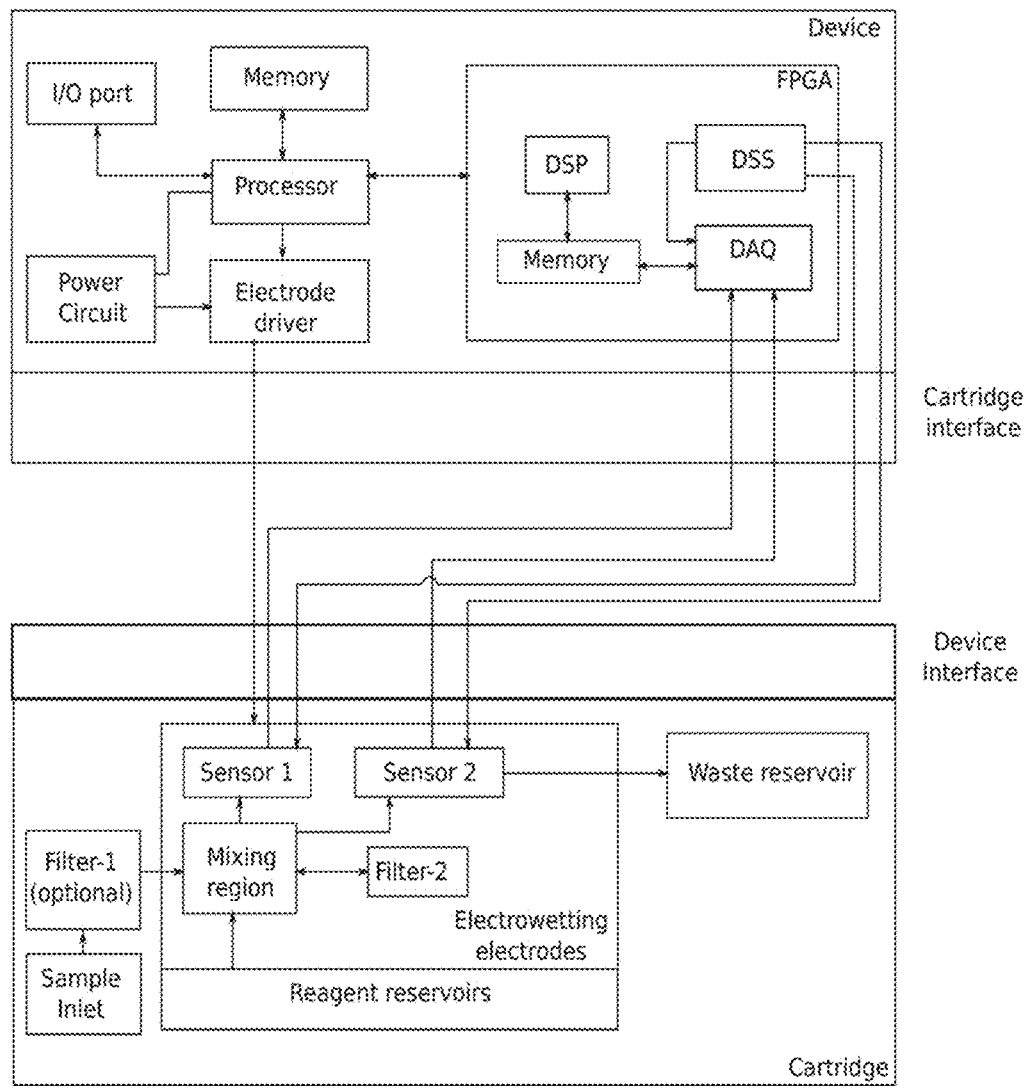
FIG. 2 illustrates a block diagram of an exemplary device engaged with a cartridge.

The device can interface with the cartridge as a system to analyze the biological sample. FIG. 2 illustrates a block diagram of an exemplary device engaged with a cartridge. The device includes a processor in electrical communication with a memory, which can store one or more programs for operating the device and/or cartridge. The device further includes a power circuit, which can include a battery or an electrical plug. The power circuit is in electrical communication with the processor to provide power to the processor, and in electrical communication with an electrowetting electrode driver. The power circuit may provide a different power to the processor and the electrode driver. For example, the power circuit may provide 3.3 volts (or any other suitable voltage) to the processor and between about 0.5 volts and about 1000 volts of power to the electrowetting electrode driver, depending on the configuration of the electrowetting electrodes. The processor is configured to operate the electrowetting electrode driver, which is in electrical communication with the electrowetting electrodes through the cartridge interface on the device and the device interface on the cartridge. The processor can operate the electrowetting driver, which controls electrowetting actuation of fluids (such as the biological sample and the one or more reagents) through the cartridge using the electrowetting electrodes. The electrowetting driver operates the electrowetting electrodes to transport the biological sample in the sample inlet to the mixing region of the cartridge. Further the electrowetting driver operates the electrowetting electrodes to transport reagents in the reagent reservoirs into the mixing region to combine the reagent(s) with the biological sample to form a processed biological sample. The electrowetting driver can then operate the electrowetting electrodes to transport to the processed biological sample to the sensor (or multiple sensors, e.g., sensor 1 and sensor 2, if present on the cartridge) either serially or alternatively (e.g., by splitting the samples), before transporting the processed biological sample to the waste reservoir.

Continuing to refer to FIG. 2, the processor of the device can be in electrical communication with an integrated circuit (e.g., a FPGA), which is configured to operate one or more sensors (e.g., Sensor 1 and Sensor 2). Sensor 1 may be, for example, a flow cytometer configured to count a number of cells or number of a type of cell in the biological sample, and Sensor 2 may be, for example, an impedance sensor configured to quantify a protein or analyte concentration. The device can include a digital signal synthesizer (DSS) module, which uses a direct digital synthesizer (DDS) and a digital to analog convertor (DAC) to generate and transmit analog signals (e.g., a multiplexed analog signal) to one or more sensors. Alternatively, this multiplexed signal can also be generated using a direct analog synthesizer (DAS), which does not require a DAC. As illustrated, the DSS is embedded in the FPGA, but it is conceived that the DSS could be separate from the FPGA. In each of the above two schemes using either a DDS or DAS, the analog or digital signals need to mixed after generation requiring a separate mixing stage to generate the multiplexed analog signal. In a separate embodiment, the signal is generated using an arbitrary waveform generator (AWG), where digital samples for the multiplexed signal stored in memory or a look up table (LUT) is converted to analog form using a variable frequency clock. Data from the sensors are transmitted to a data acquisition circuit (DAQ), which can store the data on a memory (which is optionally embedded in the FPGA) before being retrieved by a processor, such as a digital signal processor (DSP), for processing. The DSS may provide a reference signal to the DAQ circuit, which can be used to calibrate the signal received from the sensor. The DSP is optionally electrically connected to the device processor, and can transmit the data to the device processor. The device processor can store data in a device memory or output the data through an input/output (I/O) port to display or otherwise communicate the data (for example, through Bluetooth or network (e.g., WiFi connection). Optionally, the DSP can directly communicate with the I/O port to communicate the data.

The biological sample enters the cartridge through a sample inlet, and optionally passes through a first filter (Filter 1) before entering the main chamber of the cartridge. The optional filter can be used to prevent large debris from entering the chamber. The main chamber includes the electrowetting electrodes operated by the device, which can transport the biological sample to the mixing region of the chamber. The device may also operate the electrowetting electrodes to transport one or more reagents in the reagent reservoirs to mix with the biological sample in the mixing region. In some embodiments, a second filter (Filter 2) can be included, and the electrowetting electrodes operated by the device can transport the sample through the filter prior to transporting to the sample to one of the one or more sensors. The optional second filter can be used to separate components of the biological sample, for example to isolate blood serum or to separate red blood cells and platelets from white blood cells.

Sensors

The cartridge can include one or more sensors that can analyze the biological sample. In some embodiments, the electrowetting electrodes are configured to transport the biological sample to one or more sensors that analyze the biological sample. The sensors can transmit data to the device, which is electrically connected to the sensors through the device interface and the cartridge interface. The sensor or sensors in the cartridge may vary from cartridge type to cartridge type, depending on the desired biological sample analysis. Exemplary sensors include channel sensors and impedance-based sensors. Described herein are sensors for detecting an analyte (such as a protein, enzyme, or electrolyte), measuring an analyte concentration (such as a protein enzyme, or electrolyte concentration), or counting a number of cells or a number of a type of cell. However, other sensors may be used with the cartridge described herein.

Analyte Sensor

In some embodiments, the cartridge includes an optical window or an impendence senor configured to detect and/or quantify an analyte (such as a protein, enzyme, or electrolyte).

An optical sensor, which may be a component of the device that engages the cartridge, can be aligned with the optical window of the cartridge to assay the biological sample, for example to detect a protein or measure a protein concentration. The optical sensor can assay the biological sample using optical microscopy or spectroscopy, such as fluorescence, infrared (IR), Raman, or UV/Vis absorption, or any other suitable optical spectroscopy technique to generate analytical data. The data collected using spectroscopy can be analyzed by the device to determine whether the protein is present or the concentration of the protein. In some embodiments, the cartridge includes two or more optical windows, and at least one of the optical sensors can be used as a control. For example, a reagent without the biological sample can be analyzed by the control sensor, which provides a baseline for calibration. The device can then calibrate the received data to measure an accurate analyte concentration.

In some embodiments, the sensor is an impedance sensor, which is configured to detect an analyte (e.g., a protein, enzyme, or electrolyte) or measure an amount of the analyte. The impedance sensor can function independently (or with other impedance sensor) or in conjunction with one or more optical sensors. In some embodiments, when the optical sensor is used in combination with the electrical impedance-based sensor for analyte detection, the optical sensors can be used to detect interfering substances or to detect a calibration factor for the impedance measurement. The impedance sensor can include an electrode pair, wherein at least one of the two electrodes is functionalized with an affinity moiety that specifically binds to a target analyte. The electrodes may be coated with an insulating layer (i.e., a dielectric layer), and the affinity moiety may be functionalized on the insulating layer or an optional hydrophobic layer coating the insulating layer. The insulating layer preferably incudes a high-κ material (i.e., has a dielectric constant of about 3.9 or higher). In some embodiments, the insulating layer comprises silicon dioxide, silicon nitride, or silicon-oxy-nitride or a combination thereof (e.g., mixed together or in a plurality of separate layers). Characteristics (e.g., thickness, dielectric constant and/or hydrophobicity) of the insulating layer and/or hydrophobic layer may be the same or similar to the characteristics of the insulating layer and the hydrophobic layer described herein.

The affinity moiety may be, for example an antibody, an antibody fragment, or an aptamer (such as a DNA aptamer, an RNA aptamer, or an XNA aptamer). The biological sample can be transported to the sensor, and the target protein binds to the affinity moiety. In some embodiments, the affinity moiety specifically binds hemoglobin.

In some embodiments, the biological sample is statically positioned in the impedance sensor during an impedance measurement, and in some embodiments the biological sample continuously flows through the sensor during the impedance measurement. The amount of impedance change between the two electrodes resulting from binding of the target molecule to the affinity molecule is correlated with the concentration of the analyte in the biological sample. In some embodiments, the cartridge includes a reference sensor, which includes an electrode pair including at least one functionalized electrode configured in a manner similar to the sensor used to analyze the biological sample. A control fluid, such as a reagent without the biological sample, can be used to detect a baseline impendence, which can be transmitted to the device and used to calibrate the sensor used to analyze the biological sample.

In some embodiments, impedance is measured at a sampling rate of about 10 kHz or more (such as about 20 kHz or more, about 50 kHz or more, about 100 kHz or more, about 200 kHz or more, about 300 kHz or more, about 400 kHz or more, about 500 kHz or more, about 1 MHz or more, about 5 MHz or more, about 10 MHz or more, about 25 MHz or more, about 50 MHz or more, about 75 MHz or more, about 100 MHz or more, about 125 MHz or more, or about 150 MHz or more). In some embodiments, impedance is measured at a sampling rate of about 10 kHz to about 200 MHz (such as about 10 kHz to about 20 kHz, about 20 kHz to about 50 kHz, about 50 kHz to about 100 kHz, about 100 kHz to about 200 kHz, about 200 kHz to about 300 kHz, about 300 kHz to about 400 kHz, about 400 kHz to about 500 kHz, about 500 kHz to about 1 MHz, about 1 MHz to about 2 MHz, about 2 MHz to about 3 MHz, about 3 MHz to about 4 MHz, about 4 MHz to about 5 MHz, about 5 MHz to about 10 MHz, about 10 MHz to about 25 MHz, about 25 MHz to about 50 MHz, about 50 MHz to about 75 MHz, about 75 MHz to about 100 MHz, about 100 MHz to about 125 MHz, about 125 MHz to about 150 MHz, or about 150 MHz to about 200 MHz). In some embodiments, impedance is measured at a sampling rate of about 100 kHz to about 5 MHz. In some embodiments, impedance is measured at a sampling rate of about 125 MHz or more.

In some embodiments, impedance is measured at an excitation frequency of about 1 Hz or more (such as 10 Hz) or 100 Hz or more or 1 kHz or more, 10 kHz or more (such as about 20 kHz or more, about 50 kHz or more, about 100 kHz or more, about 200 kHz or more, about 300 kHz or more, about 400 kHz or more, about 500 kHz or more, about 1 MHz or more, about 5 MHz or more, about 10 MHz or more, about 25 MHz or more, about 50 MHz or more, about 75 MHz or more, about 100 MHz or more, about 125 MHz or more, or about 150 MHz or more). In some embodiments, impedance is measured at an excitation frequency of about 1 Hz to about 100 Hz or of about 100 Hz to about 1 kHz or of about 1 kHz to about 10 kHz or of about 10 kHz to about 200 MHz (such as about 10 kHz to about 20 kHz, about 20 kHz to about 50 kHz, about 50 kHz to about 100 kHz, about 100 kHz to about 200 kHz, about 200 kHz to about 300 kHz, about 300 kHz to about 400 kHz, about 400 kHz to about 500 kHz, about 500 kHz to about 1 MHz, about 1 MHz to about 2 MHz, about 2 MHz to about 3 MHz, about 3 MHz to about 4 MHz, about 4 MHz to about 5 MHz, about 5 MHz to about 10 MHz, about 10 MHz to about 25 MHz, about 25 MHz to about 50 MHz, about 50 MHz to about 75 MHz, about 75 MHz to about 100 MHz, about 100 MHz to about 125 MHz, about 125 MHz to about 150 MHz, or about 150 MHz to about 200 MHz). In some embodiments, impedance is measured at an applied excitation frequency of about 100 Hz to about 125 kHz. In some embodiments, impedance is measured at a sampling rate of about 125 kHz or more.

Figure 3:
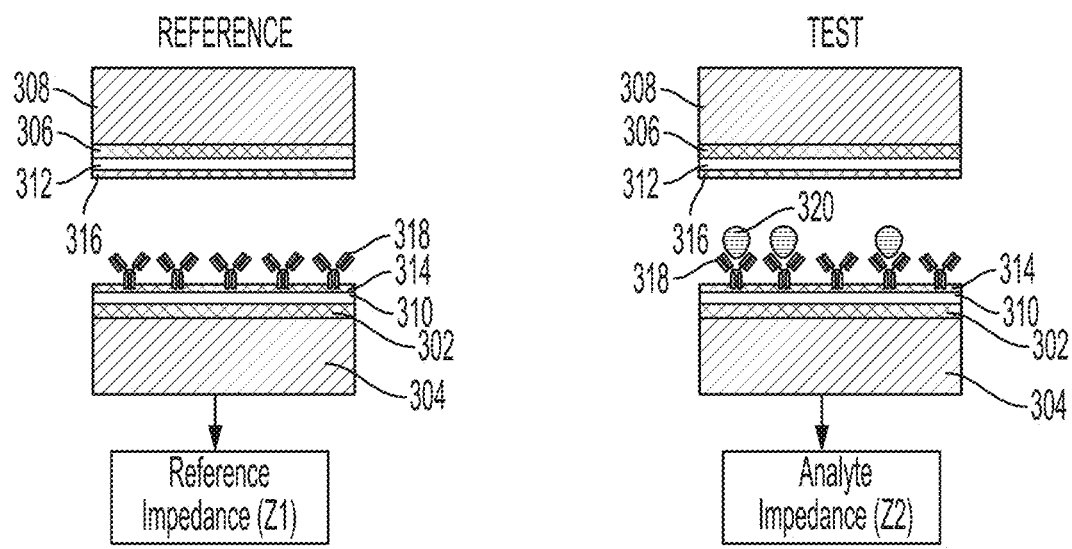
FIG. 3 illustrates an exemplary impedance sensor pair configured to measure the concentration of an analyte concentration.

FIG. 3 illustrates an exemplary impedance sensor pair configured to measure the concentration of an analyte concentration, such as a protein or enzyme concentration. The impedance sensor pair includes a test sensor and a control sensor. The biological sample is transported to the test sensor, and a control buffer is transported to the control sensor. Impedance is measured at the test sensor and the control sensor, and the impedance due to the analyte is the difference between the impedance measured at the test sensor and the control sensor. Both sensors include a first sensing electrode 302 on a bottom substrate 304, and a second sensing electrode 306 on a top substrate 308 opposite the first sensing electrode 302. The first sensing electrode 302 is coated with a first insulating layer 310, and the second sensing electrode 306 is coated with a second insulating layer 312. The first dielectric layer 310 is coated with a first hydrophobic layer 314, and the second dielectric layer 312 is coated with a second hydrophobic layer 316. The first hydrophobic layer 314 is functionalized with an affinity moiety 318, such as an antibody, which specifically binds to an analyte 320 in the biological sample in the test sensor. The first hydrophobic layer 314 of the reference sensor is also functionalized with an affinity moiety 318, but does not bind the analyte, as no biological sample is transported to the reference sensor. The second hydrophobic layer 316 in the illustrated sensors are not functionalized with the affinity moiety, although in other embodiments the second hydrophobic layer 316 may be functionalized. The biological sample is transported to the test sensor between the first sensing electrode 302 and the second sensing electrode 306, and the analyte impedance (Z2) can be measured. A control buffer is transported to the reference sensor, and the reference impedance (Z1) is measured. The difference between the analyte impedance (Z2) and the reference impedance (Z1) correlates with the concentration of the protein in the biological sample. The sensor is in electrical communication with the device interface of the cartridge. When the device interface of the cartridge is engaged with the cartridge interface on the device, the device can operate the impedance sensor to detect the change in impedance upon binding of the analyte to the affinity molecule or the reference impedance. The device can then determine the analyte concentration based on the detected impedances.

The biological sample is transported to the impedance sensor using the plurality of electrowetting electrodes. In some embodiments, the first sensing electrode (or the second sensing electrode) is positioned between two electrowetting electrodes in the plurality of electrowetting electrodes. In some embodiments, the first sensing electrode and/or the second sensing electrode is an electrowetting electrode within the plurality of electrowetting electrodes. In this configuration, the plurality of electrowetting electrodes can transport the biological sample to a position between the first sensing electrode and the second sensing electrode, and the first sensing electrode (or the second sensing electrode) can statically hold the biological sample in the sensor by activating the sensing electrode. A voltage switching circuit in or operated by the device is connected to the electrowetting electrodes, and can apply voltage to one of the electrodes to activate the electrode and attract the biological sample to position itself over the activated electrode. The voltage switching circuit is electrically connected to a switch configured to alternatively select between an impedance sensing circuit and an electrowetting electrode supply circuit. The impedance sensing circuit is configured to be electrically connected to the processor in the device when the cartridge is engaged with the device. The electrowetting supply circuit is configured to be electrically connected to the electrowetting electrode driver in the device when the cartridge is engaged with the device, and can supply electrical power to the electrowetting electrodes.

Figure 4A:
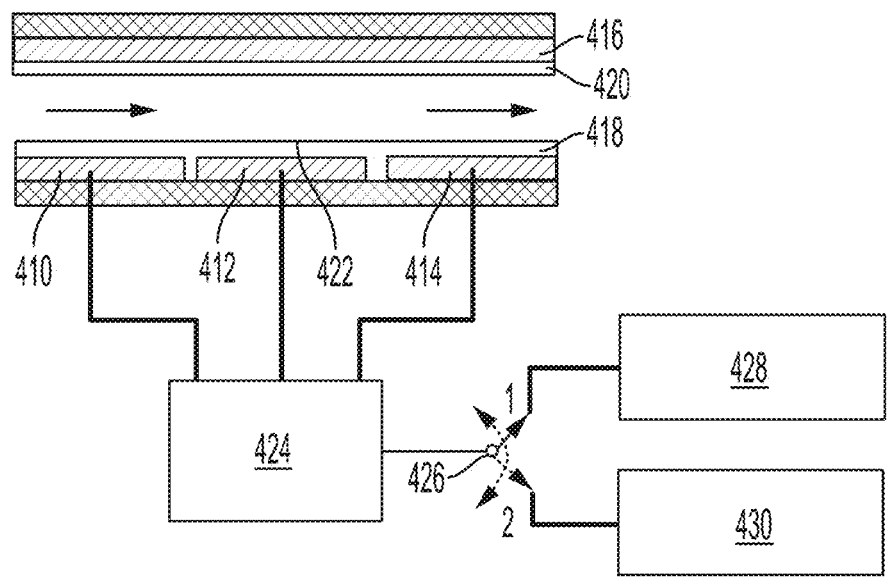
FIG. 4A illustrates an exemplary impedance sensor configured to detect or measure an analyte, integrated with a plurality of electrowetting electrodes.
Figure 4B:
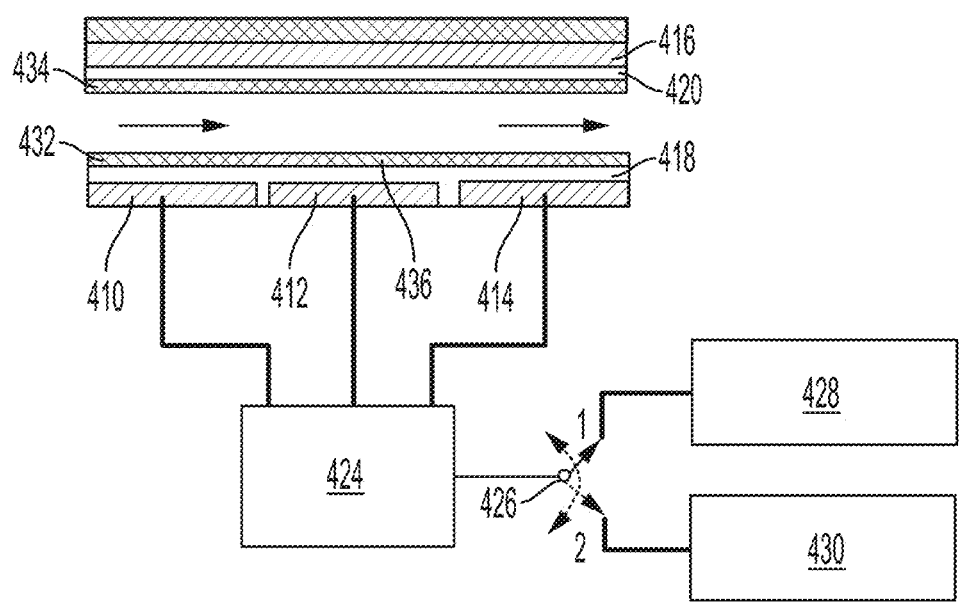
FIG. 4B illustrates the impedance sensor of FIG. 4A with a hydrophobic layer coating the insulating layers of the sensor.

FIG. 4A illustrates an exemplary impedance sensor configured to detect or measure an analyte (e.g., a protein, enzyme, or electrolyte) integrated with a plurality of electrowetting electrodes. The plurality of electrowetting electrodes includes a first electrowetting electrode 410, a first sensing electrode 412, and a second electrowetting electrode 414. Opposite the first electrowetting electrode 410, the first sensing electrode 412, and the second electrowetting electrode 414 is a second sensing electrode 416, which also acts as a ground electrode for the plurality of electrowetting electrodes. The first electrowetting electrode 410, the first sensing electrode 412, and the second electrowetting electrode 414 are coated with a first insulating layer 418, and the second sensing electrode 416 is coated with a second insulating layer 420. Although the second sensing electrode 416 is shown as a common electrode to electrodes 410, 412, and 414, it is contemplated that electrodes 410, 412, and 414 can opposite individual electrodes. At 422, a position above the first sensing electrode 412, the first insulating layer 418 is functionalized with an affinity moiety that specifically binds to a target analyte in the biological sample. The first electrowetting electrode 410, the first sensing electrode 412, and the second electrowetting electrode 414 are electrically connected to a voltage switching circuit 424. The voltage switching circuit 424 can selectively activate one or none of the first electrowetting electrode 410, the first sensing electrode 412, or the second electrowetting electrode 414 by applying a voltage to the selected electrode. The voltage switching circuit 424 is electrically connected to switch 426, which is configured to selectively connect the voltage switching circuit 424 to an impedance sensing circuit 428 or an electrowetting electrode supply circuit 430. The impedance sensor can optionally include a first hydrophobic layer 432 coating the first insulating layer 418 and/or a second hydrophobic layer 434 coating the second insulating layer 420 (see FIG. 4B). At a position 436 above the first sensing electrode 412, the first hydrophobic layer 432 is functionalized with the affinity moiety.

The biological sample can be transported to the first electrowetting electrode 410 by applying a voltage to the first electrowetting electrode 410. The voltage selection circuit 424 selects the first electrowetting electrode 410, and the switch 426 electrically connects the voltage selection circuit 424 to the electrowetting electrode supply circuit 430. With the biological sample positioned above the first electrowetting electrode 410, the voltage selection circuit 424 selects and applies a voltage to the first sensing electrode 412, thereby deactivating the first electrowetting electrode 410. By selecting the first sensing electrode 412, the biological sample is transported to the first sensing electrode 412, where it can be statically held so that target proteins within the biological sample can bind to the affinity moieties at 422. Switch 426 can electrically connect the impedance sensing circuit 428 to the voltage selection circuit 424, thereby allowing the change in impedance to be detected. The change in impedance may be in reference to a similar reference sensor that has a control solution rather than the biological sample. The concentration of the target analyte in the biological sample can then be determined based on the detected impedance. Once analysis of the biological sample is complete, the switch 426 can electrically connect to the electrowetting electrode supply circuit 430 to the voltage selection circuit 424, and the voltage selection circuit 424 can select the second electrowetting electrode 414 and deactivate the first sensing electrode 412, thereby transporting the biological sample out of the impedance sensor. The biological sample can then be analyzed by a different sensor or transported to the waste reservoir.

The impedance sensor for analyte detection or quantification may additionally or alternatively rely on an indirect analyte detection or quantification method. For an indirect measurement, the analyte (e.g., the protein, enzyme, or electrolyte) is bound to an affinity moiety, washed with a wash buffer, and bound to a second affinity moiety that can produce ions or protons (e.g., by catalyzing a compound to produce hydrogen peroxide, which can form protons). The ions or protons can be detected by an ion-sensitive or pH sensitive film, and the concentration of the ion or proton is proportional to the concentration of the analyte. Exemplary pH sensitive layers can include hafnium oxide, aluminum oxide, iridium oxide, or a chromium-tantalum oxide ($CrO_2$/$Ta_2O_3$). In some embodiments, the ions or protons are detected using a metal oxide semiconductor capacitor (MOSCap) sensor, which includes a pH-sensitive or ion-sensitive layer.

Figure 5A:
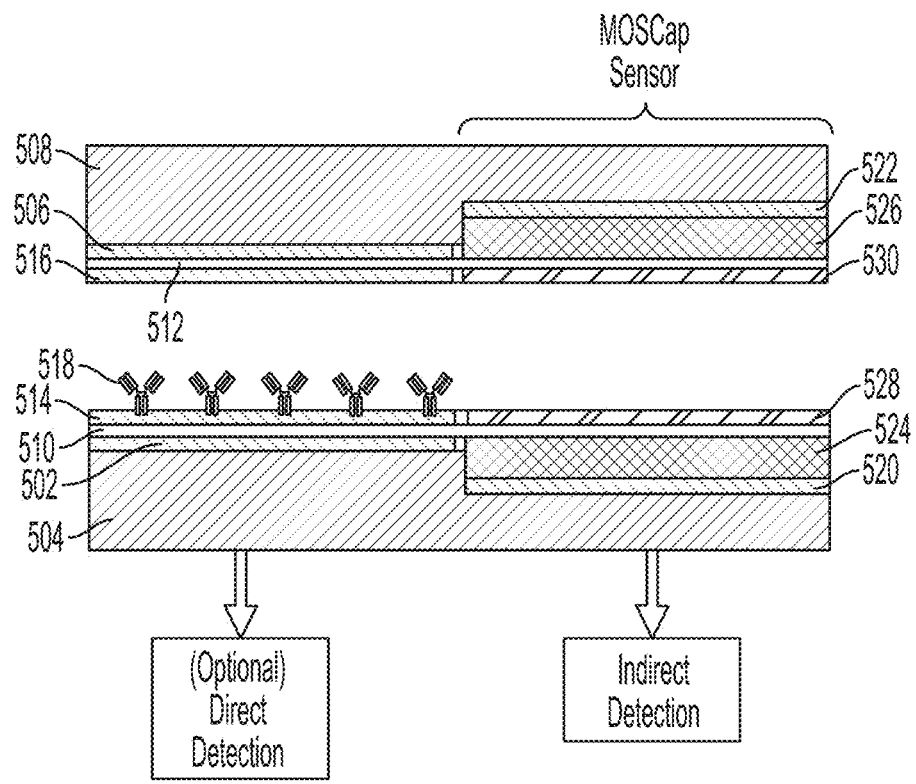
FIG. 5A illustrates an exemplary impedance sensor that can be used for indirect detection or quantification of an analyte. The impedance sensor includes a MOSCap sensor.

An exemplary impedance sensor that can be used for indirect detection or quantification of an analyte is shown in FIG. 5A. The impedance sensor illustrated in FIG. 5A includes a functionalized electrowetting electrode adjacent to a MOSCap sensor. The analyte is captured on the functionalized electrowetting electrode using affinity moieties, and a secondary affinity moiety is bound to the analyte to produce ions or protons that flow to the MOSCap sensor for detection. The electrowetting electrode includes a first electrowetting electrode 502 on a bottom substrate 504, and an optional second (ground) electrowetting electrode 506 on a top substrate 508 opposite the first electrode 502. The first electrowetting electrode 502 is coated with a first insulating layer 510, and the second electrowetting electrode 506 is coated with a second insulating layer 512. Optionally, the first insulating layer 510 is coated with a first hydrophobic layer 514 above the first electrowetting electrode 502, and the second insulating layer 512 is optionally coated with a second hydrophobic layer 516 below the second electrowetting electrode 506. However, the first hydrophobic layer 514 and the second hydrophobic layer 516 do not extend into the MOSCap sensor. The first hydrophobic layer 514 (or the dielectric layer 510 in an embodiment that omits the first hydrophobic layer) is functionalized with an affinity moiety 518. In some embodiments, the functionalized electrowetting electrodes are configured to directly detect or quantify analyte based on impedance change upon the analyte binding to the affinity moiety.

The MOSCap sensor includes a first MOSCap electrode 520 on the first substrate 504, and a second MOSCap electrode 522 on the second substrate 508 opposite the first MOSCap electrode 520. The first MOSCap electrode 520 is coated with a first semiconductor layer 524 (for example, silicon, germanium, or gallium compounds, such as gallium arsenide or gallium nitride), and the second MOSCap electrode 522 is coated with a second semiconductor layer 526. In this embodiment, 504 and 508 can be a different insulating or semiconducting material from 524 and 526, or the same insulating or semiconducting material. The first insulating layer 510 extends over the first semiconductor layer 524, and the second insulating layer 512 extends over the second semiconductor layer 526, although it is conceived that the insulating layers coating the semiconductor layers may be different than the insulating layers coating the electrowetting electrodes. A first detection layer 528 (e.g., a pH-sensitive layer or an ion-sensitive layer) coats the first insulating layer 510 within the MOSCap sensor, and a second detection layer 530 (e.g. a pH-sensitive layer or ion sensitive layer) coats the second insulating layer 512 within the MOSCap sensor.

Figure 5B:
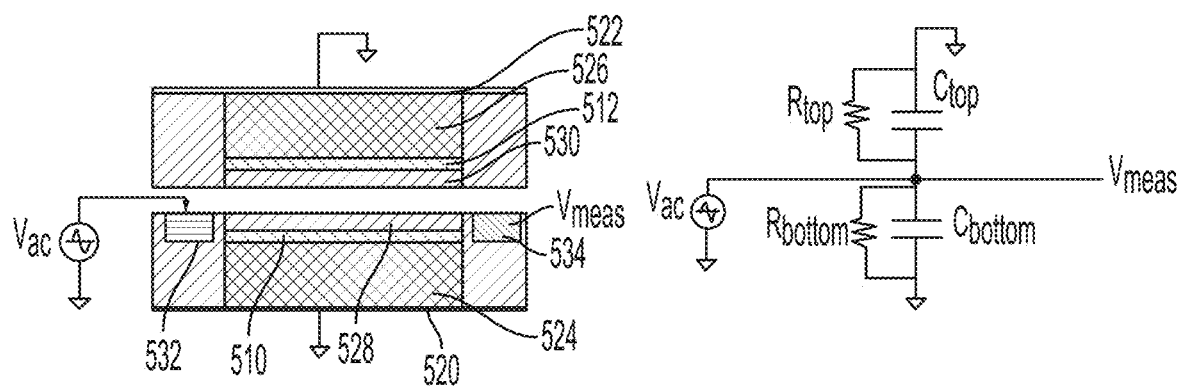
FIG. 5B shows a side view of the MOSCap sensor illustrated as part of the impedance sensor in FIG. 5A, along with an electrical model for the impedance sensor.

FIG. 5B shows a side view of the MOSCap sensor, along with an electrical model. The MOSCap sensor includes a reference electrode 532 (which may be, for example, a silver or silver chloride electrode, or may be of any other suitable material), and a counter electrode 534 (which may be, for example, gold or any other suitable material). In some embodiments, the reference electrode 532 and the counter electrode 534 are positioned in line with the liquid flow (e.g., the reference electrode 532 or the counter electrode 534 can be positioned between the first MOSCap electrode 520 and the first electrowetting electrode 502). In some embodiments, the reference electrode 532 and the counter electrode 534 are positioned adjacent to the liquid flow.

Figure 6:
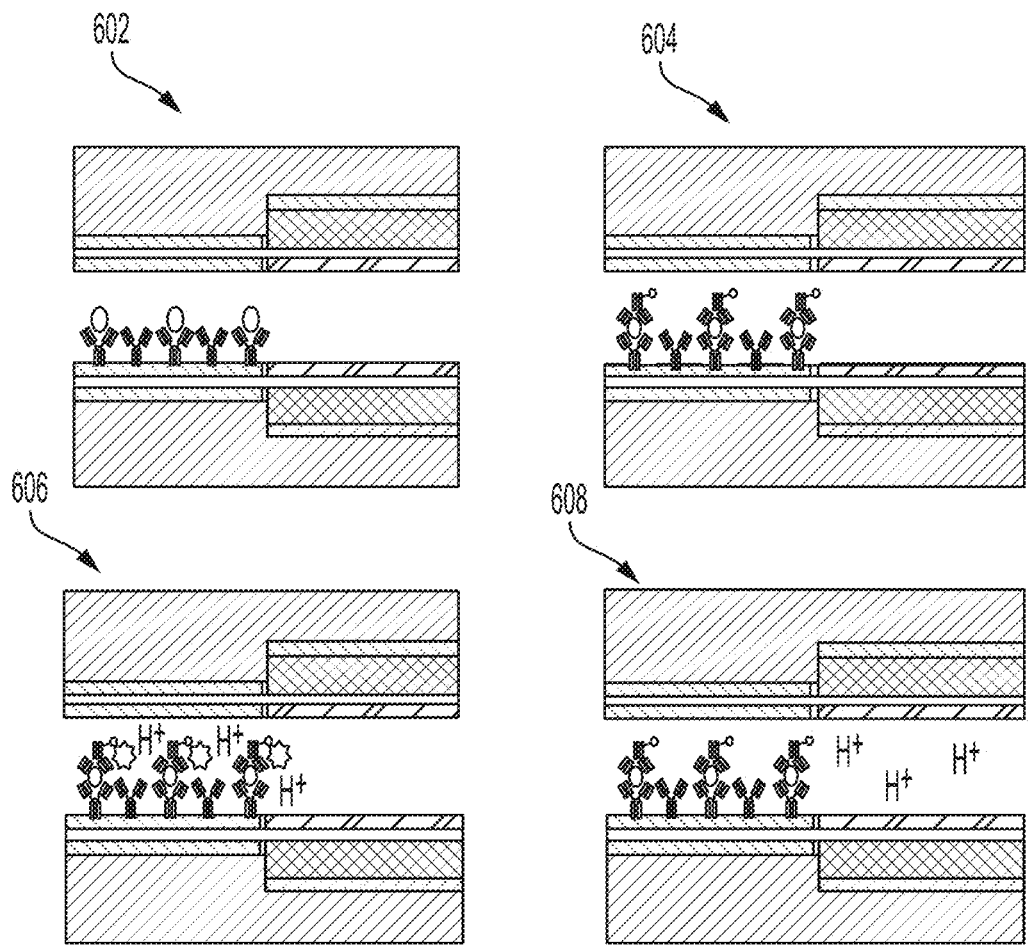
FIG. 6 illustrates direct and indirect analyte measurements using the sensor illustrated in FIGS. 5A and 5B.

FIG. 6 illustrates direct and indirect analyte measurements using the sensor illustrated in FIGS. 5A and 5B. At step 602, the biological sample is transported to the functionalized electrowetting electrodes through electrowetting actuation, and the analyte to be assayed binds to the affinity moiety attached to the hydrophobic layer (or the insulating layer, if no hydrophobic layer is present). Optionally the biological sample is washed once the analyte is bound. Once the analyte is bound to the affinity moieties, the impedance can be measured to directly measure the analyte concentration, as described above. At step 604, a secondary affinity moiety, which is conjugated to a signaling enzyme configured to produce protons, is transported to the functionalized electrowetting electrodes and binds the analyte bound to the primary affinity moiety attached to the electrowetting electrodes (via the insulating layer and/or hydrophobic layer). At step 606, a reagent is transported to the electrowetting electrodes, which can be catalyzed by the signaling enzyme to produce hydrogen peroxide, which degrades to produce protons. The protons flow to the MOSCap sensor at step 608, and the change in pH-sensitive layer modulates impedance in response to the protons. The modulated impedance is detected using the MOSCap sensor, and is proportional to the concentration of the analyte in the biological sample.

In some embodiments, the impedance sensor is a MOSCap sensor wherein one of the insulating layers (or hydrophobic layer coating the insulating layer, if present) is functionalized with an affinity moiety. The opposite insulating layer is coated with a pH-sensitive or ion-sensitive layer. This configuration of the MOSCap sensor allows for direct analyte detection or concentration measurement (through the functionalized surface) and indirect analyte detection (through the pH-sensitive or ion-sensitive layer) in the same MOSCap sensor.

Channel Sensors

The cartridge can additionally or alternatively include a channel sensor, which is configured to detect or quantify cells (or one or more types of cells) or an analyte (such as a protein or an enzyme) in the biological sample. In some embodiments, the one or more channel sensors in the cartridge include a flow cytometer. The flow cytometer can be configured, for example, to detect and distinguish between a plurality of different types of cells, such as red blood cells, platelets, and/or white blood cells (or one or more different types of white blood cells, such as eosinophils, basophils, neutrophils, monocytes, and/or lymphocytes). In some embodiments, the one or more channel sensors in the cartridge include a flow analyte sensor. In some embodiments, the one or more channel sensors can be configured as both a flow cytometer and a flow analyte sensor, and optionally includes a plurality of different electrode sets (which each contain 2, 3, or more electrodes) separately configured for functionality (i.e., to function as a flow cytometer or flow analyte sensor) within the same channel.

In some embodiments, the sample (e.g., the blood sample) is not processed (for example by mixing with one or more reagents) prior to being analyzed by the channel sensor (for example, to count and/or differentiate different cell types).

For example, whole blood (which may be but need not be diluted or processed) can be passed through the channel sensor to count or differentiate cells within the whole blood sample. In some embodiments, the sample is processed prior to analysis, for example by diluting the sample, labeling certain cell types, or lysing certain cell types (e.g., red blood cells) prior to analysis. In some embodiments, the sample is processed prior to analysis by only diluting the sample (i.e. no labelling or lysis is required) and no addition processing steps are needed prior to analysis. The sample may be processed, for example, by mixing the sample with one or more reagents.

The channel sensor is based on impedance sensing using the Coulter principle. Using the Coulter principle, a fluid filled micropore or microchannel (or nanopore or nanochannel) with paired impedance detection electrodes on either side of or within the micropore or microchannel (or nanopore or nanochannel) is able to detect impedance modulations due to a single particle (such as a cell) passing through the pore or channel. The change in resistance or low frequency impedance within the pore or channel is proportional to the size of the particle according to:

$$\frac{\Delta R_{ch}}{R_{ch}} \propto d^3$$

wherein $R_{ch}$ is the resistance of the channel or pore, $\Delta R_{ch}$ is the change in channel or pore resistance when a particle passes through the channel or pore, and d is the diameter of the particle. Multiplexed impedance fluctuation resulting from a particle, such as a cell, flowing through a pore or channel depends on various characteristics of the particle, such as the size of the particle, the structure of the particle, the composition of the particle, or surface characteristics of the particle. Impedance includes real and imaginary components, and one or both of the components may be analyzed to determine the type of cell generating the multiplexed impedance signal (i.e., an impedance signal at multiple frequencies). Alternatively, a magnitude component and a phase component of the multiplexed impedance, which can be measured and/or derived from the real and/or imaginary components, can be analyzed to determine the type of cell generating the multiplexed impedance signal (i.e., an impedance signal at multiple frequencies).

The channel sensor includes a channel containing a micropore or microchannel (or a nanopore or nanochannel) through which the biological sample (which is processed within the cartridge to dilute the sample and/or change the pH or electrolyte concentration of the surrounding buffer) can pass. The micropore or microchannel divides a first channel segment from a second channel segment, and the biological sample continuously flows through the full channel. The biological sample passes through the sensor by capillary action rather than electrowetting actuation, although the electrowetting electrodes may be used to introduce the biological sample into the channel sensor or withdraw the biological sample from the channel sensor. The channel sensor further includes an impedance detection electrode set (e.g., an impedance detection electrode pair) configured to apply an electrical current to the micropore or microchannel, and to detect impedance within the micropore or microchannel. The impedance detection electrodes are configured to be in contact with the liquid flowing through the channel sensor. For example, the impedance detection electrodes need not be separated from the sensor by an insulating layer (such as glass). Additionally, as further discussed herein, a multivariate analysis of detected electrical signal provides high resolution detection of different cell types. Therefore, reference electrodes are not needed for the channel sensor.

Figure 7:
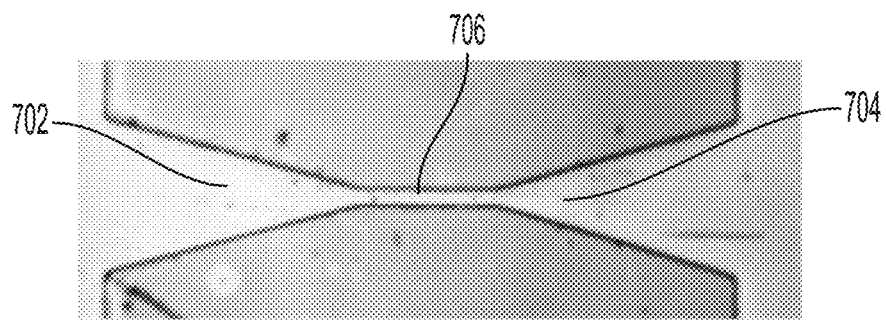
FIG. 7 shows an image of an exemplary channel of a channel sensor with a first channel segment, a second channel segment, and a microchannel between the first channel segment and the second channel segment.

FIG. 7 shows an image of an exemplary channel of a channel sensor with a first channel segment 702, a second channel segment 704, and a microchannel 706 between the first channel segment 702 and the second channel segment 704. The microchannel is 50 µm in diameter.

In some embodiments, the diameter of the micropore or microchannel (or nanopore or nanochannel) is about 10 nm to about 1 µm for analyte (e.g., protein) detection, or about 5 µm to about 100 µm for the flow cytometer. In some embodiments, the diameter of the micropore or microchannel (or nanopore or nanochannel) is about 5 nm to about 1 µm for analyte (e.g., protein) detection. For example, in some embodiments, the diameter of the nanopore or nanochannel for analyte detection may be between about 5 nm and about 10 nm, about 10 nm and about 20 nm, between about 20 nm and about 50 nm, between about 50 nm and about 100 nm, between about 100 nm and about 150 nm, or between about 150 nm and about 200 nm. In some embodiments, the flow cytometer includes a micropore or a microchannel with a diameter of about 5 µm to about 100 µm, such as about 5 µm to about 10 µm, about 10 µm to about 25 µm, about 25 µm to about 50 µm, or about 50 µm to about 100 µm. The size of diameter can be selected based on the desired analysis, and certain cell types may be more accurately counted using a different pore size. For example, platelets, with an average diameter of about 1-3 µm are preferably counted using a channel sensor having a micropore or a microchannel with a diameter of about 5 µm to about 25 µm, although lager diameters may be used for measurements. For white blood cells, the diameter of the micropore or microchannel is preferably about 40 µm to about 100 µm, such as about 50 µm.

The channel sensor can include two or more detection electrodes configured to detect impedance within the channel or pore (e.g., the microchannel or nanochannel, or micropore or nanopore). In some embodiments, the detection electrodes are configured to operate in pairs (e.g., a working electrode and a counter electrode). In some embodiments, the detection electrodes are configured to operate as a triad (e.g., a working electrode, a counter electrode, and a reference electrode). In some embodiments, the detections electrodes are statically positioned in sets of electrodes (e.g., a set of two or three electrodes) that operate to detect impedance. In some embodiments, the electrodes are dynamically grouped as a set (e.g., by the device operating the cartridge) to detect impedance. For example, the device can operate a switch that selects electrodes within a microchannel or nanochannel, and the selected electrodes are used to detect impedance. The electrodes may be selected, for example, based on a spacing of the electrodes and the type of analyte or cell being detected or measured.

The length of a microchannel is generally larger than the diameter of the microchannel Detecting electrodes may be placed within the microchannel, on the outer portions of the microchannel (i.e., with the microchannel in a space between the detecting electrodes), or both. In some embodiments, the length of the microchannel is about 0.001 mm or more in length, such as about 0.005 mm or more, about 0.01 mm or more, about 0.05 mm or more, about 0.1 mm or more, about 0.5 mm or more, about 1 mm or more, about 1.5 mm or more, about 2 mm or more, about 3 mm or more, or about 4 mm or more. In some embodiments, the length of the microchannel is about 5 mm in length or less, such as about 4 mm or less, about 3 mm or less, about 2 mm or less, about 1.5 mm or less, about 1 mm or less, about 0.5 mm or less, about 0.1 mm or less, about 0.05 mm or less, about 0.01 mm or less, or about 0.005 mm or less. In some embodiments, the length of the microchannel is about 0.001 mm to about 5 mm in length, such as about 0.001 mm to about 0.05 mm, about 0.05 mm to about 0.1 mm, about 0.1 mm to about 0.5 mm, about 0.5 mm to about 1 mm, about 1 mm to about 1.5 mm, about 1.5 mm to about 2 mm, about 2 mm to about 3 mm, about 3 mm to about 4 mm, or about 4 mm to about 5 mm in length. A channel (e.g., a microchannel or a nanochannel) can include a plurality of detection electrodes (e.g., two, three, four, five, six, seven, eight, nine, ten, or more) along the length of the channel, which are optionally grouped into two or more sets. Two or more electrode sets can be used to obtain redundant or different impedance measurements. Redundant impedance measurements may be taken, for example, to improve detection through signal averaging. Different impedance measurements may be dependent on different spacing of the electrodes, for example, which can improve detection sensitivity for measuring different cell types or sizes.

Spacing of the detection electrodes for measuring impedance can affect the detection sensitivity, depending on the size of the particle being measured. Narrower spaced electrodes are generally preferred for measuring smaller particles, whereas wider spacing of the electrodes allows for the measurement of larger particles. However, the electrodes should not be spaced so wide as to allow multiple particles between the electrodes to measure those same particles. For example, in some embodiments, detection electrodes are spaced by about 5 nm to about 100 nm (e.g., about 5 nm to about 10 nm, about 10 nm to about 25 nm, about 25 nm to about 50 nm, or about 50 nm to about 100 nm) to measure or detect an analyte (e.g., a protein, such as hemoglobin). In some embodiments, the detection electrodes are spaced by about 1 μm to about 5 μm (such as about 1 μm to about 1.5 μm, about 1.5 μm to about 2 μm, about 2 μm to about 3 μm, about 3 μm to about 4 μm, or about 4 μm to about 5 μm), for example to detect or measure platelets. In some embodiments, the detection electrodes are spaced by about 5 μm to about 10 μm (such as about 5 μm to about 6 μm, about 6 μm to about 7 μm, about 7 μm to about 8 μm, about 8 μm to about 9 μm, or about 9 μm to about 10 μm), for example to detect or measure red blood cells. In some embodiments, the detection electrodes are spaced by about 5 μm to about 25 μm (such as about 5 μm to about 10 μm, about 10 μm to about 15 μm, about 15 μm to about 20 μm, or about 20 μm to about 25 μm), for example to detect or measure white blood cells. Thus, by including differently spaced detection electrodes within the channel, the same channel can be used to detect different analytes and/or cell types.

In some embodiments, the geometry of the channel of the sensor is even or approximately even (i.e., the diameter of the channel is constant or approximately constant). In some embodiments, the geometry of the channel of the sensor is tapered (i.e., the diameter of the channel increases or decreases along the length of the channel). A tapered geometry of the channel allows a single flow to be analyzed at different positions along the length of the channel using different channel diameters. In some embodiments, the geometry of the channel of the sensor includes one or more waves (i.e., an increase in the diameter followed by a corresponding decrease in the diameter), and optionally one or of the detecting electrodes can be positioned within a wave.

Figure 8A:
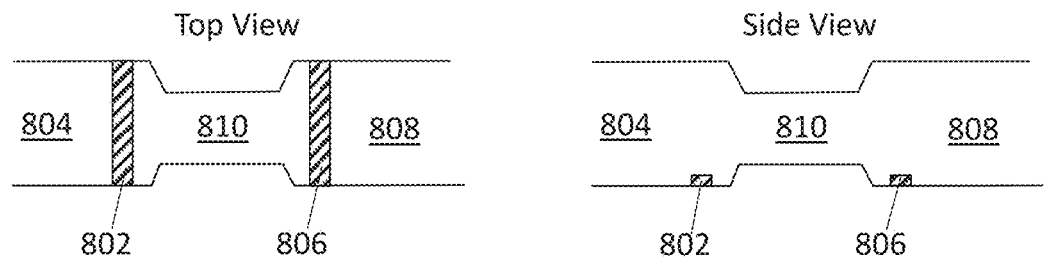
FIG. 8A illustrates a top view and a side view of a channel sensor with a first impedance detection electrode in the first channel segment, and a second impedance detection electrode in the second channel segment, with the micropore or microchannel between the first channel segment and the second channel segment.
Figure 8B:
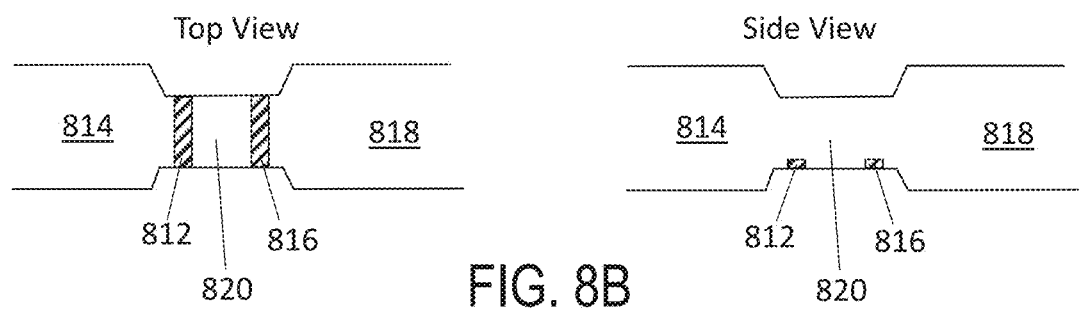
FIG. 8B illustrates a top view and a side view of a channel sensor with a first impedance detection electrode within the microchannel adjacent to a first channel segment, and a second impedance detection electrode within the microchannel adjacent to the second channel segment.
Figure 8C:
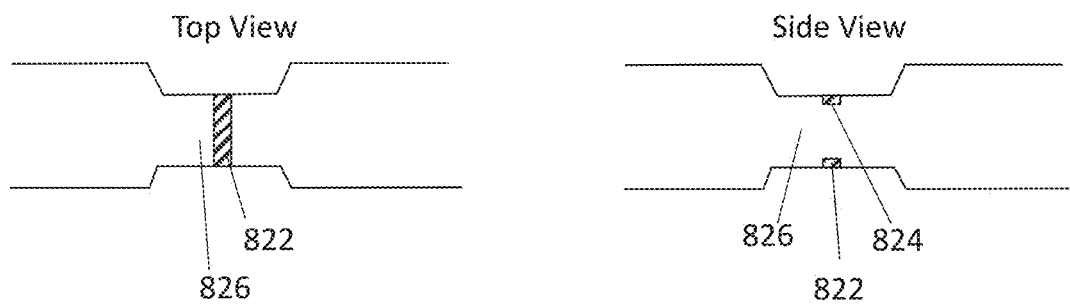
FIG. 8C illustrates a top view and a side view of a channel sensor that includes a first impedance detection electrode and a second impedance detection electrode positioned within a microchannel, with the first impedance detection electrode positioned above the second impedance detection electrode.

The impedance detection electrode pair can be located on either side of the micropore or microchannel (or nanopore or nanochannel), within the microchannel (or nanochannel) along the length of the microchannel (or nanochannel), or in a coplanar configuration within the micropore or microchannel (or nanopore or nanochannel). For example, FIG. 8A illustrates a top view and a side view of a channel sensor with a first impedance detection electrode 802 in the first channel segment 804 and a second impedance detection electrode 806 in the second channel segment 808, with the micropore or microchannel 810 between the first channel segment 804 and the second channel segment 808. In the illustrated embodiment, both the first impedance detection electrode 802 and the second impedance detection electrode 806 are positioned on the lower surface of the channel sensor, but it is conceived that the first impedance detection electrode 802 and the second impedance detection electrode 806 can be positioned on the upper surface of the channel sensor. FIG. 8B illustrates a top view and a side view of a channel sensor with a first impedance detection electrode 812 within the microchannel 820 adjacent to a first channel segment 814, and a second impedance detection electrode 816 within the microchannel adjacent to the second channel segment 818. In the illustrated embodiment, both the first impedance detection electrode 812 and the second impedance detection electrode 816 are positioned on the lower surface of the microchannel, but it is conceived that the first impedance detection electrode 812 and the second impedance detection electrode 816 can be positioned on the upper surface of the microchannel In FIG. 8C, the channel sensor includes a first impedance detection electrode 822 and a second impedance detection electrode 824 positioned within the microchannel 826 (or nanopore or nanochannel), with the first impedance detection electrode 822 positioned above the second impedance detection electrode 824 (that is, the first impedance detection electrode 822 is on the upper surface and the second impedance detection electrode 824 is on the lower surface, with the first impedance detection electrode 822 being aligned with the second impedance detection electrode 824).

Figure 8D:
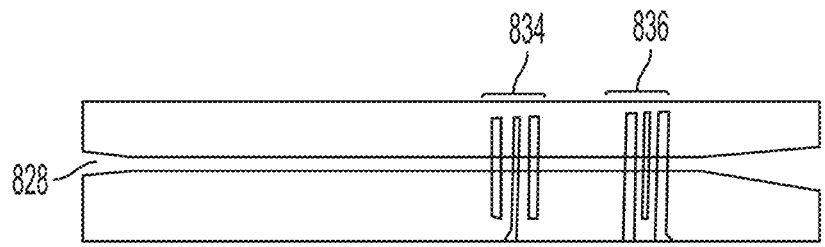
FIG. 8D shows an exemplary channel sensor with two sets of detection electrodes within the same channel.
Figure 8E:
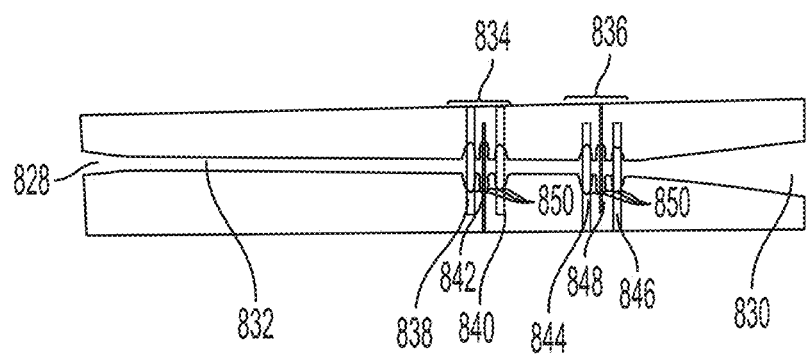
FIG. 8E shows another exemplary channel sensor with two sets of detection electrodes within the same channel, with wave-like channel features within the channel at each electrode position.

FIG. 8D shows an exemplary channel sensor with two sets of detection electrodes within the same channel. The sensor includes a first channel segment 828 and a second channel segment 830, separated by a channel (e.g., a microchannel) 832. The sensor includes a first set of detection electrodes 834 and a second set of detection electrodes 836 positioned along the length of the channel 832, and configured to measure impedance within the channel 832. The first set of detection electrodes 834 includes a working electrode 838, a counter electrode 840, and an optional reference electrode 842 positioned between the working electrode 838 and the counter electrode 840. Similarly, the second set of detection electrodes 836 includes a working electrode 844, a counter electrode 846, and an optional reference electrode 848 positioned between the working electrode 844 and the counter electrode 846. The spacing between the working electrode 838 and the counter electrode 840 in the first set of detection electrodes 834 is different from (and, in the illustrated example, larger than), the spacing between the working electrode 844 and the counter electrode 846 in the second set of detection electrodes 836. Thus, in the exemplary channel sensor illustrated in FIG. 8D, the first set of detection electrodes 834 is optimized to detect larger particles than the second set of detection electrodes 836. FIG. 8E shows an exemplary channel sensor similar to the channel sensor illustrated in FIG. 8D, except the channel 832 includes waves 850, and the electrodes are separately positioned within the waves. The diameter of the channel between the waves is narrower than the waves themselves.

Figure 8F:
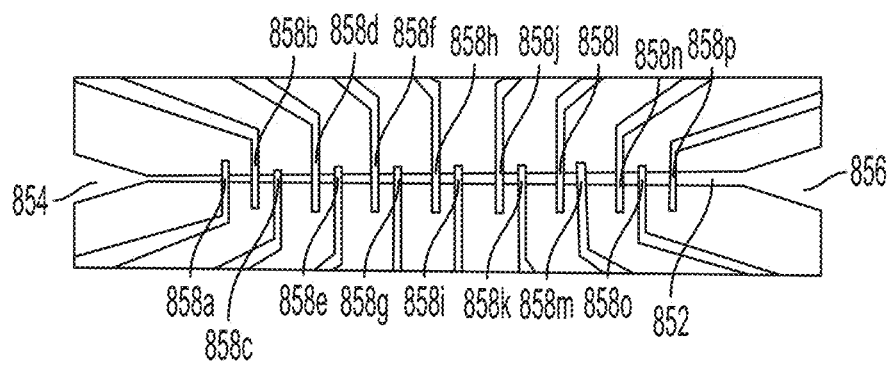
FIG. 8F shows an exemplary embodiment of a microchannel between a first channel segment and a second channel segment, with a plurality of detection electrodes positioned along the length of the channel.

FIG. 8F shows an exemplary embodiment of a microchannel 852 between a first channel segment 854 and a second channel segment 856, with a plurality of detection electrodes 858a-858p positioned along the length of the channel 852. In the illustrated example, the electrodes 858a-858ppp are evenly spaced, although in an alternative embodiments the electrodes are non-evenly spaced. Pairs of the electrodes can be dynamically selected to measure impedance.

In addition to the impedance detection electrodes, the channel sensor can optionally further include one or more flow detection electrode pairs and/or one or more isolation electrodes. The flow detection electrode pair can be positioned on either side of the micropore or microchannel (or nanopore or nanochannel), and is configured to detect liquid flow. In some embodiments, the sensor includes a first flow detection electrode pair on a first side of the micropore or microchannel (or nanopore or nanochannel) (that is, within the first channel segment), and a second flow detection electrode pair on a second side of the micropore or microchannel (or nanopore or nanochannel) (that is, within the second channel segment). The flow detection electrode pairs verify that the sensor is filled with liquid, such as a wash buffer, starting buffer, or other control reagent by applying a current (such as a DC current) and detecting voltage change (or applying a voltage and detecting a current change). Once the device verifies the sensor is filled with liquid by electrically communicating with the flow detection electrode pairs, the device can operate the electrowetting electrodes in the cartridge to transport the biological sample into the channel sensor.

A marker (such as an air bubble or a low conductivity solution) can be introduced to separate the control reagent from the biological sample. An air bubble marker can be introduced by interrupting liquid flow from the entrance of the channel sensor, for example by operating the electrowetting electrodes to stop liquid flow. Capillary action causes liquid within the channel to continue to flow through the channel sensor, and the bubble is generated. If the marker is an air bubble, a bubble trap can be included in the channel sensor to prevent the bubble from passing through the pore or channel. The bubble trap may include, a selective membrane that allows diffusion of air but not liquid. In some embodiments, the marker is an immiscible liquid, such as glycerol or an oil (e.g., silicon oil, vegetable oil, or olive oil). The liquid can then be introduced into the channel sensor, causing an air bubble to be positioned between the two fluid flows.

Detection of the marker then confirms the biological sample is being introduced into the channel sensor, and data acquisition is initiated. The marker can also be used to dynamically determine the flow rate of the liquid within the sensor, for example based on the volume of the marker and the start and end time points of the marker crossing the flow detection electrodes. Knowing the flow rate of the liquid in the channel sensor allows for quantification of particle (e.g., cell) concentration within the biological sample. Particle concentration is determined by number of particle passing in the unit time divided by the flow rate. Particle concentration can also or alternatively be obtained by dividing the total number of particles by the volume that is passed through the channel sensor. Peak width of the detected impedance signal is also a function of particle velocity through the channel, which can be calculated from flow rate and measured from the pulse width. The particle velocity allows for the determination of the translocation path of the particle through the channel based on pulse width variations in the detected signal. This allows for the application of error corrections to the magnitude of the signal measured, thereby allowing correction in signal intensity for a particle that pass through the channel away from the central axis of the channel. The variations would be more prominent for smaller particles passing through a channel. For example, if a 1-5 µm particle passes through a 50 µm channel, the particle can take several paths through the channel, either the center (indicative of the true magnitude) or the edge of the channel, which causes larger signal amplitude. Alternatively, the particle or cell can take a path between the center and edge of the channel resulting in increased amplitude between the two signal intensities.

The isolation electrodes can be positioned proximal to the entrance or the exit of the channel sensor, and function as ground electrodes. The ground (isolation) electrodes isolate the channel sensor from electrical activity from elsewhere in the cartridge, such as electrical activity resulting from operation of the electrowetting electrodes. The isolation electrodes therefore minimize electrical noise within the channel sensor.

FIG. 9 illustrates a top view and a side view of a channel sensor that includes a pair of impedance detection electrodes, two pairs of flow detection electrodes and two isolation electrodes. A first set of electrowetting electrodes 902 is adjacent to the entrance of the sensor so that an control reagent or the biological sample can be transported into the sensor, and a second set of electrowetting electrodes 904 is adjacent to the exit of the sensor so that the control reagent or the biological sample can be transported away from the sensor. Within the sensor, the control reagent or the biological sample is transported by capillary actuation. The sensor includes a micropore 906, with a first impedance detection electrode 908 and a second impedance detection electrode 910 on opposite sides of the micropore 906. Although the embodiment illustrated in FIG. 9 shows the impedance detection electrodes on either side of the micropore, other configurations are contemplated (see FIGS. 8A-8C). The sensor further includes a first pair of flow detection electrodes 912 and 914, and a second pair of flow detection electrodes 916 and 918 on either side of the micropore 906. The flow detection electrodes are positioned further form the micropore than the impedance detection electrodes. The sensor further includes a first isolation electrode 920 proximal to the entrance of the sensor, and a second isolation electrode 922 proximal to the exit of the sensor.

FIG. 10 shows initiation of operation of the channel sensor shown in FIG. 9, with the plot below demonstrating DC voltage detected by the first pair of flow detection electrodes 912 and 914. At initiation, electrowetting electrodes transport fluid (e.g., the control reagent) into the channel. Voltage detected by the flow detection electrodes at this first step is minimal, as no liquid is in contact with the electrodes. As the liquid enters the channel at the second step, the electrowetting transportation of the liquid into the sensor derives capillary flow through the sensor, which increases the voltage detected by the flow detection electrodes until the sensor is filled at the third step. A marker (such as an air bubble or a low conductivity buffer, relative to the control reagent) is introduced into the sensor, and separates the control reagent from the biological sample. Once the marker reaches the flow detection electrodes at the fourth step, voltage detected by the flow detection electrodes drops. The drop in voltage can signal to the device the introduction of the biological sample into the sensor, and data collection can be initiated.

The channel sensor may be used reused in a plurality of analytical cycles, for example to measure an analyte or cells under different conditions (e.g., different pH or electrolyte concentrations) or different dilutions. The different pH or electrolyte concentrations of the reagent surrounding the cells can modulate the surface charge of the cells, and different surface charge changes can be associated with different cell types. The biological sample can be divided into a plurality of sub-samples, which may be mixed with different reagents or different amounts of reagent (or serially diluted) within the cartridge, and one or more of the processed sub-samples can be cycled through the channel sensor. The sub-samples are separated by a control buffer, which may itself be separated from the sub-samples by a marker (such as an air bubble or a low conductivity buffer).

The biological sample may be diluted within the cartridge by mixing the biological sample with one or more reagents. In some embodiments, the biological sample is diluted to one or more different concentration before being assayed by the channel sensor, for example to about 0.00001× to less than 1× (such as about 0.00001× to about 0.0001×, about 0.0001× to about 0.001×, about 0.001× to about 0.01×, about 0.01× to about 0.1×, or about 0.1× to about less than 1×). The pH of divided biological samples can be adjusted within the cartridge so that the biological sample can assayed at one or more pH levels, such as between 3.0 and about 9.0 (for example, between about 3.0 and about 3.5, between about 3.5 and about 4.0, between about 4.0 and about 4.5, between about 4.5 and about 5.0, between about 5.0 and about 5.5, between about 5.5 and about 6.0, between about 6.0 and about 6.5, between about 6.5 and about 7.0, between about 7.0 and about 7.5, between about 7.5 and about 8.0, between about 8.0 and about 8.5, and/or between about 8.5 and about 9.0). In some embodiments, the pH of the assayed biological sample is 7.4. The cartridge can include several different reagents to adjust the pH of the biological sample, or can include two reagents that are mixed with the biological sample in a proportion to obtain the desired pH. In some embodiments, the biological sample is divided and processed to obtain 1 to 5 different sample concentrations at 1 to 10 different pH levels, for a total of about 1 to about 50 different biological sub-samples.

Figure 11:
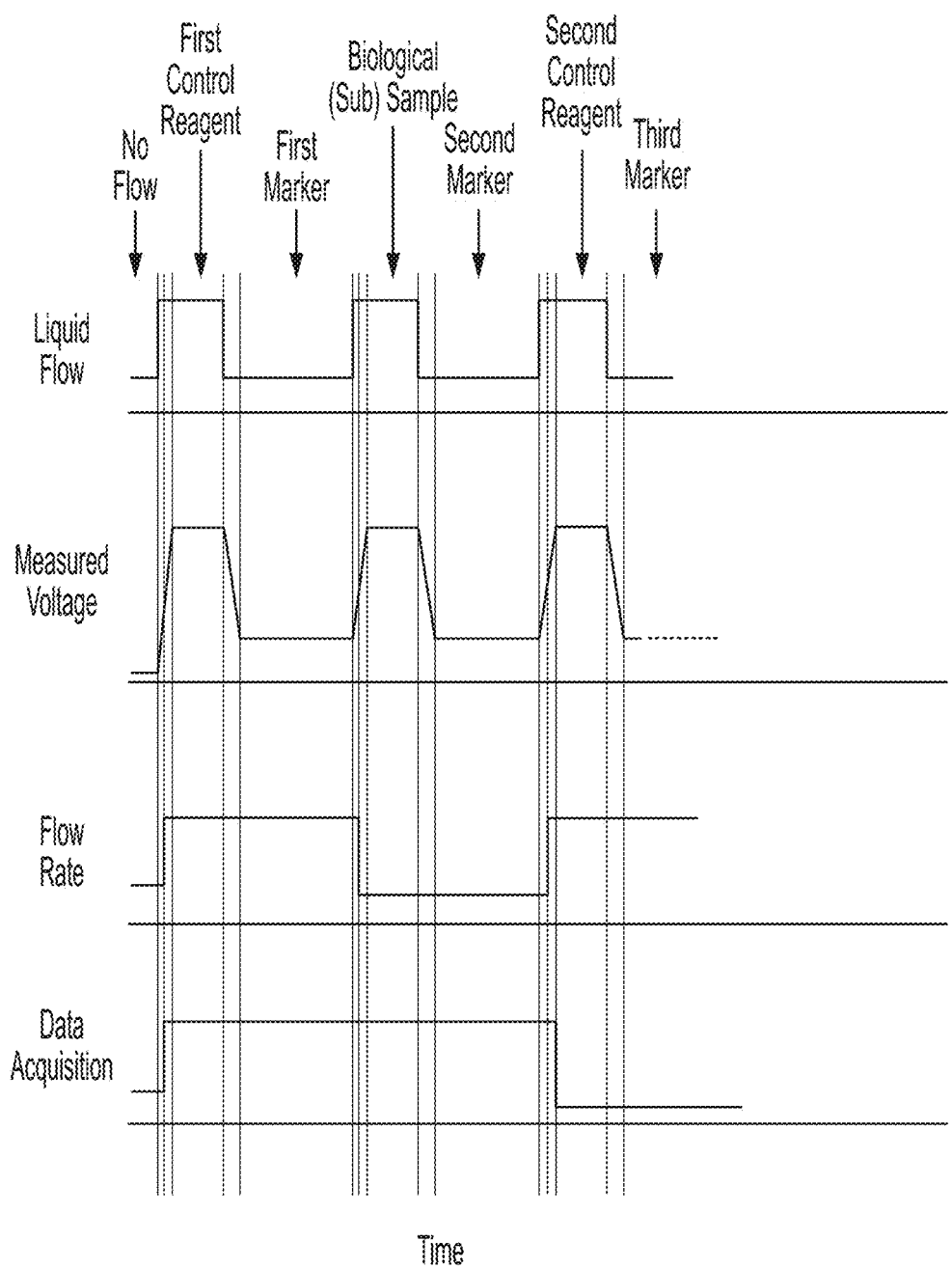
FIG. 11 illustrates how the marker is used as a trigger for data collection using the sensor, and the cycle can be repeated for the different biological sub-samples.

FIG. 11 illustrates how the marker is used as a trigger for data collection using the sensor, and the cycle can be repeated for the different biological sub-samples. Prior to introducing fluid into the channel sensor ("No Flow"), the liquid flow and flow rate are zero, with minimal or no voltage measured by the flow detection electrodes. As the control reagent is introduced into the channel sensor, the rate of liquid flowing through the sensor increases, and the voltage measured by the flow detection electrode pair near the sensor entrance increases as the control reagent flows across the flow detection electrode pair. As shown in FIG. 11, the increase in voltage detected by the flow detection electrode pair triggers data acquisition, although it is contemplated that the trigger for data acquisition could be detection of the first marker. The control reagent is separated from the biological sample (or biological sub-sample, if the sensor is used for multiple cycles to analyze multiple processed sub-samples) by a marker. The marker flows through the sensor and the liquid flow drops (assuming an air bubble marker). The marker passing over the flow detection electrodes causes the measured voltage to drop, as indicated in FIG. 11, until the biological sample enters the sensor. Entrance of the biological sample is detected by the flow detection electrodes, as marked by an increase in the measured voltage. The biological sample is followed by a second control reagent (which may be the same or different as the first control reagent), which may be separated from the biological sample by a second marker. The second marker flows through the channel sensor and the liquid flow drops (assuming the second marker is an air bubble). The marker is also detected by the flow detection electrodes by a drop in the measured voltage. The voltage drop caused by the marker, or detection of the passage of the marker, can optionally trigger a termination of data collection. As the second control reagent enters the sensor, the voltage measured by the flow detection electrodes increases until the next marker, which separates the second control reagent from the next cycle of biological sample, is detected. The cycle can then continue to repeat in this pattern until the desired number of cycles is reached.

Figure 12:
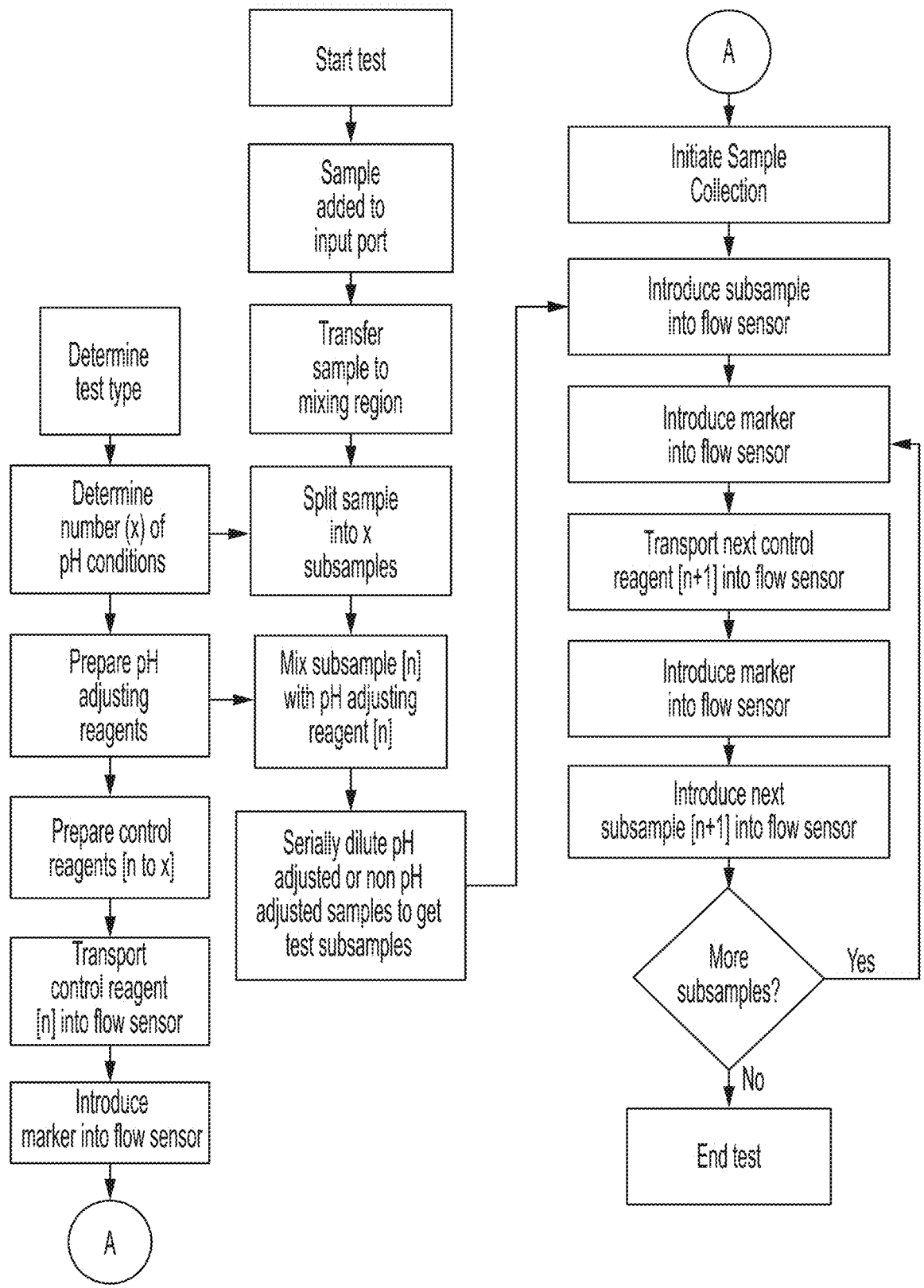
FIG. 12 illustrates an exemplary method of assaying a biological sample using the channel sensor in a cartridge.

FIG. 12 illustrates an exemplary method of assaying a biological sample using the channel sensor in a cartridge. The device can determine the test type to be performed based on the cartridge inserted into the device or by manual entry of the test type into the device. At the start of the test, the biological sample is added to the input port, and the sample is transferred to a mixing region through electrowetting actuation. Based on the test being conducted on the biological sample, the biological sample is processed to obtain a predetermined number of different pH conditions, and the biological sample is split into the number of different pH conditions. The pH adjusting reagents are prepared within the cartridge, for example by mixing a high pH component and a low pH component in predetermined proportions to obtain a desired number (x) of different pH adjusting reagents at the desired pH levels. The subsamples are then mixed with the pH adjusting reagents (that is, subsample [n] is mixed with pH adjusting reagent [n], subsample [n+1] is mixed with pH adjusting reagent [n+1], etc.). In some embodiments, a subsample is analyzed at an isotonic pH (7.4), and the pH of that subsample is not adjusted. The subsamples are then diluted (or serially diluted) to a desired concentration. Additionally, control reagents are prepared, which resemble the conditions of the processed biological subsamples without containing the biological sample (cells, analytes, etc.). A control reagent is prepared for each of the different pH conditions. The first control reagent (i.e., for subsample [n]) is transported into the channel sensor, followed by a marker (such as an air bubble or low conductivity fluid). The first subsample (i.e., subsample [n] at the desired concentration) is then transported into the channel sensor, followed by another marker and the next control reagent (or the same control reagent if the next subsample has the same reagent conditions with a different dilution factor). Another marker is introduced into the channel sensor, followed by the next subsample. This cycle is repeated until the subsamples are analyzed by the channel sensor.

Figure 13:
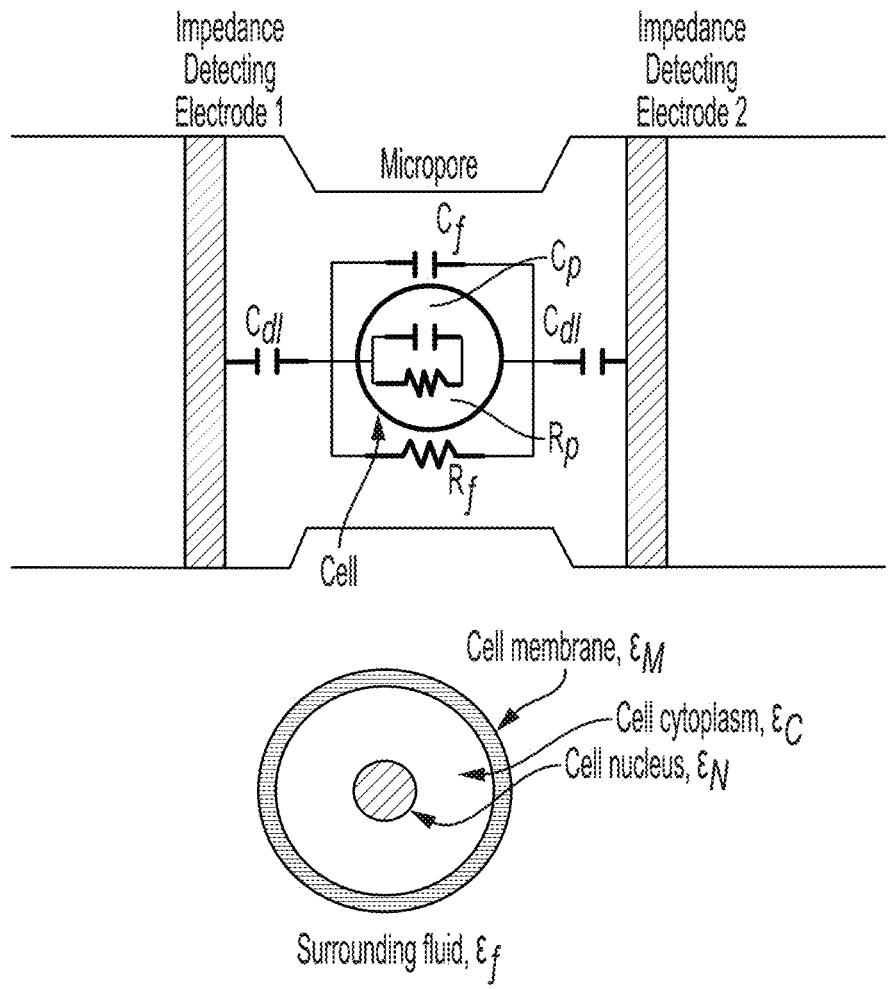
FIG. 13 illustrates an electrical model of a cell flowing through a pore or a channel.

In some embodiments, the channel sensor described herein is a flow cytometer, which is configured to detect a number of cells or a number of one or more types of cells (e.g., white blood cells, platelets, or red blood cells). An electrical model of a cell flowing through a pore or channel is shown in FIG. 13. In the model, $C_p$ refers to the capacitance from a combination of the cell membrane, the cell cytoplasm, and the cell nucleus; $R_p$ refers to resistance from the cell, and is indicative of cell volume; $C_f$ and $R_f$ refer to capacitance and resistance, respectively, of the fluid surrounding the cell, which can vary based on electrolyte concentration or pH of the fluid; and $C_{dl}$ refers to a double layer capacitance.

The flow cytometer can operate by applying multiplexed current and detecting a multiplexed impedance across a micropore or microchannel as a cell flows through the micropore or microchannel. The impedance at any given current frequency in the multiplexed current can include a real component and an imaginary component, and one or both of the impedance component can be analyzed at the different frequencies. Alternatively, the impedance at any given current frequency in the multiplexed current can include a magnitude component and a phase component, and one or both of the impedance component can be analyzed at the different frequencies. The flow cytometer channel sensor can be configured to distinguish between different types of cells in the biological sample. For example, the impedance to the multiplexed current can be used to differentiate between different types of cells in the biological sample, such as white blood cells, red blood cells and platelets. In some embodiments, the flow cytometer channel sensor can distinguish between eosinophils, basophils, neutrophils, monocytes, and lymphocytes. The different types of cells can be distinguished based on a unique impedance signature for each cell type, which can include a real and/or imaginary impedance component at a plurality of different current frequencies (e.g., 3, 4, 5, 6, 7, 8 or more different current frequencies). Alternatively, the different types of cells can be distinguished based on a unique impedance signature for each cell type, which can include a magnitude and phase impedance component at a plurality of different current frequencies (e.g., 3, 4, 5, 6, 7, 8 or more different current frequencies) either directly measured or derived from the measured real and imaginary impedance components. In some embodiments, the same electrode pair or different electrode pairs can be used to apply the current and measure impedance. With the flow cytometer design described herein, the cartridge need not separate different types of cells to obtain a cell count for each cell type.

The impedance detecting electrode pair is configured to simultaneously provide a multiplexed current through the micropore or microchannel and measure the voltage to determine impedance over a period of time as the biological sample flows through the sensor. The multiplexed current includes (1) a direct current component or a low-frequency alternating current, and (2) a plurality (e.g., 2, 3, 4, 5, 6, 7, 8 or more) of alternating current components at different frequencies. Preferably, the multiplexed current includes at least three alternating current components. In another preferred embodiment, the multiplexed current includes at least five alternating current components.

Impedance detected at the one or more frequencies can be used to differentiate the type of cell passing through the micropore or microchannel (e.g., a white blood cell, a red blood cell, or a platelet, or a particular type of white blood cell such as an eosinophil, a basophil, a neutrophil, a monocyte, or a lymphocyte). Different particle sizes, the presence or absence of a nucleus, and other cellular features can affect impedance at different current components. The direct current or low frequency current component can be used to determine different cell sizes. The direct current or low frequency current minimizes or eliminates the effect of the voltage drop at the electrode-electrolyte (from the surrounding liquid) interface, thereby minimizing the double layer capacitance in the electrical module. The resulting impact in impedance is related to particle (e.g., cell) size. A middle frequency alternating current relates to the partial cell capacitance influenced by the cell cytoplasm and cell membrane. A high frequency alternating current component can be used to characterize the cell cytoplasm and a nucleus (if present), and an ultra-high frequency alternating current relates to capacitance of the cell nucleus (if present). The multiplexed current can include additional frequencies to better distinguish the different cell types.

In some embodiments, the alternating current components comprises (1) a direct current or a low frequency alternating current at about 1 kHz to about 100 kHz (e.g., about 1 kHz to about 10 kHz, about 10 kHz to about 20 kHz, about 20 kHz to about 30 kHz, about 30 kHz to about 40 kHz, about 40 kHz to about 50 kHz, about 50 kHz to about 60 kHz, about 60 kHz to about 70 kHz, about 70 kHz to about 80 kHz, about 80 kHz to about 90 kHz, or about 90 kHz to about 100 kHz), (2) a medium frequency alternating current at about 100 kHz to about 700 kHz (such as about 100 kHz to about 200 kHz, about 200 kHz to about 300 kHz, about 300 kHz to about 400 kHz, about 400 kHz to about 500 kHz, about 500 kHz to about 600 kHz, about 600 kHz to about 700 kHz), (3) a high frequency alternating current of about 700 kHz to about 5 MHz (such as about 700 kHz to about 800 kHz, about 800 kHz to about 900 kHz, or about 900 kHz to about 1000 kHz, or about 1 MHz to about 2 MHz, about 2 MHz to about 3 MHz, about 3 MHz to about 4 MHz, or about 4 MHz to about 5 MHz), and (4) an ultra-high frequency alternating current of 5 MHz or more (such as about 5 MHz to 10 MHz, about 10 MHz to about 20 MHz, about 20 MHz to about 30 MHz, about 30 MHz to about 40 MHz, about 40 MHz to about 50 MHz, about 50 MHz to about 60 MHz, about 60 MHz to about 70 MHz, about 70 MHz to about 80 MHz, about 80 MHz to about 90 MHz, or about 90 MHz to about 100 MHz). In another embodiment, the multiplexed current includes (1) a direct current or an alternating current at about 1 kHz to about 100 kHz (e.g., about 1 kHz to about 10 kHz, about 10 kHz to about 20 kHz, about 20 kHz to about 30 kHz, about 30 kHz to about 40 kHz, about 40 kHz to about 50 kHz, about 50 kHz to about 60 kHz, about 60 kHz to about 70 kHz, about 70 kHz to about 80 kHz, about 80 kHz to about 90 kHz, or about 90 kHz to about 100 kHz), (2) an alternating current at about 50 kHz to about 250 kHz (such as about 50 kHz to about 70 kHz, about 70 kHz to about 90 kHz, about 90 kHz to about 110 kHz, about 110 kHz to about 130 kHz, about 130 kHz to about 150 kHz, about 150 kHz to about 200 kHz, or about 200 kHz to about 250 kHz), (3) an alternating current of about 250 kHz to about 700 kHz (such as about 250 kHz to about 300 kHz, about 300 kHz to about 350 kHz, about 350 kHz to about 400 kHz, about 400 kHz to about 500 kHz, about 500 kHz to about 600 kHz, or about 600 kHz to about 700 kHz; (4) an alternating current of about 700 kHz to about 5 MHz (such as about 700 kHz to about 800 kHz, about 800 kHz to about 900 kHz, or about 900 kHz to about 1 MHz, or about 1 MHz to about 2 MHz, about 2 MHz to about 3 MHz, about 3 MHz to about 4 MHz, or about 4 MHz to about 5 MHz), (5) an alternating current of about 5 MHz to about 20 MHz (such as about 5 MHz to about 10 MHz, about 10 MHz to about 15 MHz, or about 15 MHz to about 20 MHz), and (6) an alternating current of about 20 MHz or more (such as about 20 MHz to about 30 MHz, about 30 MHz to about 40 MHz, about 40 MHz to about 50 MHz, about 50 MHz to about 60 MHz, about 60 MHz to about 70 MHz, about 70 MHz to about 80 MHz, about 80 MHz to about 90 MHz, about 90 MHz to about 100 MHz, about 100 MHz to about 125 MHz, or about 125 MHz to about 150 MHz). In some embodiments, the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz. In some embodiments, the alternating current further comprises an additional alternating current at about 100 kHz or less, or about 50 kHz or less, which can be useful for determining the size of the cells. The frequency of the alternating current components may be selected based on salt concentration; channel or pore size; electrode size, spacing or material; or a specific cell to be counted.

In some embodiments, the multiplexed current is generated as analog current components and mixed in real time using the device before being transmitted to the impedance detecting electrodes in the cartridge. For example, the device can include a digital signal synthesizer (DSS) module, which uses a direct digital synthesizer (DDS) and a digital to analog convertor (DAC) to generate and transmit analog signals (e.g., a multiplexed analog signal). Alternatively, in some embodiments, the multiplexed current signal is generated using an arbitrary waveform generator (AWG), where digital samples for the multiplexed signal stored in memory or a look up table (LUT) is converted to analog form using a variable frequency clock.

Cells in the biological sample pass through the micropore or microchannel as impedance is measured by the impedance detection electrodes. In some embodiments, impedance is measured at a sampling rate of about 10 kHz or more (such as about 20 kHz or more, about 50 kHz or more, about 100 kHz or more, about 200 kHz or more, about 300 kHz or more, about 400 kHz or more, about 500 kHz or more, about 1 MHz or more, about 5 MHz or more, about 10 MHz or more, about 25 MHz or more, about 50 MHz or more, about 75 MHz or more, about 100 MHz or more, about 125 MHz or more, or about 150 MHz or more). In some embodiments, impedance is measured at a sampling rate of about 10 kHz to about 200 MHz (such as about 10 kHz to about 20 kHz, about 20 kHz to about 50 kHz, about 50 kHz to about 100 kHz, about 100 kHz to about 200 kHz, about 200 kHz to about 300 kHz, about 300 kHz to about 400 kHz, about 400 kHz to about 500 kHz, about 500 kHz to about 1 MHz, about 1 MHz to about 2 MHz, about 2 MHz to about 3 MHz, about 3 MHz to about 4 MHz, about 4 MHz to about 5 MHz, about 5 MHz to about 10 MHz, about 10 MHz to about 25 MHz, about 25 MHz to about 50 MHz, about 50 MHz to about 75 MHz, about 75 MHz to about 100 MHz, about 100 MHz to about 125 MHz, about 125 MHz to about 150 MHz, or about 150 MHz to about 200 MHz). Alternatively, in some embodiments, the measured signal is down sampled, thereby shifting the frequency response to lower frequencies and allowing digitizing the signal at lower sampling rates, for example when using an analog to digital converter (ADC). In some embodiments, impedance is measured at a sampling rate of about 100 kHz to about 5 MHz. In some embodiments, impedance is measured at a sampling rate of about 125 MHz or more.

Figure 14:
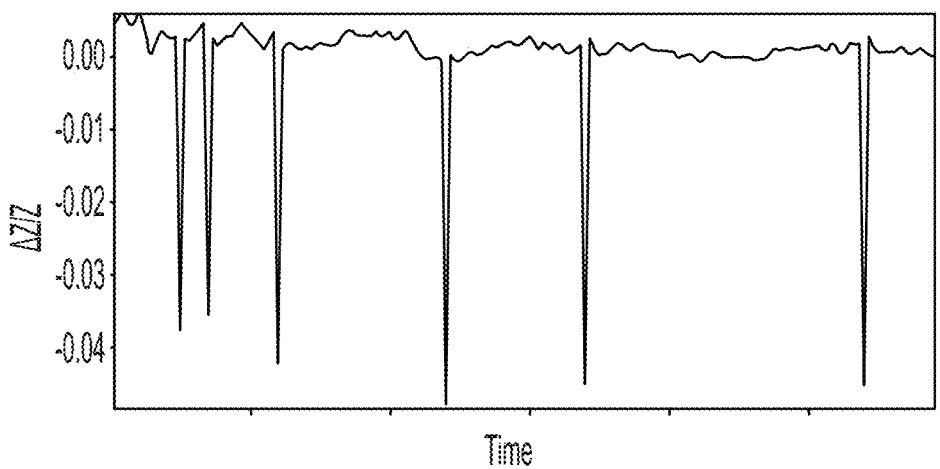
FIG. 14 presents an exemplary relative impedance change measured by impedance detecting electrodes as a function of time at a single frequency (30 kHz) for approximately 10 µm cells.

FIG. 14 presents an exemplary relative impedance change measured by impedance detecting electrodes as a function of time at a single frequency (30 kHz) for approximately 10 µm *Chlorella vulgaris* cells (bacteria-free, available from Carolina Biological Supply, NC, USA). Each downward peak corresponds to a particle passing through the microchannel, and various components of the impedance peak can be measured, such as peak height, peak width, peak area, and/or half-width peak height. A multivariate pattern is constructed from the plurality of current components to distinguish different types of cells. Change in impedance as a function of baseline impedance is measured, and one or more components of the impedance change can be used to describe the detected cells. Such components include, but are not limited to, one or more of impedance peak height, impedance peak width, impedance peak area, and impedance half-width height, which are indicative of cell size, surface charge, cell shape, and other distinguishing features of the cells. The biological samples can also be assayed at different concentrations or at different pH to further distinguish between cell types, as further discussed herein. Since the impedance components are affected by the isoelectric point and surface charge of the cells, the different cell types can be distinguished through a multivariate pattern. Unique multivariate patterns for different cell types can therefore include impedance peak height, impedance peak width, impedance peak area, and/or impedance half-width height, which may be determined at one or more pH levels and/or one or more electrolyte concentrations. In some embodiments, the multivariate pattern can include a real component and an imaginary component of the impedance, for example amplitude from a real component and amplitude from an imaginary component. In some embodiments, the multivariate pattern can include a magnitude component and a phase component of the impedance, for example amplitude from a magnitude component and amplitude from a phase component. The magnitude and phase components of the impedance can be directly measured, or can be derived from the real and imaginary components. Clustering algorithms can be used to create patterns for the various cell types based on the multivariate patterns collected at various frequencies. This can also be used to distinguish normal cell populations from abnormal cell populations.

By analyzing the multivariate pattern of detected impedance rather than only impedance amplitude, differentiation of different cell types is more accurate. For example, the channel sensor need not include a reference electrode to control for impedance variations. Additionally, the flow censor can be used to assay cell counts and/or analyte concentration using a whole blood biological sample, rather than analyzing separated components of the biological sample (e.g., serum, plasma, etc.) or labeled cells.

In some embodiments of the flow cytometer channel sensor, impedance signal is analyzed for a real component and an imaginary component. The multivariate pattern of the real component and a multivariate pattern of the imaginary component of the multiplexed impedance, for example, can be used to distinguish cell types. In some embodiments, the amplitude of a real component and the amplitude of an imaginary component of the multiplexed impedance is used to distinguish the different cell types. In some embodiments of the flow cytometer channel sensor, impedance signal is analyzed for a magnitude component and a phase component. The multivariate pattern of the magnitude component and a multivariate pattern of the phase component of the multiplexed impedance, for example, can be used to distinguish cell types. In some embodiments, the amplitude of a magnitude component and the amplitude of a phase component of the multiplexed impedance is used to distinguish the different cell types. The number of different current frequencies for the multiplexed impedance may be 3, 4, 5, 6, 7, 8, or more different current frequencies.

The detected multiplexed impedance from the flow cytometer channel sensor can be filtered and demodulated to isolate each frequency using a filter (e.g., a bandpass filter). This can be done, for example, by the device that operates the cartridge. A processor can analyze the multiplexed impedance signal for each cell that passes through the flow cytometer channel sensor and label or count the individual cell. This can be done, for example, using a trained machine learning model. The machine learning model can be trained using known impedance signatures for the various cell types. Exemplary machine learning models include naïve Bayes classifiers, logistic regression, decision tree models, gradient boosted trees, support vector machines, neural networks and other deep learning algorithms In some embodiments, the machine learning model is trained using a supervised or a semi-supervised method.

In one example, unlabeled impedance signatures from particles or cells in a sample (e.g., whole blood) are used to refine a model by semi-supervised learning, which can include applying self-training to generate clusters that characterize the different particle/cell types in the sample. The generated data set is compared against the baseline data sets. The error in the unlabeled data sets is used to calculate calibration weights for each cell type. In addition to using repeat testing of single cell types from different sources, mixed cell types of known types and whole blood samples can be used to adjust baseline weights that correct for the model's cluster fits for each cells type taking into account patient demographic information such as age, sex, ethnicity etc. For example, the model can establish clusters that differential white blood cells, red blood cells, and/or platelets. In some embodiments, the clusters differentiate within the white blood cells, for example to distinguish between two or more of neutrophils, basophils, eosinophils, monocytes, and/or lymphocytes. The clusters can be validated, for example, by a goodness of fit of one or more generative models (e.g., a Gaussian mixture model). Another calibration factor can correct for count errors when using the total counting using a known method such as a commercial hematology analyzer.

The cartridge may additionally or alternatively include one or more channel sensors that are configured to measure an analyte (e.g., a protein or enzyme) concentration. The pore size for the channel sensors configured to measure an analyte concentration is generally smaller than the pore sized used for the flow cytometer due to the smaller size of the particles, although a similar Coulter principle can be applied. The biological sample or subsample may be filtered prior to being transported to the channel sensor, as cells in the biological sample may clog the nanopore or nanochannel Before introducing the biological sample (or subsample) into the channel sensor, the biological sample (or subsample) is mixed with a reagent containing a charged affinity moiety, (which may comprise, for example, an antibody, an antibody fragment, or an aptamer), which specifically binds the target analyte. In some embodiments, the affinity molecule is a multivalent affinity molecule (for example, bivalent, trivalent, or tetravalent). The charged affinity moiety bound to the target analyte increases the electrical field modulation compared to the target analyte alone when passing through the nanopore or nanochannel, thereby increasing the impedance signal.

In some embodiments analyzing the biological sample using the channel sensor configured to measure an analyte concentration, the affinity molecule (which can include, for example, the aptamer, or antibody or fragment thereof) is bound to a multivalent tag, such as a protein or a nanoparticle. In some embodiments, the multivalent tag is a bivalent tag, a trivalent tag, or a tetravalent tag. For example, in some embodiments, the multivalent tag is avidin or an avidin derivative (e.g., neutravidin or streptavidin), which can bind to a biotin moiety fused to the affinity molecule. For example, in some embodiments, the affinity molecule is an aptamer with a biotin moiety attached (optionally, through a linker) to the 5' or 3' end of the aptamer, and the multivalent tag is an avidin. By using the multivalent tag, the impedance signal is increased compared to use of the affinity molecule alone.

Affinity moieties bound to the target analyte can be distinguished from unbound affinity moieties based on a change in impedance, and the number of bound affinity moieties can be used to determine the concentration of the target analyte in the biological sample. In some embodiments, a change in impedance amplitude is used to distinguish bound affinity moieties from unbound affinity moieties. In some embodiments, a multivariate pattern is constructed from the plurality of current components to distinguish bound and unbound affinity moieties. Change in impedance as a function of baseline impedance is measured, and one or more components of the impedance change can be used to describe the state of the affinity moiety (bound or unbound). Such components include, but are not limited to, one or more of impedance peak height, impedance peak width, impedance peak area, and impedance half-width height.

Figure 15A:
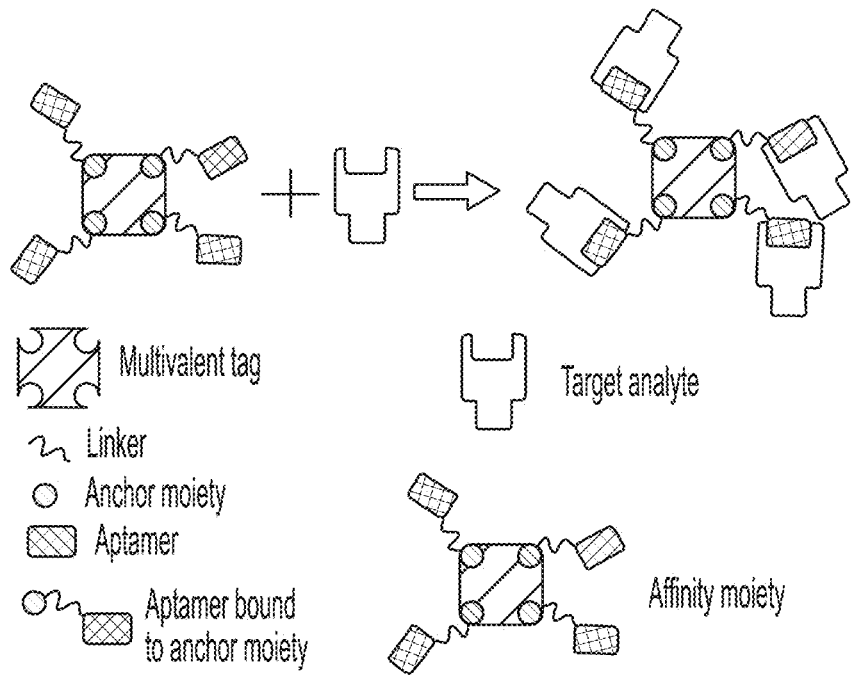
FIG. 15A illustrates target analyte binding to a tetravalent affinity molecule.

FIG. 15A illustrates target analyte binding to a tetravalent affinity molecule. The biological sample (which may be processed by mixing the biological sample with one or more reagents and/or filtered within the cartridge) is mixed with a reagent comprising the tetravalent affinity molecule. The tetravalent affinity molecule includes a tetravalent tag (e.g., an avidin or avidin derivative) bound to four aptamer molecules. The aptamer molecules are bound to a biotin moiety through a linker sequence, and an anchor moiety (e.g., biotin) binds the tetravalent tag. When the affinity molecule is mixed with the target analyte, up to four target analyte molecules bind the tetravalent affinity molecule.

Figure 15B:
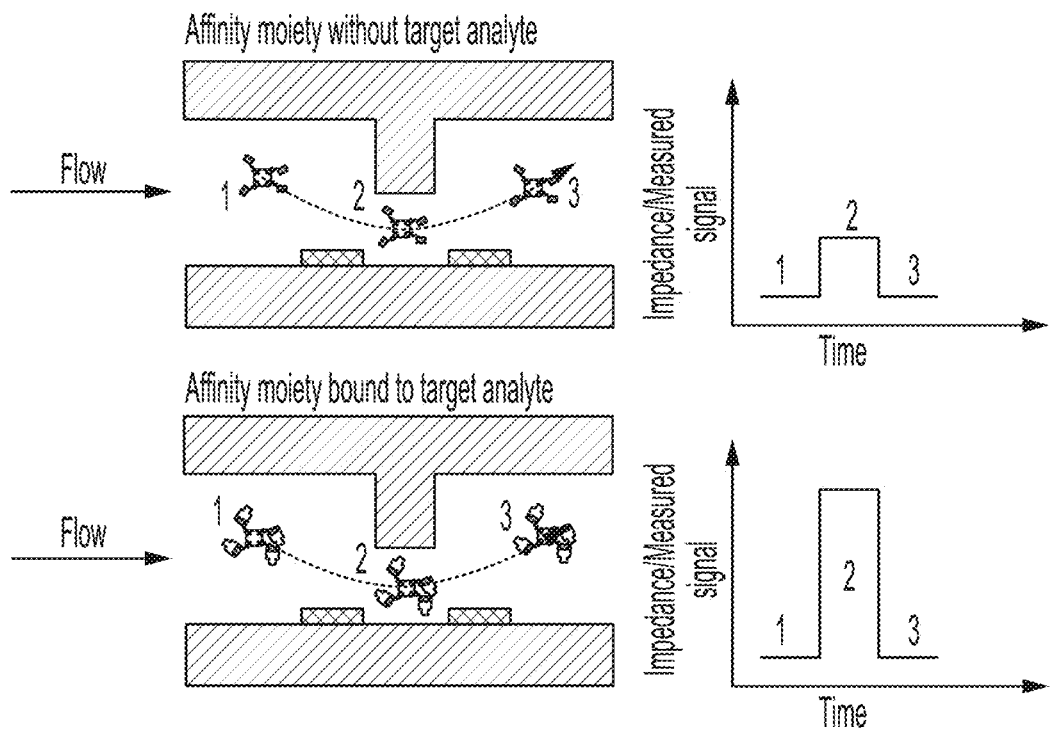
FIG. 15B illustrates the impedance change resulting from an affinity moiety that is not bound to the target analyte (top panel) and the impedance change resulting from an affinity moiety that is bound to the target analyte (bottom panel) as the affinity moiety passes through the nanochannel of the channel sensor.

FIG. 15B illustrates the impedance change resulting from an affinity moiety that is not bound to the target analyte (top panel) and the impedance change resulting from an affinity moiety that is bound to the target analyte (bottom panel) as the affinity moiety passes through the nanopore or nanochannel of the channel sensor. As indicated at step 2, impedance signal can be detected in both circumstances, but the impedance signal has greater amplitude when the affinity moiety is bound to the target analyte. Although the figure illustrates only a change in impedance magnitude, a multivariate pattern difference can be detected between the two instances. In some embodiments, the impedance magnitude is analyzed to determine an analyte concentration in the biological sample. In some embodiments, the multivariate patter is analyzed to determine the analyte concentration in the biological sample. The multivariate pattern can include characteristics of the detected impedance peak, such as impedance peak height, impedance peak width, peak area, and/or half-width peak height.

Figure 15C:
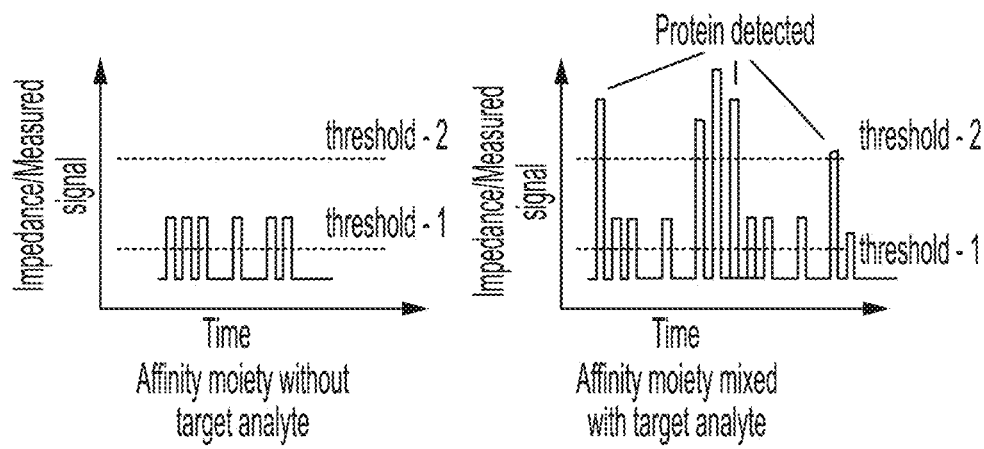
FIG. 15C illustrates one example of using impedance magnitude to determine the concentration of the target analyte.

FIG. 15C illustrates one example of using impedance magnitude to determine the concentration of the target analyte. Two impedance signal thresholds can be established. If an impedance signal crosses the lower threshold but not the upper threshold, it is determined that the affinity moiety passing through the nanopore or nanochannel is not bound to the target analyte. If the impedance signal crosses both the lower threshold and the upper threshold, it is determined that the affinity moiety passing through the nanopore or the nanochannel is bound to the target analyte. The proportion of bound affinity moieties can be used to determine the analyte concentration in the biological sample.

The channel sensor (e.g., the flow cytometer or the channel sensor configured to measure an analyte concentration) can be calibrated using particles having standardized sizes, surface charge, and/or material. The calibration can be done during the manufacturing process, and allows for improved accuracy of cell sizing and typing by taking into account electrical field effects that might otherwise cause errors in particle sizing. The channel sensor may additionally or alternatively be calibrated using various reagents with known pH and/or electrolyte concentrations, which can verify the conductivity of the pore.

In some embodiments, the channel sensor is calibrated during operation of the cartridge, for example before or after a biological sample is analyzed. This calibration may be conducted using reagent stored or mixed on the cartridge and transported to the channel sensor using the electrowetting electrodes.

In some embodiments, the cartridge includes a plurality of cell analyzer sensors, such as two, three, four, or more. The different cell analyzers may be redundant or specialized. Using different cell analyzers, the biological sample may be dynamically analyzed, for example by passing the biological sample through a first cell analyzer, and then through a second cell analyzer, wherein the second cell analyzer is selected based on the results of the first cell analyzer. For example, if the biological sample is determined to have a low cell count of a particular type of cell (e.g., white blood cells, red blood cells, or platelets), the biological sample may be subsequently may be further processed either by mixing with specific reagents or by physically isolating a particular cell type and is then analyzed using a differently configured cell analyzer (e.g., with a different pore size, functionalized with one or more molecules, or having a filter to remove certain cell types) to more accurately count that particular type of cell.

Electrowetting Electrodes

The electrowetting electrodes in the cartridge are configured to transport an aqueous liquid (such as a biological sample or processed biological sample) by electrowetting actuation (also referred to as digital microfluidics), split the biological sample into one or more subsamples, mix one or more reagents together, or mix one or more reagents with the biological sample or subsample to process or dilute the biological sample or subsample. The electrowetting electrodes can transport the biological sample, for example, throughout the main chamber or channel of the cartridge. The individual electrodes in the plurality of electrowetting electrodes can be individually controlled, for example by the electrowetting electrode driver in the device when engaged with the cartridge. Use of the electrowetting electrodes to transport the biological sample in the main chamber allows for increased versatility in transporting the biological sample compared to channel-based fluid transport, which is linear and generally relies on capillary flow (which allows for limited control) or moving parts, such as pumps, to transport the sample. Electrowetting-based fluid transport allows for precise movement of the biological sample, reagent mixing, dilution, and sample splitting.

Electrowetting actuation is driven by applying a voltage to a fluid positioned above an activated electrode. The voltage alters the contact angle of the fluid by creating a charge on the fluid contacting surface, which attracts the fluid to the activated electrode. The reduce the voltage required for electrowetting actuation, the thickness of the insulating and/or hydrophobic layers needs to be reduced without causing dielectric breakdown of the material. It is therefore desirable to use a thinly applied material with a high dielectric constant with a high dielectric strength to reduce the voltage required for electrowetting actuation and creating the necessary charge on the fluid contacting surface.

Figure 16A:
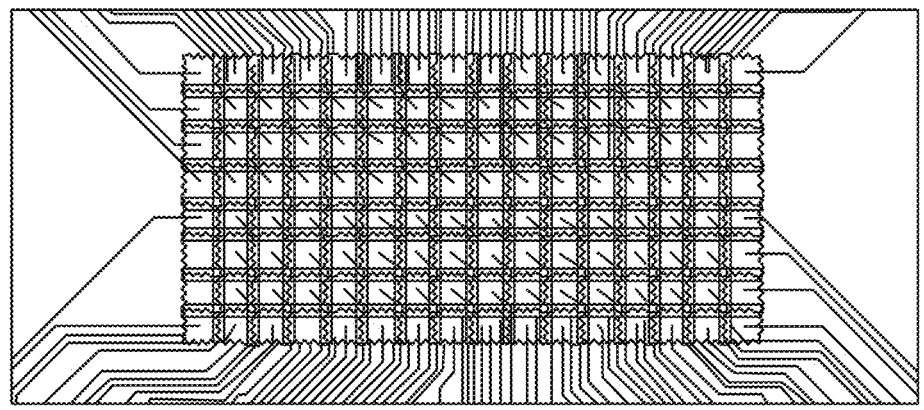
FIG. 16A illustrates an exemplary electrowetting electrode array in an 8×16 matrix with tracks electrically connecting each electrode with the device interface.
Figure 16B:
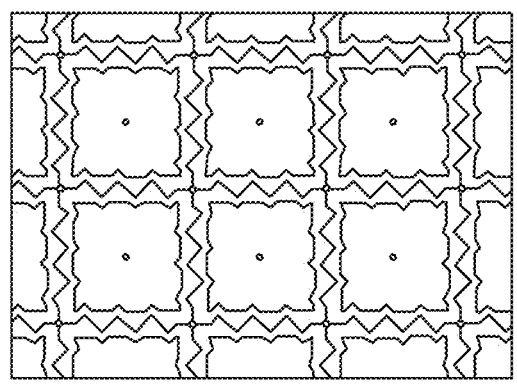
FIG. 16B shows a zoomed in view of several electrowetting electrodes in the array shown in FIG. 16A, which highlights the jagged edges of the approximately square electrodes.

The electrowetting electrodes in the cartridge can be arranged as an array of spaced electrodes that in electrical communication with the device, which operates the electrowetting electrodes. The device can operate the electrowetting electrodes using a switch that selectively operates the electrodes within the array to actuate liquids (e.g., reagents or the biological sample). The electrowetting electrodes are spaced from one another, with an insulating layer filling the spaces between the electrowetting electrodes. The space between electrowetting electrodes can vary within the array depending on the size of the electrowetting electrodes. For example, in some embodiments, the space between electrodes is about 10 μm to about 150 μm (such as about 10 μm to about 20 μm, about 20 μm to about 50 μm, about 50 μm to about 100 μm, or about 100 μm to about 150 μm). The size of the electrowetting electrode can also vary within the array depending on the liquid volume intended to occupy the electrode. For example, an electrowetting electrode configured to actuate a liquid volume of 20 μL is about 0.632 mm by about 0.632 mm In some embodiments the electrowetting electrodes are approximately square or rectangular, although in some embodiments the electrowetting electrodes may have jagged or protruding circular edges with partial overlap between the adjacent electrode. FIG. 16A illustrates an exemplary electrowetting electrode array in an 8×16 matrix with tracks electrically connecting each electrode with the device interface. FIG. 16B shows a zoomed in view of several electrowetting electrodes, which highlights the jagged edges of the approximately square electrodes.

The electrowetting electrodes are coated with an insulating layer (i.e., a dielectric layer), which is preferably a high-κ material (i.e., has a dielectric constant of about 3.9 or higher). The insulating layer can also fill spaces between the electrowetting electrodes. In some embodiments, the insulating layer has a dielectric constant of about 3.9 or higher (such as about 5 or higher, about 10 or higher, about 20 or higher, about 40 or higher, about 60 or higher, about 100 or higher, about 200 or higher, about 400 or higher, about 1000 or higher, or about 2000 or higher). In some embodiments, the insulating layer has a dielectric constant of about 3.9 to about 20,000 (such as about 3.9 to about 5, about 5 to about 10, about 10 to about 20, about 20 to about 40, about 40 to about 60, about 60 to about 100, about 100 to about 200, about 200 to about 400, about 400 to about 1000, about 1000 to about 2000, about 2000 to about 4000, about 4000 to about 6000, about 6000 to about 10,000, or about 10,000 to about 20,000). Exemplary materials for the insulating layer comprise or are hafnium oxide, barium strontium titanate, or strontium titanate, silica, and silicon nitride.

The insulating layer is preferably a thin layer deposited onto the surface of the electrodes. The thickness is minimized to reduce the required voltage without resulting in dielectric breakdown of the dielectric materials. For example, the insulating layer may be coated onto the electrode using atomic layer deposition, chemical vapor deposition, reactive ion beam deposition, sputter deposition, evaporation, spray deposition, spin coating, or sol-gel formation. In some embodiments, the insulating layer has a thickness of about 1 nm to about 5 μm. For example, in some embodiments the insulating layer has a thickness of about 1 nm to about 10 nm, about 10 nm to about 20 nm, about 20 nm to about 40 nm, about 40 nm to about 100 nm, about 100 nm to about 250 nm, about 250 nm to about 500 nm, about 500 nm to about 1 μm, or about 1 μm to about 5 μm. When the insulating layer comprises a metal oxide, the insulating layer is generally thinner than if the insulating layer comprises a polymeric material. For example, in some embodiments the insulating layer comprises a metal oxide and has a thickness of about 1 nm to about 100 nm. In some embodiments, the insulating layer comprises a polymeric material and has a thickness of about 0.1 µm to about 5 µm. In some embodiments, the distance between the electrode and the fluid contacting surface is about 1 nm to about 25 µm. For example, in some embodiments the distance between the electrode and the fluid contacting surface is about 1 nm to about 10 nm, about 10 nm to about 20 nm, about 20 nm to about 40 nm, about 40 nm to about 100 nm, about 100 nm to about 250 nm, about 250 nm to about 500 nm, about 500 nm to about 1 µm, about 1 µm to about 5 µm, about 5 µm to about 10 µm, or about 10 µm to about 25 µm.

In some embodiments, the insulating layer has a surface that contacts the biological sample and/or reagent (i.e. a fluid contacting layer). The fluid contacting surface is preferably a hydrophobic surface having a contact angle of 90° or higher with water at 25° C. In some embodiments, the hydrophobic surface has a contact angle of about 90° to about 160° (such as about 90° to about 100°, about 100° to about 110°, about 110° to about 120°, about 120° to about 130°, about 130° to about 140°, about 140° to about 150°, or about 140° to about) 150° with water at 25° C. In some embodiments, the insulating layer is or comprises a hydrophobic material (that is, a high-κ material that can act as an insulating material that is hydrophobic). To further increase the hydrophobicity of the fluid contacting surface of the insulating layer, the insulating layer can optionally include a nanostructured surface, which may be, for example, a woven pattern, a nano-pillar pattern, or a nano-grass pattern. The nanostructure pattern may be formed, for example, by etching into the insulating layer.

In some embodiments, the insulating layer is optionally coated with a hydrophobic material, which can be the fluid contacting layer. In some embodiments, the hydrophobic layer is applied, for example, using thin film deposition or spin coating. Optionally, the fluid contacting surface of the hydrophobic layer has a nanostructured surface, which may be, for example, a woven pattern, a nano-pillar pattern, or a nano-grass pattern. The nanostructure pattern may be formed, for example, by etching into the hydrophobic layer, for by wet etching or dry etching into the fluid contacting layer (e.g., the insulating layer or a separate hydrophobic layer). Photolithography or ion etching, for example, can be used to create a predefined pattern. Exemplary hydrophobic materials for the hydrophobic layer include a fluoropolymer, a silane, a fluorinated silane, polydimethylsiloxane, or a parylene.

The fluid-contacting surface (which may be, for example, the surface of the insulating layer or a hydrophobic coating) may have a nanostructured surface (i.e., a nanostructured pattern on the fluid-contacting surface). The nanostructured surface can alter the hydrophobicity of the surface, thus decreasing the voltage required to actuate fluid on the electrowetting electrodes. Exemplary nanostructured surfaces include, but are not limited to, a woven pattern, a nano-pillar pattern, or a nano-grass pattern. In some embodiments the hydrophobic nanostructured patterned surface is patterned on the insulating surface, such that no additional materials coatings are needed. In other embodiments, the nanostructured hydrophobic surface is formed on top of one or more insulating layers to form the hydrophobic surface on the top insulating surface.

In some embodiments, the hydrophobic layer is formed using long chain molecules that self-assemble on the insulating layer. For example, the long chain molecules for the hydrophobic layer may include molecules with an alkane hydrocarbon as a head group with or without a spacer moiety and an end group which specifically assembles on the insulating substrate, such as octadecanehydroxamic acid, stearic acid, octadecanephosphonic acid, 16-hydroryhexadecanehydroramic acid, or octadecanethiol. These materials form a hydrophobic layer on the insulating layer. For example, the hydrophobic layer may be between about 2.5 nm and about 30 nm thick. This thin hydrophobic layer adds hydrophobicity to the fluid contacting surface without adding substantial thickness to the layers coating the electrowetting electrodes.

The thin distance and high hydrophobicity of the surface contacting the biological sample or reagent allows for lower voltages to be applied to the electrowetting electrodes to allow for electrowetting actuation. For example, in some embodiments, the plurality of electrowetting electrodes is configured to transport the biological sample using a voltage of less than about 50 volts. In some embodiments, the plurality of electrowetting electrodes is configured to transport the biological sample using a voltage of about 0.5 volts to about 50 volts (such as about 0.5 volts to about 1 volt, about 1 volt to about 5 volts, about 5 volts to about 10 volts, about 10 volts to about 20 volts, about 20 volts to about 30 volts, about 30 volts to about 40 volts, or about 40 volts to about 50 volts).

The plurality of electrowetting electrodes can include a plurality of coplanar electrodes, which can be positioned along the bottom surface of the main chamber or channel of the cartridge. Optionally, the cartridge includes a ground electrode (which may be a continuous ground electrode or a plurality of separate ground electrodes) on the top surface (i.e., opposite of the surface with the coplanar electrodes) of the main chamber or channel. The electrowetting electrodes can be coated with one or more layers, as further described herein, with the top layer being a fluid contacting layer, which contacts the biological sample and/or reagents as they are transported within the cartridge. Activation of individual electrodes modulates the hydrophobicity of the fluid contacting layer above the electrode, thereby actuating the fluid (e.g., the biological sample or reagent) to a position above the activated electrode.

The electrowetting electrodes can comprise any suitable conductive material, such as gold, silver, silver chloride, platinum, indium tin oxide (ITO), or a conductive carbon. Conductive carbons can include conductive carbon inks, which may include carbon particles (e.g., graphite) mixed with other conductive particles, for example a carbon silver ink.

Figure 17A:
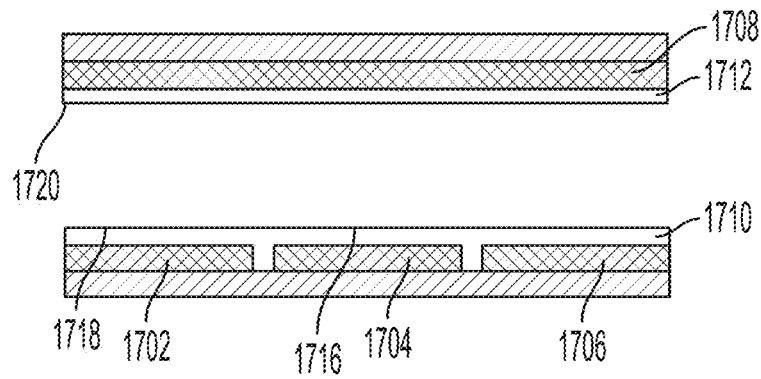
FIG. 17A illustrates one embodiment of a plurality of electrowetting electrodes comprising an insulating layer fluid contacting surface.

FIG. 17A illustrates one embodiment of a plurality of electrowetting electrodes comprising an insulating layer fluid contacting surface. The plurality of electrowetting electrodes includes a first electrowetting electrode 1702, a second electrowetting electrode 1704, and a third electrowetting electrode 1706. On a surface opposite the first electrowetting electrode 1702, the second electrowetting electrode 1704, and the third electrowetting electrode 1706, there is a ground electrode 1708 that is common to the three electrowetting electrodes. An insulating layer 1710 coats the first electrowetting electrode 1702, the second electrowetting electrode 1704, and the third electrowetting electrode 1706, along with the spaces between the electrowetting electrodes. The ground electrode 1708 is also coated with an insulating layer 1712. Fluid, such as the biological sample and/or the one or more reagents, can be transported through the gap 1714 between the ground electrode 1708 and the first, second, and third electrowetting electrodes. The fluid contacting surface 1716 of the insulating layer 1710 can be nanostructured to increase hydrophobicity of the fluid contacting surface. The fluid contacting surface 1718 of the insulating layer 1710 and/or fluid contacting surface 1719 of the insulating layer 1712 can also be nanostructured to increase hydrophobicity of the fluid contacting surface.

Figure 17B:
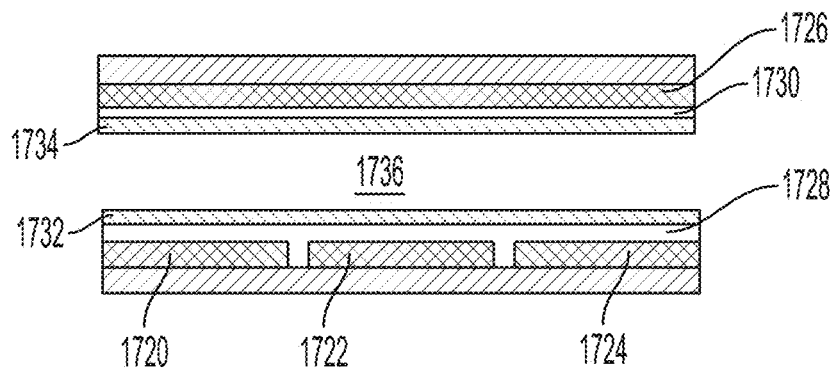
FIG. 17B illustrates another embodiment of a plurality of electrowetting electrodes, comprising an insulating layer coating the electrowetting electrodes, and a hydrophobic layer coating the insulating layer.

FIG. 17B illustrates another embodiment of a plurality of electrowetting electrodes, comprising an insulating layer coating the electrowetting electrodes, and a hydrophobic layer coating the insulating layer. The plurality of electrowetting electrodes includes a first electrowetting electrode 1720, a second electrowetting electrode 1722, and a third electrowetting electrode 1724. On a surface opposite the first electrowetting electrode 1720, the second electrowetting electrode 1722, and the third electrowetting electrode 1724, there is a ground electrode 1726 that is common to the three electrowetting electrodes. An insulating layer 1728 coats the first electrowetting electrode 1720, the second electrowetting electrode 1722, and the third electrowetting electrode 1724, along with the spaces between the electrowetting electrodes. The ground electrode 1726 is also coated with an insulating layer 1730. Coating the insulating layer 1728 is a hydrophobic layer 1732, and coating the insulating layer 1730 is a hydrophobic layer 1734. Fluid, such as the biological sample and/or the one or more reagents, can be transported through the gap 1736 between the hydrophobic layer 1732 and 1734. Optionally, the fluid contacting surface of hydrophobic layer 1732 and/or the fluid contacting surface of hydrophobic layer 1734 is nanostructured to increase the hydrophobicity of the fluid contacting layer.

Figure 17C:
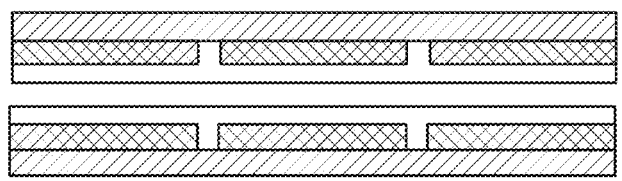
FIG. 17C illustrates another embodiment of a plurality of electrowetting electrodes comprising an insulating layer fluid contacting surface.
Figure 17D:
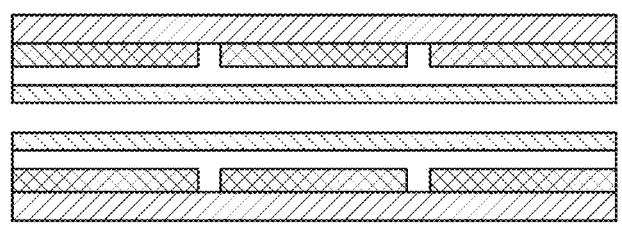
FIG. 17D illustrates another embodiment of a plurality of electrowetting electrodes, comprising an insulating layer coating the electrowetting electrodes, and a hydrophobic layer coating the insulating layer.

One or more of the electrowetting electrodes can include an individual ground electrode opposite the electrowetting electrode in place of a common ground electrode. In some embodiments, a portion of the electrowetting electrodes include a common ground electrode and a portion of the electrowetting electrodes include an individual ground electrode. Examples of these configurations are shown in FIG. 17C (without a separate hydrophobic layer) and FIG. 17D (with a separate hydrophobic layer).

In some embodiments, there is a method of transporting a liquid, comprising positioning an aqueous liquid on a first hydrophobic liquid contact surface above an inactivated first electrowetting electrode; and activating a second electrowetting electrode by applying a voltage of about 50 volts or less to the second electrowetting electrode, thereby transporting the aqueous liquid from the first hydrophobic liquid contact surface to a second hydrophobic liquid contact surface above the second electrowetting electrode; wherein the first electrowetting electrode and the second electrowetting electrode are coated with and separated by an insulating layer.

The aqueous liquid can be a biological sample, such as blood, serum, saliva, sweat, tears, mucus, urine, or any other biological sample or derivative suspended in a fluid. In some embodiments, the liquid is a processed biological sample, which may be processed by mixing the liquid with one or more reagents. The reagent can be mixed with the biological sample, using the electrowetting electrodes. For example, in some embodiments, the method includes transporting a reagent to the liquid contacting surface containing the liquid, thereby mixing the reagent with the aqueous liquid.

The biological sample is transported by the electrowetting electrodes using a voltage of about 50 volts or less. For example, in some embodiments, the biological sample is transported using about 0.5 volts to about 50 volts (such as about 0.5 volts to about 1 volt, about 1 volt to about 2 volts, about 2 volts to about 3 volts, about 3 volts to about 4 volts, about 4 volts to about 5 volts, about 5 volts to about 10 volts, about 10 volts to about 20 volts, about 20 volts to about 30 volts, about 30 volts to about 40 volts, or about 40 volts to about 50 volts).

Methods for Analyzing the Biological Sample

The cartridges and devices described herein can be used to analyze a biological sample, for example to determine a blood cell count or an analyte concentration. To analyze the sample, the biological sample is deposited into a cartridge, and the biological sample is transported within the cartridge using a plurality of electrowetting electrodes (i.e., by electrowetting actuation). The biological sample is analyzed using one or more sensors within the cartridge to generate analytical data, which is transmitted from the cartridge (e.g., to a device engaged with the cartridge). The biological sample can be mixed with one or more reagents within the cartridge, for example to form a processed biological sample which is analyzed using one or more of the sensors. The cartridge can be disposed after a single use.

In some embodiments, the biological sample is received by the cartridge using a capillary action. The biological sample can fill a receiving chamber, which can determine the volume of biological sample that enters the cartridge. After analysis by the one or more sensors, the biological sample can be transported (e.g., through electrowetting actuation) to a waste reservoir, where it can be stored until the cartridge is disposed of.

The biological sample can be transported within the cartridge (for example from the sample receiving report, to a mixing region, to one or more of the sensors, or to the waste reservoir) by electrowetting actuation. The electrowetting electrodes may be coated with an insulating layer and/or a hydrophobic layer, either of which may include a hydrophobic fluid contact surface, which may have a nanostructured pattern. To transport the biological sample, a first electrowetting electrode is activated by applying a voltage potential to the first electrowetting electrode to attract the biological sample to a position above the first electrode. Once the biological sample is in a position above the first electrode, a second electrowetting electrode is activated by applying a voltage to the second electrowetting electrode and the first electrowetting electrode is deactivated, thereby transporting the biological sample to a position above the second electrowetting electrode. In some embodiments, the voltage is about 0.5 volts to about 1000 volts (such as about 0.5 volts to about 1 volt, about 1 volt to about 5 volts, about 5 volts to about 10 volts, about 10 volts to about 20 volts, about 20 volts to about 30 volts, about 30 volts to about 50 volts, about 50 volts to about 100 volts, about 100 volts to about 250 volts, about 250 volts to about 500 volts, or about 500 volts to about 1000 volts). Preferably, the plurality of electrowetting electrodes are operated using about 50 volts or less, or more preferably about 20 volts or less.

In some embodiments, analyzing the biological sample includes counting a number of cells in the biological sample. The analytical data transmitted by the cartridge can include information relating to the number of cells. In some embodiments, counting a number of cells includes differentiating two or more different cell types, and the analytical data includes information related to a type of cells and a number of cells. The different cell types can be, for example, white blood cells, red blood cells, or platelets. In some embodiments, the different cell types can include eosinophils, basophils, neutrophils, monocytes, and lymphocytes. Accordingly, in some embodiments, analyzing the biological sample includes counting white blood cells, counting red blood cells, counting platelets, counting eosinophils, counting basophils, counting neutrophils, counting monocytes, and/or counting lymphocytes. Analyzing the biological sample can include applying an electrical current to the biological sample and recording a multiplexed impedance of the electrical current. The analytical data (i.e., the multiplexed impedance) can be used to determine a number of cells or a number of cell types in the biological sample. In some embodiments, analyzing the biological sample includes self-calibrating at least one of the sensors to detect different cell sizes or different cell types.

To analyze the biological sample using the cell analyzer sensor, the biological sample continuously flows through a channel comprising a microchannel or micropore. A multiplexed electrical current is applied to the micropore or microchannel as the biological sample flows through the micropore or microchannel Multiplexed electrical impedance within the micropore or microchannel is measured, and analytical data relating to the multiplexed electrical impedance is transmitted from the cartridge. The electrical current can be a mixed current comprising a direct current component and a plurality (e.g., 2, 3, 4, 5, 6, 7, 8 or more) of alternating current components at different frequencies. Preferably, the multiplexed current includes at least three alternating current components. In some embodiments, the alternating current components comprises a first alternating current at about 1 kHz to about 100 kHz (e.g., about 1 kHz to about 10 kHz, about 10 kHz to about 20 kHz, about 20 kHz to about 30 kHz, about 30 kHz to about 40 kHz, about 40 kHz to about 50 kHz, about 50 kHz to about 60 kHz, about 60 kHz to about 70 kHz, about 70 kHz to about 80 kHz, about 80 kHz to about 90 kHz, or about 90 kHz to about 100 kHz), a second alternating current at about 100 kHz to about 1 MHz (such as about 100 kHz to about 200 kHz, about 200 kHz to about 300 kHz, about 300 kHz to about 400 kHz, about 400 kHz to about 500 kHz, about 500 kHz to about 600 kHz, about 600 kHz to about 700 kHz, about 700 kHz to about 800 kHz, about 800 kHz to about 900 kHz, or about 900 kHz to about 1000 kHz), and a third alternating current of about 1 MHz or more (such as about 1 MHz to about 10 MHz, about 10 MHz to about 20 MHz, about 20 MHz to about 30 MHz, about 30 MHz to about 40 MHz, about 40 MHz to about 50 MHz, about 50 MHz to about 60 MHz, about 60 MHz to about 70 MHz, about 70 MHz to about 80 MHz, about 80 MHz to about 90 MHz, or about 90 MHz to about 100 MHz). In another embodiment, the multiplexed current includes (1) a direct current or an alternating current at about 1 kHz to about 100 kHz (e.g., about 1 kHz to about 10 kHz, about 10 kHz to about 20 kHz, about 20 kHz to about 30 kHz, about 30 kHz to about 40 kHz, about 40 kHz to about 50 kHz, about 50 kHz to about 60 kHz, about 60 kHz to about 70 kHz, about 70 kHz to about 80 kHz, about 80 kHz to about 90 kHz, or about 90 kHz to about 100 kHz), (2) an alternating current at about 50 kHz to about 250 kHz (such as about 50 kHz to about 70 kHz, about 70 kHz to about 90 kHz, about 90 kHz to about 110 kHz, about 110 kHz to about 130 kHz, about 130 kHz to about 150 kHz, about 150 kHz to about 200 kHz, or about 200 kHz to about 250 kHz), (3) an alternating current of about 250 kHz to about 700 kHz (such as about 250 kHz to about 300 kHz, about 300 kHz to about 350 kHz, about 350 kHz to about 400 kHz, about 400 kHz to about 500 kHz, about 500 kHz to about 600 kHz, or about 600 kHz to about 700 kHz; (4) an alternating current of about 700 kHz to about 5 MHz (such as about 700 kHz to about 800 kHz, about 800 kHz to about 900 kHz, or about 900 kHz to about 1 MHz, or about 1 MHz to about 2 MHz, about 2 MHz to about 3 MHz, about 3 MHz to about 4 MHz, or about 4 MHz to about 5 MHz), (5) an alternating current of about 5 MHz to about 20 MHz (such as about 5 MHz to about 10 MHz, about 10 MHz to about 15 MHz, or about 15 MHz to about 20 MHz), and (6) an alternating current of about 20 MHz or more (such as about 20 MHz to about 30 MHz, about 30 MHz to about 40 MHz, about 40 MHz to about 50 MHz, about 50 MHz to about 60 MHz, about 60 MHz to about 70 MHz, about 70 MHz to about 80 MHz, about 80 MHz to about 90 MHz, about 90 MHz to about 100 MHz, about 100 MHz to about 125 MHz, or about 125 MHz to about 150 MHz). In some embodiments, the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz. A number of cells in the biological sample and/or a number of two or more different cell types can be determined based on the measured multiplexed impedance. The analyzed impedance can include real and/or imaginary components. Alternatively, the analyzed impedance can include magnitude and/or phase components.

In some embodiments, to analyze the sample, the biological sample is deposited into a cartridge, and the biological sample is transported within the cartridge using a plurality of electrowetting electrodes (i.e., by electrowetting actuation). The biological sample is analyzed using one or more sensors within the cartridge to generate analytical data, which is transmitted from the cartridge (e.g., to a device engaged with the cartridge). The biological sample can be mixed with one or more reagents within the cartridge, for example to form a processed biological sample which is analyzed using one or more of the sensors. The cartridge can be disposed after a single use.

In some embodiments, the biological sample is received by the cartridge using a capillary action. The biological sample can fill a receiving chamber, which can determine the volume of biological sample that enters the cartridge. After analysis by the one or more sensors, the biological sample can be transported (e.g., through electrowetting actuation) to a waste reservoir, where it can be stored until the cartridge is disposed of.

The biological sample can be transported within the cartridge (for example from the sample receiving report, to a mixing region, to one or more of the sensors, or to the waste reservoir) by electrowetting actuation. To transport the biological sample, a first electrowetting electrode is activated by applying a voltage potential to the first electrowetting electrode to attract the biological sample to a position above the first electrode. Once the biological sample is in a position above the first electrode, a second electrowetting electrode is activated by applying a voltage to the second electrowetting electrode and the first electrowetting electrode is deactivated, thereby transporting the biological sample to a position above the second electrowetting electrode.

In some embodiments, analyzing the biological sample comprises determining the presence of or measuring a concentration of an analyte (e.g., a protein) within the biological sample. The biological sample can be statically positioned within the sensor (which may be, for example, an impedance sensor or an optical sensor), for example using electrowetting actuation (e.g., using electrowetting electrodes). The presence or concentration of the analyte can be determined by binding the analyte in the biological sample to an affinity moiety bound to an electrode within the sensor, and measuring an impedance change resulting from the analyte binding to the affinity moiety. The impedance change can be calibrated, for example, to impedance due to a reference solution that does not include the biological sample. The affinity moiety may be, for example, an antibody, an antibody fragment, or an aptamer (such as a DNA aptamer, an RNA aptamer, or an XNA aptamer). Impedance detected by the sensor can be transmitted from the cartridge, and the impedance change can be used to determine the presence or concentration of the analyte.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

EXEMPLARY EMBODIMENTS

The following embodiments are exemplary and should not be considered limiting of the invention or inventions described herein.

Embodiment 1. A cartridge for analyzing a biological sample, comprising:
a sample receiving port configured to receive the biological sample;
a sensor configured to analyze the biological sample;
a cartridge space in fluid communication with the biological sample receiving port and the sensor;
a plurality of electrowetting electrodes configured to transport the biological sample in the cartridge space and combine the biological sample with one or more reagents; and
a device interface configured to receive power from and communicate with a cartridge interface on a device, wherein the sensor and the plurality of electrowetting electrodes are in electrical communication with the device interface.

Embodiment 2. The cartridge of embodiment 1, wherein the cartridge space is fluidly connected to one or more reagent reservoirs.

Embodiment 3. The cartridge of embodiment 2, wherein the one or more reagent reservoirs comprise a reagent.

Embodiment 4. The cartridge of embodiment 2 or 3, wherein the cartridge space comprises a reagent mixing region.

Embodiment 5. The cartridge of any one of embodiments 1-4, wherein the cartridge is a single-use cartridge.

Embodiment 6. The cartridge of any one of embodiments 1-5, comprising a waste reservoir configured to receive the biological sample after being analyzed by the sensor.

Embodiment 7. The cartridge of any one of embodiments 1-6, wherein the biological sample enters the sample receiving port through capillary action.

Embodiment 8. The cartridge of any one of embodiments 1-7, wherein the plurality of electrowetting electrodes comprises a plurality of coplanar electrodes.

Embodiment 9. The cartridge of embodiment 8, wherein the plurality of electrowetting electrodes further comprises a ground electrode on a surface opposite from the coplanar electrodes.

Embodiment 10. The cartridge of embodiment 9, wherein the ground electrode is common to two or more of the electrowetting electrodes.

Embodiment 11. The cartridge of embodiment 9, wherein at least one of the electrowetting electrodes is paired with an individual ground electrode.

Embodiment 12. The cartridge of any one of embodiments 1-11, wherein the electrowetting electrodes are coated with an insulating layer.

Embodiment 13. The cartridge of embodiment 12, wherein the insulating layer has a dielectric constant of about 3.9 or higher.

Embodiment 14. The cartridge of embodiment 12 or 13, wherein the insulating layer comprises hafnium oxide, barium strontium titanate, or strontium titanate, silica, or silicon nitride.

Embodiment 15. The cartridge of any one of embodiments 12-14, wherein the insulating layer is coated on the electrode using atomic layer deposition, chemical vapor deposition, reactive ion beam deposition, sputter deposition, evaporation, spray deposition, spin coating, or sol-gel formation.

Embodiment 16. The cartridge of any one of embodiments 12-15, wherein the insulating layer has a thickness of about 1 nm to about 5 μm.

Embodiment 17. The cartridge of any one of any one of embodiments 12-16, wherein the insulating layer is a fluid contacting layer.

Embodiment 18. The cartridge of embodiment 17, wherein the insulating layer comprises a nanostructured surface.

Embodiment 19. The cartridge of any one of embodiments 1-18, wherein the electrowetting electrodes are coated with a hydrophobic layer.

Embodiment 20. The cartridge of embodiment 19, wherein the hydrophobic layer is a fluid contacting layer.

Embodiment 21. The cartridge of embodiment 20, wherein the hydrophobic layer comprises a nanostructured surface.

Embodiment 22. The cartridge of any one of embodiments 19-21, wherein the hydrophobic layer comprises a fluoropolymer, polydimethylsiloxane, a parylene, octadecanehydroxamic acid, stearic acid, octadecanephosphonic acid, 16-hydroryhexadecanehydroramic acid, or octadecanethiol.

Embodiment 23. The cartridge of any one of embodiments 19-22, wherein the hydrophobic layer is coated over the insulating layer.

Embodiment 24. The cartridge of any one of embodiments 1-23, wherein the electrowetting electrodes comprise gold, silver, silver chloride, platinum, indium tin oxide, or a conductive carbon.

Embodiment 25. The cartridge of any one of embodiments 1-24, wherein the electrowetting electrodes are separated from a fluid contacting surface by about 1 nm to about 25 μm.

Embodiment 26. The cartridge of any one of embodiments 1-25, wherein the plurality of electrowetting electrodes is configured to transport the biological sample using a voltage of less than about 50 volts.

Embodiment 27. The cartridge of any one of embodiments 1-26, wherein the plurality of electrowetting electrodes is configured to transport the biological sample using a voltage of about 0.5 V to about 50V.

Embodiment 28. The cartridge of any one of embodiments 1-27, wherein the sensor is an impedance sensor.

Embodiment 29. The cartridge of any one of embodiments 1-29, wherein the sensor is configured to detect a protein or measure an amount of the protein.

Embodiment 30. The cartridge of embodiment 28 or 29, wherein the sensor comprises a first sensing electrode functionalized with an affinity moiety, and a second sensing electrode paired with the first sensing electrode, wherein the sensor is configured to detect a change in impedance upon binding of an analyte or a protein to the affinity moiety.

Embodiment 31. The cartridge of embodiment 30, wherein the affinity moiety is an antibody, an antibody fragment, or an aptamer.

Embodiment 32. The cartridge of embodiment 30 or 31, wherein the first sensing electrode is an electrowetting electrode.

Embodiment 33. The cartridge of embodiment 30 or 31, wherein the sensor further comprises a first electrowetting electrode and a second electrowetting electrode, wherein the first electrowetting electrode and the second electrowetting electrode are on opposite sides of the first sensing electrode or the second sensing electrode.

Embodiment 34. The cartridge of embodiment 33, wherein the first sensing electrode is an electrowetting electrode.

Embodiment 35. The cartridge of embodiment 33 or 34, wherein the plurality of electrowetting electrodes is configured to statically position at least a portion of the biological sample between the first sensing electrode and the second sensing electrode.

Embodiment 36. The cartridge of embodiment 34 or 35, wherein the first electrowetting electrode, the second electrowetting electrode, and the first sensing electrode are electrically connected to a voltage switching circuit configured to selectively activate one or none of the first electrowetting electrode, the second electrowetting electrode, or the first sensing electrode.

Embodiment 37. The cartridge of embodiment 36, wherein the voltage switching circuit is electrically connected to a switch configured to alternatively select an impedance sensing circuit or an electrowetting electrode supply circuit.

Embodiment 38. The cartridge of any one of embodiments 28-37, wherein the impedance sensor comprises a pH-sensitive or ion-sensitive layer configured to modulate impedance based on pH or ion concentration.

Embodiment 39. The cartridge of embodiment 38, wherein the impedance sensor comprises a metal oxide semiconductor capacitor (MOSCap) sensor.

Embodiment 40. The cartridge of embodiment 39, wherein the MOSCap sensor is adjacent to the first sensing electrode and the second sensing electrode.

Embodiment 41. The cartridge of any one of embodiments 1-40, wherein the cartridge further comprises one or more optical windows.

Embodiment 42. The cartridge of any one of embodiments 1-41, wherein the sensor is a channel sensor, comprising:
a first channel segment,
a second channel segment,
a pore or channel fluidly connecting the first channel segment and the second channel segment, and
an electrode pair configured to apply an electrical current to the pore or channel, and to detect impedance within the pore or channel.

Embodiment 43. The cartridge of embodiment 42, wherein the electrode pair is configured to direct contact a liquid flowing through the channel sensor.

Embodiment 44. The cartridge of embodiment 42 or 43, wherein the channel sensor is a flow cytometer configured to count a number of cells in the biological sample.

Embodiment 45. The cartridge of embodiment 44, wherein the sensor is configured to differentiate between different types of cells.

Embodiment 46. The cartridge of embodiment 45, wherein the sensor is configured to differentiate between red blood cells, white blood cells, and platelets.

Embodiment 47. The cartridge of embodiment 45 or 46, wherein the sensor is configured to count a number of red blood cells, a number of white blood cells, or a number of platelets.

Embodiment 48. The cartridge of any one of embodiments 45-47, wherein the sensor is configured to differentiate between eosinophils, basophils, neutrophils, monocytes, and lymphocytes.

Embodiment 49. The cartridge of any one of embodiments 45-48, wherein the sensor is configured to count a number of eosinophils, a number of basophils, a number of neutrophils, a number of monocytes, or a number of lymphocytes.

Embodiment 50. The cartridge of any one of embodiments 42-49, where the pore or channel is a micropore or a microchannel.

Embodiment 51. The cartridge of any one of embodiments 42-50, wherein the electrical current is a multiplexed current comprising a plurality of alternating current components at different frequencies.

Embodiment 52. The cartridge of any one of embodiments 42-51, wherein the electrical current is a multiplexed current comprising a (1) a direct current component or a low-frequency alternating current, and (2) a plurality of alternating current components at different frequencies.

Embodiment 53. The cartridge of embodiment 51 or 52, wherein the plurality of alternating current components comprises at least three alternating current components.

Embodiment 54. The cartridge of embodiment 53, wherein the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz.

Embodiment 55. The cartridge of any one of embodiments 51-54, wherein the plurality of alternating current comprises at least five different alternating current components.

Embodiment 56. The cartridge of embodiment 55, wherein the plurality of alternating current components comprises a first alternating current at about 50 kHz to about 250 kHz, a second alternating current at about 250 kHz to about 700 kHz, a third alternating current at about 700 kHz to about 5 MHz, a fourth alternating current at about 5 MHz to about 20 MHz, and a fifth alternating current at about 20 MHz to about 150 MHz.

Embodiment 57. The cartridge of any one of embodiments 42-56, wherein the electrode pair is configured to detect impedance at a sampling rate of about 100 kHz or more.

Embodiment 58. The cartridge of any one of embodiments 42-57, wherein the electrode pair is configured to detect a real impedance component and an imaginary impedance component within the pore or channel.

Embodiment 59. The cartridge of any one of embodiments 42-57, wherein the electrode pair is configured to detect a magnitude impedance component and a phase impedance component within the pore or channel.

Embodiment 60. The cartridge of embodiment 42 or 43, wherein the channel sensor is configured to detect an analyte concentration.

Embodiment 61. The cartridge of embodiment 60, wherein the analyte is a protein.

Embodiment 62. The cartridge of embodiment 60 or 61, wherein the cartridge comprises a reagent comprising an affinity moiety, and wherein the cartridge is configured to mix the reagent comprising the affinity moiety with the biological sample or a subsample derived therefrom, and transport the biological sample or subsample to the channel sensor.

Embodiment 63. The cartridge of any one of embodiments 60-62, wherein the pore or channel is a nanopore or a nanochannel.

Embodiment 64. The cartridge of any one of embodiments 1-63, wherein the cartridge comprises a plurality of sensors.

Embodiment 65. The cartridge of any one of embodiments 1-64, wherein the biological sample is a blood sample.

Embodiment 66. The cartridge of any one of embodiments 1-65, wherein the cartridge space is a chamber or a channel.

Embodiment 67. A system for analyzing a biological sample, comprising:
the cartridge of any one of embodiments 1-66; and
a device comprising a cartridge interface configured to interface with the cartridge, the device configured to power and operate the cartridge.

Embodiment 68. The system of embodiment 67, wherein the device is configured to power and operate two or more different types of cartridges.

Embodiment 69. The system of embodiment 67 or 68, wherein the device further comprises one or more processors and a non-transitory computer-readable storage medium storing one or more programs configured to be executed by the one or more processors, the one or more programs comprising instructions for (a) operating the plurality of electrowetting electrodes in the cartridge to transport the biological sample within the cartridge, and (b) operating the sensor.

Embodiment 70. The system of embodiment 69, wherein the one or more programs comprise instructions for operating the plurality of electrowetting electrodes in the cartridge to continuously transport the biological sample through the sensor.

Embodiment 71. The system of embodiment 70, wherein the one or more programs comprise instructions for operating the plurality of electrowetting electrodes in the cartridge to statically position the biological sample within the sensor.

Embodiment 72. The system of any one of embodiments 69-71, wherein the one or more programs comprise instructions for determining a cell count or an analyte concentration based on a multivariate pattern of a detected impedance signal at one or more frequencies.

Embodiment 73. The system of embodiment 72, wherein the multivariate pattern comprises one or more of an impedance peak height, an impedance peak width, an impedance peak area, or an impedance peak half-width peak height.

Embodiment 74. The system of embodiment 72 or 73, wherein the multivariate pattern comprises a real impedance component and an imaginary impedance component.

Embodiment 75. The system of embodiment 72 or 73, wherein the multivariate pattern comprises a magnitude impedance component and a phase impedance component.

Embodiment 76. The system of any one of embodiments 67-75, wherein the one or more programs comprise instructions for calibrating the sensor.

Embodiment 77. The system of any one of embodiments 67-76, wherein the device is a handheld device.

Embodiment 78. A method of analyzing a biological sample, comprising:
depositing a biological sample into a cartridge;
transporting the biological sample within the cartridge using a plurality of electrowetting electrodes;
analyzing the biological sample using one or more sensors within the cartridge to generate analytical data; and
transmitting the analytical data from the cartridge.

Embodiment 79. The method of embodiment 78, comprising mixing the biological sample with one or more reagents within the cartridge.

Embodiment 80. The method of embodiment 78 or 79, wherein the biological sample is received by the cartridge using capillary action.

Embodiment 81. The method of any one of embodiments 78-80, further comprising transporting the biological sample into a waste reservoir within the cartridge after analyzing the biological sample.

Embodiment 82. The method of any one of embodiments 78-81, wherein the cartridge is disposed of after a single use.

Embodiment 83. The method of any one of embodiments 78-82, wherein analyzing the biological sample comprises counting a number of cells in the biological sample, wherein the analytical data relates to the number of cells.

Embodiment 84. The method of any one of embodiments 78-83, wherein analyzing the biological sample comprises comprising differentiating two or more different cell types.

Embodiment 85. The method of embodiment 84, wherein analyzing the biological sample comprises comprising differentiating between red blood cells, white blood cells, and platelets.

Embodiment 86. The method of any one of embodiments 78-85, wherein analyzing the biological sample comprises counting white blood cells, counting red blood cells, or counting platelets.

Embodiment 87. The method of any one of embodiments 78-86, wherein analyzing the biological sample comprises differentiating between eosinophils, basophils, neutrophils, monocytes, and lymphocytes.

Embodiment 88. The method of any one of embodiments 78-87, wherein analyzing the biological sample comprises counting a number of eosinophils, a number of basophils, a number of neutrophils, a number of monocytes, or a number of lymphocytes.

Embodiment 89. The method of any one of embodiments 78-88, wherein analyzing the biological sample comprises applying an electrical current to the biological sample and recording a multiplexed impedance of the electrical current.

Embodiment 90. The method of embodiment 89, wherein the electrical current is a mixed current comprising a plurality of alternating current components at different frequencies.

Embodiment 91. The method of embodiment 89 or 90, wherein the electrical current is a mixed current comprising a direct current component and a plurality of alternating current components at different frequencies.

Embodiment 92. The method of any one of embodiments 89-91, wherein the electrical current is a mixed current comprising at least five alternating current components at different frequencies.

Embodiment 93. The method of any one of embodiments 78-92, comprising self-calibrating at least one of the sensors to detect different cell sizes.

Embodiment 94. The method of any one of embodiments 78-93, wherein analyzing the biological sample comprises continuously flowing the biological sample through at least one of the sensors during analysis.

Embodiment 95. The method of any one of embodiments 78-94, wherein the biological sample is transported within the cartridge using a voltage of about 50V or less.

Embodiment 96. The method of any one of embodiments 78-95, wherein the biological sample is transported within the cartridge using a voltage of about 0.5 V to about 50V.

Embodiment 97. The method of any one of embodiments 78-96, wherein analyzing the biological sample comprises determining a concentration of an analyte or a protein within the biological sample.

Embodiment 98. The method of embodiment 97, wherein analyzing the biological sample comprises statically positioning the biological sample on at least one of the sensors.

Embodiment 99. The method of embodiment 98, wherein the biological sample is statically positioned on the sensor using electrowetting electrodes.

Embodiment 100. The method of any one of embodiments 78-99, wherein determining the concentration of the analyte or the protein within the biological sample comprises:
  binding the analyte or the protein to an affinity moiety bound to an electrode within one of the sensors, and
  measuring an impedance change resulting from the analyte or the protein binding to the affinity moiety.

Embodiment 101. The method of embodiment 100, wherein the affinity moiety is an antibody, an antibody fragment, or an aptamer.

Embodiment 102. A system, comprising
  (a) a cartridge configured to analyze a biological sample, the cartridge comprising:
    (i) a sensor comprising:
      a first channel segment;
      a second channel segment;
      a pore or a channel fluidly connecting the first channel segment and the second channel segment;
      an electrode pair configured apply a multiplexed electrical current or voltage to the pore or channel; and
      an electrode pair configured to detect impedance at a plurality of frequencies within the pore or channel, wherein the electrode pair configured to apply the multiplexed electrical current and the electrode pair configured to detect the impedance are the same electrode pair or different electrode pairs; and
    (ii) a device interface electrically connected to the sensor; and
  (b) a device configured to interface with and operate the cartridge, comprising one or more processors and a non-transitory computer-readable storage medium storing one or more programs configured to be executed by the one or more processors, the one or more programs comprising instructions for determining a cell count or an analyte concentration based on the detected impedance, wherein the detected impedance comprises at least a first multivariate impedance pattern at a first frequency and a second multivariate impedance pattern at a second frequency.

Embodiment 103. The system of embodiment 102, wherein the electrode pair configured to apply the multiplexed electrical current and the electrode pair configured to detect the impedance are the same electrode pair.

Embodiment 104. The system of embodiment 102, wherein the electrode pair configured to apply the multiplexed electrical current and the electrode pair configured to detect the impedance are different electrode pairs.

Embodiment 105. The system of any one of embodiments 102-104, wherein the first multivariate impedance pattern and the second multivariate impedance pattern each comprise a real component and an imaginary component of the impedance.

Embodiment 106. The system of any one of embodiments 102-104, wherein the first multivariate impedance pattern and the second multivariate impedance pattern each comprise a magnitude component and phase imaginary component of the impedance.

Embodiment 107. The system of any one of embodiments 102-106, wherein the first multivariate impedance pattern and the second multivariate impedance pattern comprises one or more of an impedance peak height, an impedance peak width, an impedance peak area, or an impedance peak half-width peak height.

Embodiment 108. The system of any one of embodiments 102-107, wherein the electrode pair is in direct contact with an inner portion of the channel.

Embodiment 109. The system of any one of embodiments 102-108, wherein the sensor is configured to count a number of cells in the biological sample.

Embodiment 110. The system of embodiment 109, wherein the sensor is configured to differentiate between different types of cells.

Embodiment 111. The system of embodiment 110, wherein the sensor is configured to differentiate between red blood cells, white blood cells, and platelets.

Embodiment 112. The system of any one of embodiments 109-111, wherein the sensor is configured to count a number of red blood cells, a number of white blood cells, or a number of platelets.

Embodiment 113. The system of any one of embodiments 109-112, wherein the sensor is configured to differentiate between eosinophils, basophils, neutrophils, monocytes, and lymphocytes.

Embodiment 114. The system of any one of embodiments 109-113, wherein the sensor is configured to count a number of eosinophils, basophils, neutrophils, monocytes, and lymphocytes.

Embodiment 115. The system of any one of embodiments 109-114, where the pore or channel is a micropore or a microchannel.

Embodiment 116. The system of any one of embodiments 102-108, wherein the sensor is configured to detect an analyte concentration.

Embodiment 117. The system of embodiment 116, wherein the analyte is a protein.

Embodiment 118. The system of embodiment 116 or 117, wherein the pore or channel is a nanopore or a nanochannel.

Embodiment 119. The system of any one of embodiments 102-118, wherein the electrode pair configured to detect impedance comprises a first electrode within the first channel segment, and a second electrode within the second channel segment.

Embodiment 120. The system of any one of embodiments 102-119, wherein the sensor comprises the channel, and wherein the electrode pair configured to detect impedance is positioned within the channel.

Embodiment 121. The system of embodiment 120, wherein the electrode pair comprises a first electrode proximal to the first channel segment, and a second electrode proximal to the second channel segment.

Embodiment 122. The system of embodiment 121, wherein the electrode pair comprises a first electrode on an upper surface of the channel, and a second electrode on a lower surface of the channel, and wherein the first electrode is positioned above the second electrode.

Embodiment 123. The system of any one of embodiments 102-122, wherein the sensor further comprises an electrode pair configured to detect liquid flow within the sensor.

Embodiment 124. The system of any one of embodiments 102-123, wherein the sensor comprises one or more isolation electrodes.

Embodiment 125. The system of any one of embodiments 102-124, wherein the sensor comprises an entrance to the first channel segment proximal to an electrowetting electrode.

Embodiment 126. The system of any one of embodiments 102-125, wherein the sensor comprises an exit to the second channel segment proximal to an electrowetting electrode.

Embodiment 127. The system of any one of embodiments 102-126, wherein the multiplexed electrical current comprises a plurality of alternating current components at different frequencies.

Embodiment 128. The system of any one of embodiments 102-127, wherein the multiplexed electrical current comprises a (1) a direct current component or a low-frequency alternating current, and (2) a plurality of alternating current components at different frequencies.

Embodiment 129. The system of embodiment 127 or 128, wherein the plurality of alternating current components comprises at least three alternating current components.

Embodiment 130. The system of embodiment 129, wherein the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz.

Embodiment 131. The system of embodiment 127 or 128, wherein the plurality of alternating current components comprises at least five alternating current components.

Embodiment 132. The system of embodiment 131, wherein the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz.

Embodiment 133. The system of any one of embodiments 102-132, wherein the electrode pair configured to detect impedance is configured to detect impedance at a sampling rate of about 100 kHz or more.

Embodiment 134. The system of any one of embodiment 102-133, wherein the cartridge comprises a plurality of electrowetting electrodes configured to transport one or more liquids within the cartridge.

Embodiment 135. The system of any one of embodiment 102-134, wherein the cartridge is configured to mix a reagent with the biological sample or a subsample derived therefrom, and transport the biological sample or subsample to the sensor.

Embodiment 136. A method of determining a cell count in a biological sample, comprising:
transporting the biological sample through a sensor comprising a channel or pore;
applying a multiplexed electrical current or voltage to the channel or pore;
detecting a multiplexed impedance within the channel or pore, the multiplexed impedance comprising at least a first multivariate impedance pattern at a first frequency and a second multivariate impedance pattern at a second frequency; and
determining a cell count based on the detected multiplexed impedance.

Embodiment 137. The method of embodiment 136, wherein the first multivariate impedance pattern and the second multivariate impedance pattern each comprise a real component and an imaginary component.

Embodiment 138. The method of embodiment 136, wherein the first multivariate impedance pattern and the second multivariate impedance pattern each comprise a magnitude component and a phase component.

Embodiment 139. The method of anyone of embodiments 136-138, wherein the multivariate impedance pattern comprises one or more of an impedance peak height, an impedance peak width, an impedance peak area, or an impedance peak half-width peak height.

Embodiment 140. The method of any one of embodiments 136-139, wherein the biological sample directly contacts a pair of electrodes that detect the multiplexed impedance.

Embodiment 141. The method of any one of embodiments 136-140, comprising differentiating between two or more different types of cells.

Embodiment 142. The method of any one of embodiments 136-141, wherein determining the cell count comprises determining a red blood cell count, a white blood cell count, or a platelet count in the biological sample.

Embodiment 143. The method of any one of embodiments 136-142, wherein determining the cell count comprises determining an eosinophil count, a basophil count, a neutrophil count, a monocyte count, and a lymphocyte count in the biological sample.

Embodiment 144. The method of any one of embodiments 136-143, comprising transporting two or more subsamples of the biological sample through the sensor, wherein the two or more subsamples are processed at different pH levels or different electrolyte concentrations.

Embodiment 145. The method of any one of embodiments 136-144, comprising transporting a marker into the sensor.

Embodiment 146. The method of embodiments 145 wherein the marker is an air bubble or a low-conductivity solution.

Embodiment 147. The method of embodiment 145 or 146, comprising detecting the marker.

Embodiment 148. The method of any one of embodiments 136-147, wherein the marker triggers initiating or terminating recordation of the detected multiplexed impedance.

Embodiment 149. The method of any one of embodiments 136-148, comprising determining a flow rate of the biological sample.

Embodiment 150. The method embodiment 149, comprising using the determined flow rate to determine the cell count.

Embodiment 151. The method of any one of embodiments 136-150, comprising filtering the biological sample.

Embodiment 152. The method of any one of embodiments 136-151, wherein the multiplexed electrical current comprises a plurality of alternating current components at different frequencies.

Embodiment 153. The method of any one of embodiments 136-152 wherein the multiplexed electrical current comprises a (1) a direct current component or a low-frequency alternating current, and (2) a plurality of alternating current components at different frequencies.

Embodiment 154. The method of embodiment 152 or 153, wherein the plurality of alternating current components comprises at least three alternating current components.

Embodiment 155. The method of embodiment any one of embodiments 152-154, wherein the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz.

Embodiment 156. The system of any one of embodiments 152 or 153, wherein the plurality of alternating current components comprises at least five alternating current components.

Embodiment 157. The system of embodiment 156, wherein the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz.

Embodiment 158. A method of detecting an analyte in a biological sample, comprising:
transporting the biological sample through a sensor comprising a channel or pore, the biological sample comprising an analyte bound to an affinity moiety;
applying an electrical current or voltage to the channel or pore;
detecting an impedance within the channel or pore; and
detecting the analyte based on the detected impedance.

Embodiment 159. The method of embodiment 158, wherein the analyte is a protein or an electrolyte.

Embodiment 160. The method of embodiment 158 or 159, wherein the affinity moiety is a multivalent affinity moiety.

Embodiment 161. The method of any one of embodiments 158-160, wherein the affinity moiety is charged.

Embodiment 162. The method of any one of embodiments 158-151, wherein the affinity moiety comprises an aptamer, an antibody, or an antibody fragment.

Embodiment 163. The method of any one of embodiments 158-162, wherein the affinity moiety comprises an aptamer bound to an avidin or an avidin derivative.

Embodiment 164. The method of any one of embodiments 158-163, comprising mixing the biological sample with a reagent comprising the affinity moiety.

Embodiment 165. The method of any one of embodiments 158-164, wherein detecting the analyte based on the detected impedance comprises distinguishing between an affinity moiety bound to the analyte and an unbound affinity moiety.

Embodiment 166. The method of any one of embodiments 158-165, comprising transporting a marker into the sensor.

Embodiment 167. The method of embodiments 166, wherein the marker is an air bubble or a low-conductivity solution.

Embodiment 168. The method of embodiment 166 or 167, comprising detecting the marker.

Embodiment 169. The method of any one of embodiments 166-168, wherein the marker triggers initiating or terminating recordation of the detected multiplexed impedance.

Embodiment 170. The method of any one of embodiments 166-169, comprising determining a flow rate of the biological sample.

Embodiment 171. The method embodiment 170, comprising using the determined flow rate to determine a concentration of the analyte.

Embodiment 172. An electrowetting electrode array, comprising:
a plurality of coplanar electrowetting electrodes coated with and spaced by an insulating layer;
wherein the electrowetting array comprises a hydrophobic liquid contact surface, and wherein the electrowetting array is configured to transport an aqueous liquid using a voltage of about 50 volts or less.

Embodiment 173. The electrowetting electrode array of embodiment 172, wherein the insulating layer comprises the hydrophobic liquid contact surface.

Embodiment 174. The electrowetting electrode array of embodiment 173, wherein the insulating layer comprises a nanostructured surface.

Embodiment 175. The electrowetting electrode array of embodiment 172, wherein the insulating layer is coated with a hydrophobic layer comprising the hydrophobic liquid contact surface.

Embodiment 176. The electrowetting electrode array of embodiment 175, wherein the hydrophobic layer comprises a nanostructured surface.

Embodiment 177. The electrowetting electrode array of embodiment 175 or 176, wherein the hydrophobic layer comprises a fluoropolymer, polydimethylsiloxane, a parylene, octadecanehydroxamic acid, stearic acid, octadecanephosphonic acid, 16-hydroryhexadecanehydroramic acid, or octadecanethiol.

Embodiment 178. The electrowetting electrode array of any one of embodiments 172-177, wherein the plurality of electrowetting electrodes is configured to transport the aqueous liquid using a voltage of about 0.5 volts to about 50 volts.

Embodiment 179. The electrowetting electrode array of any one of embodiments 172-178, wherein the insulating layer has a dielectric constant of about 3.9 or higher.

Embodiment 180. The electrowetting electrode array of any one of embodiments 172-179, wherein the insulating layer comprises hafnium oxide, barium strontium titanate, or strontium titanate, silica, or silicon nitride.

Embodiment 181. The electrowetting electrode array of any one of embodiments 171-180, wherein the insulating layer is coated on the electrode using atomic layer deposition, chemical vapor deposition, reactive ion beam deposition, sputter deposition, evaporation, spray deposition, spin coating, or sol-gel formation.

Embodiment 182. The electrowetting electrode array of any one of embodiments 171-181, wherein the insulating layer has a thickness of about 1 nm to about 5 µm.

Embodiment 183. The electrowetting electrode array of any one of embodiments 171-182, wherein the electrowetting electrodes comprise gold, silver, silver chloride, platinum, indium tin oxide, or a conductive carbon.

Embodiment 184. The electrowetting electrode array of any one of embodiments 171-183, wherein the electrowetting electrodes are separated from the hydrophobic liquid contact surface by about 1 nm to about 25 µm.

Embodiment 185. The electrowetting electrode array of any one of embodiments 171-184, wherein the plurality of electrowetting electrodes further comprises a ground electrode parallel to the coplanar electrowetting electrodes, wherein the hydrophobic liquid contact surface is between the ground electrode and the coplanar electrowetting electrodes.

Embodiment 186. The electrowetting electrode array of embodiment 185, wherein the ground electrode is common to two or more of the electrowetting electrodes.

Embodiment 187. The electrowetting electrode array of embodiment 185, wherein at least one of the electrowetting electrodes is paired with an individual ground electrode.

Embodiment 188. The electrowetting electrode array of any one of embodiments 171-187, comprising an impedance sensor comprising a sensing electrode and a functionalized liquid contact surface, wherein the functionalized liquid contact surface is functionalized with an affinity moiety that specifically binds a target analyte.

Embodiment 189. The electrowetting electrode of embodiment 188, wherein the sensor further comprises a second sensing electrode paired with the first sensing electrode, wherein the sensor is configured to detect a change in impedance upon binding of an analyte or a protein to the affinity moiety.

Embodiment 190. The electrowetting electrode array of embodiments 188 or 189, wherein the target analyte is a protein.

Embodiment 191. The electrowetting electrode array of any one of embodiments 188-190, wherein the affinity moiety is an antibody, an antibody fragment, or an aptamer.

Embodiment 192. The electrowetting electrode array of any one of embodiments 188-191, wherein the impedance sensor further comprises a metal oxide semiconductor capacitor (MOSCap) sensor comprising a pH-sensitive or ion-sensitive layer configured to modulate impedance based on pH or ion concentration.

Embodiment 193. The electrowetting electrode array of any one of embodiments 172-192, wherein the aqueous liquid comprises a biological sample.

Embodiment 194. The electrowetting electrode array of embodiment 193, wherein the biological sample comprises a blood sample.

Embodiment 195. A cartridge for analyzing a biological sample, comprising:
a sample receiving port configured to receive the biological sample;
a sensor configured to analyze the biological sample;
a cartridge space in fluid communication with the biological sample receiving port and the sensor, the cartridge space comprising the electrowetting electrode array of any one of embodiments 172-194; and
a device interface configured to receive power from and communicate with a cartridge interface on a device, wherein the sensor and the plurality of electrowetting electrodes are in electrical communication with the device interface.

Embodiment 196. The cartridge of embodiment 195, wherein the cartridge space is fluidly connected to one or more reagent reservoirs, wherein the electrowetting electrode array extends into the one or more reagent reservoirs.

Embodiment 197. The cartridge of embodiment 195 or 196, wherein the electrowetting electrode array comprises a reagent mixing region.

Embodiment 198. The cartridge of any one of embodiments 195-197, wherein the cartridge space is a chamber or a channel.

Embodiment 199. A system for analyzing a biological sample, comprising:
the cartridge of any one of embodiments 195-198; and
a device comprising a cartridge interface configured to interface with the cartridge, the device configured to operate the electrowetting electrode array.

Embodiment 200. The system of embodiment 199, wherein the device is a handheld device.

Embodiment 201. A method of transporting a liquid, comprising:
positioning an aqueous liquid on a first hydrophobic liquid contact surface above an inactivated first electrowetting electrode; and
activating a second electrowetting electrode by applying a voltage of about 50 volts or less to the second electrowetting electrode, thereby transporting the aqueous liquid from the first hydrophobic liquid contact surface to a second hydrophobic liquid contact surface above the second electrowetting electrode;
wherein the first electrowetting electrode and the second electrowetting electrode are coated with and separated by an insulating layer.

Embodiment 202. The method of embodiment 201, wherein the aqueous liquid comprises a biological sample.

Embodiment 203. The method of embodiment 201 or 202, comprising transporting a reagent to the second liquid contacting surface, thereby mixing the reagent with the aqueous liquid.

Embodiment 204. The method of embodiment 203, wherein the reagent is transported by activating the second electrowetting electrode.

Embodiment 205. The method of any one of embodiments 201-204, wherein the biological sample is transported within the cartridge using a voltage of about 0.5 V to about 50V.

Embodiment 206. The method of any one of embodiments 201-205, wherein the first hydrophobic liquid contact surface or the second hydrophobic liquid contact surface is a nanostructured surface.

Embodiment 207. The method of any one of embodiments 201-206, wherein the insulating layer comprises the first hydrophobic liquid contact surface and the second hydrophobic liquid contact surface.

Embodiment 208. The method of any one of embodiments 201-207, wherein the insulating layer is coated with a hydrophobic layer comprising the first hydrophobic liquid contact surface and the second hydrophobic liquid contact surface.

Embodiment 209. The method of embodiment 208, wherein the hydrophobic layer comprises a fluoropolymer, polydimethylsiloxane, a parylene, octadecanehydroxamic acid, stearic acid, octadecanephosphonic acid, 16-hydroryhexadecanehydroramic acid, or octadecanethiol.

Embodiment 210. The method of any one of embodiments 201-209, wherein the insulating layer has a dielectric constant of about 3.9 or higher.

Embodiment 211. The method of any one of embodiments 201-210, wherein the insulating layer comprises hafnium oxide, barium strontium titanate, or strontium titanate, silica, or silicon nitride.

Embodiment 212. The method of any one of embodiments 201-211, wherein the insulating layer has a thickness of about 1 nm to about 5 µm.

Embodiment 213. The method of any one of embodiments 201-212, wherein the first electrowetting electrode is separated from the first hydrophobic liquid contact surface by about 1 nm to about 25 µm, and the second electrowetting electrode is separated from the second hydrophobic liquid contact surface by about 1 nm to about 25 µm.

Embodiment 214. A metal oxide semiconductor capacitor (MOSCap) sensor, comprising:
a first sensor segment comprising a first electrode and a first semiconductor layer;
a second sensor segment comprising a second electrode and a second semiconductor layer; and
a space between the first sensor segment and the second sensor segment configured to allow liquid flow;

wherein the first sensor segment, second sensor segment, and the space are in a stacked configuration.

Embodiment 215. The MOSCap sensor of embodiment 214, wherein the first semiconductor layer is directly coated onto the first electrode, and the second semiconductor layer is directly coated onto the second electrode.

Embodiment 216. The MOSCap sensor of embodiment 214 or 215, wherein the first sensor segment comprises a first insulating layer, and the second sensor segment comprises a second insulating layer.

Embodiment 217. The MOSCap sensor of embodiment 216, wherein the first insulating layer is directly coated onto the first semiconductor layer, and the second insulating layer is directly coated onto the second semiconductor layer.

Embodiment 218. The MOSCap sensor of any one of embodiments 214-217, wherein the first sensor segment comprises a first impedance modulation layer, and the second sensor segment comprises a second impedance modulation layer, wherein the first impedance modulation layer and the second impedance modulation layers are pH-sensitive or ion-sensitive layers configured to modulate impedance based on pH or ion concentration.

Embodiment 219. The MOSCap sensor of embodiment 218, wherein the first sensor segment comprises a first insulating layer, and the second sensor segment comprises a second insulating layer; and wherein the first impedance modulation layer is directly coated onto the first insulating layer, and the second impedance modulation layer is directly coated onto the second insulating layer.

Embodiment 220. The MOSCap sensor of any one of embodiments 214-219, wherein the first electrode is attached to a first substrate, and the second electrode is attached to a second substrate.

Embodiment 221. The MOSCap sensor of any one of embodiments 214-220, wherein the first sensor segment is adjacent to a reference electrode.

Embodiment 222. The MOSCap sensor of embodiment 221, wherein the first sensor segment is adjacent to a counter electrode.

Embodiment 223. The MOSCap sensor of any one of embodiments 214-222, wherein the MOSCap sensor is adjacent to an electrowetting electrode.

Embodiment 224. The MOSCap sensor of embodiment 223, wherein the electrowetting electrode is functionalized with an affinity moiety.

Embodiment 225. The MOSCap sensor of embodiment 224, wherein the affinity moiety specifically binds hemoglobin.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the devices and methods described herein.

Example 1: Cell Size Differentiation Using Flow Cytometer Channel Sensor

Figure 18A:
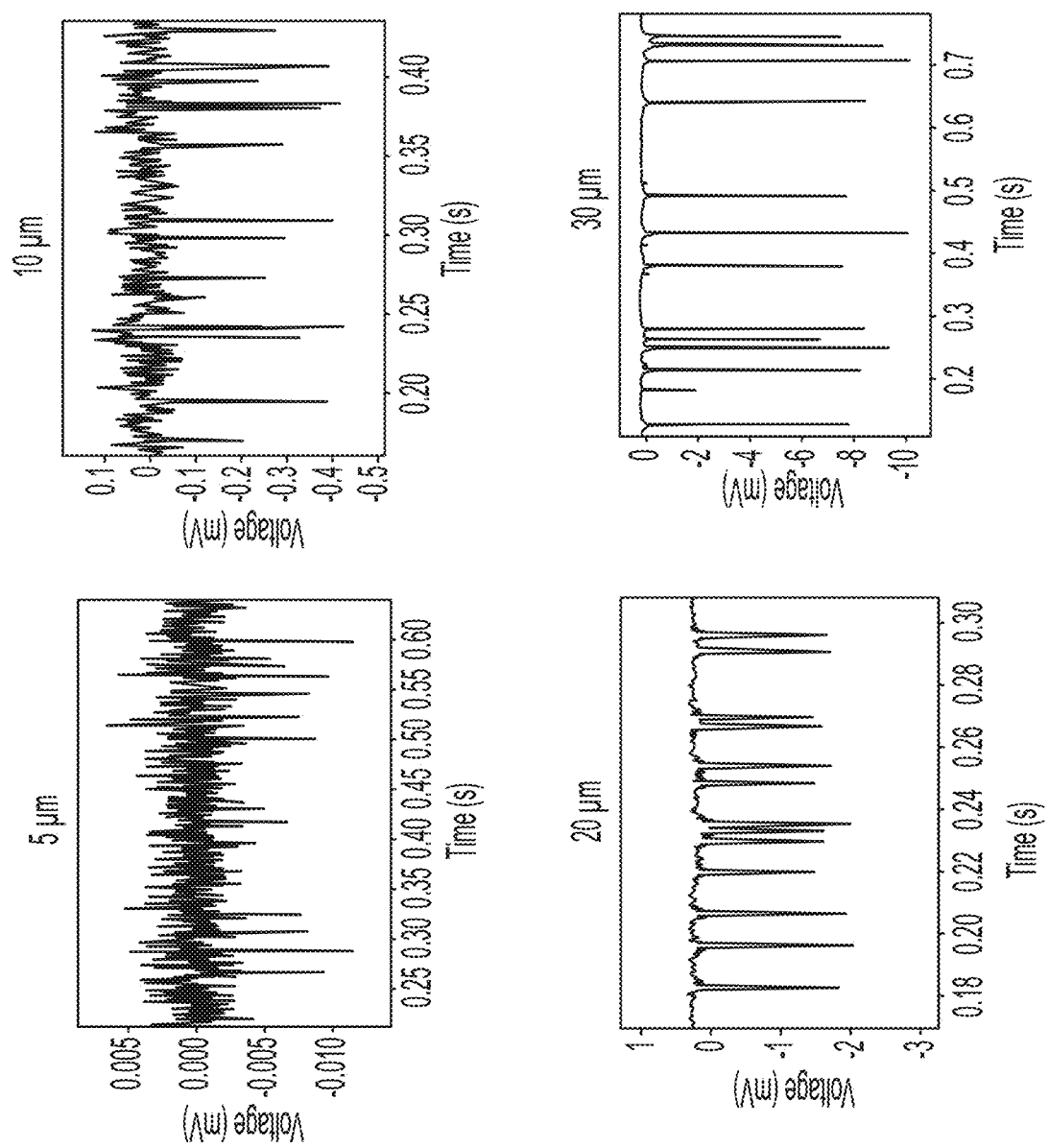
FIG. 18A shows the voltage change in a flow cytometer as polystyrene beads with a diameter of 5 µm, 10 µm, 20 µm, or 30 µm flow through a 30 kHz current. A significant voltage drop is observed as the beads pass through the current, which can be used to measure the particle size.

The diameter of cells flowing through flow cytometer can be determined using a low frequency current (e.g., <100 Hz), and the voltage signal can be calibrated to signal modulations detected using polystyrene beads with known sizes. To calibrate the sensor, polystyrene beads with a diameter of 5 µm, 10 µm, 20 µm, or 30 µm suspended in phosphate buffered saline, pH 7.4, were passed through a flow cytometer channel sensor. A 30 kHz current (0.35 $V_{pk}$) was passed through the sensor and impedance was sampled at a rate of 460,000 samples per second. The change in voltage against time is shown in FIG. 18A for each of the particle sizes, with each peak reflecting the passage of a single particle.

Figure 18B:
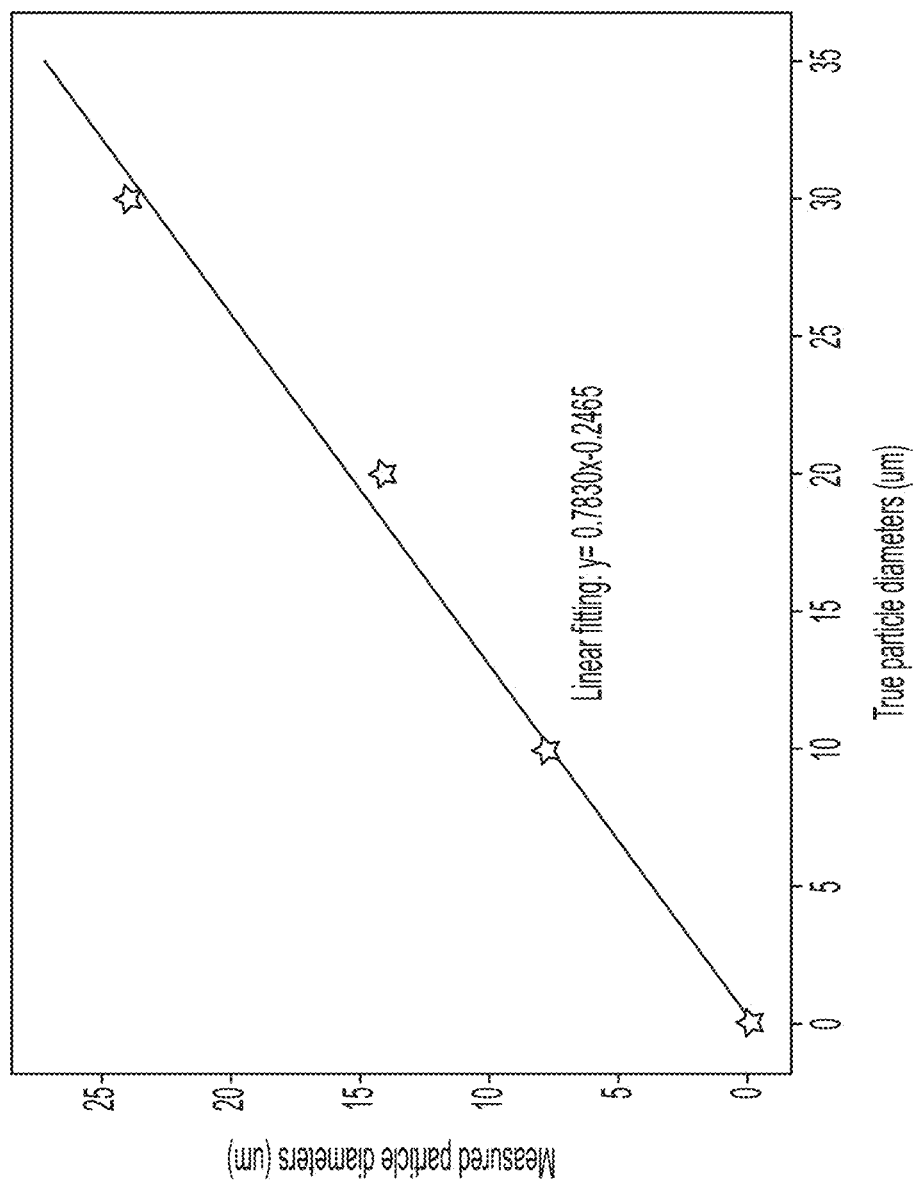
FIG. 18B shows a normalization curve of the measured diameter of polystyrene beads using the flow cytometer (30 kHz current) against the actual size of the polystyrene beads. The measured diameter fits linearly as a function of the actual diameter, indicating that this method can be reliably used to estimate particle size.

Measured particle size was normalized to the true particle size, as shown in FIG. 18B, to calibrate the measurements. The different particle sizes fit linearly, and a calibration for future measurements using this flow cytometer channel sensor was set using the linear fit. To determine or calculate size from the measured voltage signal, change in voltage with respect to baseline signal (without particle) was converted to change in impedance. This change in impedance was converted to particle size using the theoretical relationship between the channel dimensions to change in impedance, given as:

$$\frac{\Delta Z}{Z} = \frac{d^3}{LD^2}\left[\frac{D^2}{2L^2} + \frac{1}{\sqrt{1+\frac{D}{2L^2}}}\right] \times F\left(\frac{d^3}{D^3}\right)$$

where $\Delta Z$ is the change in impedance with regard to the baseline impedance Z without particles; d, L, D are the particle diameter, channel length and channel diameters respectively.

$$F\left(\frac{d^3}{D^3}\right)$$

is a correction factor.

Figure 19:
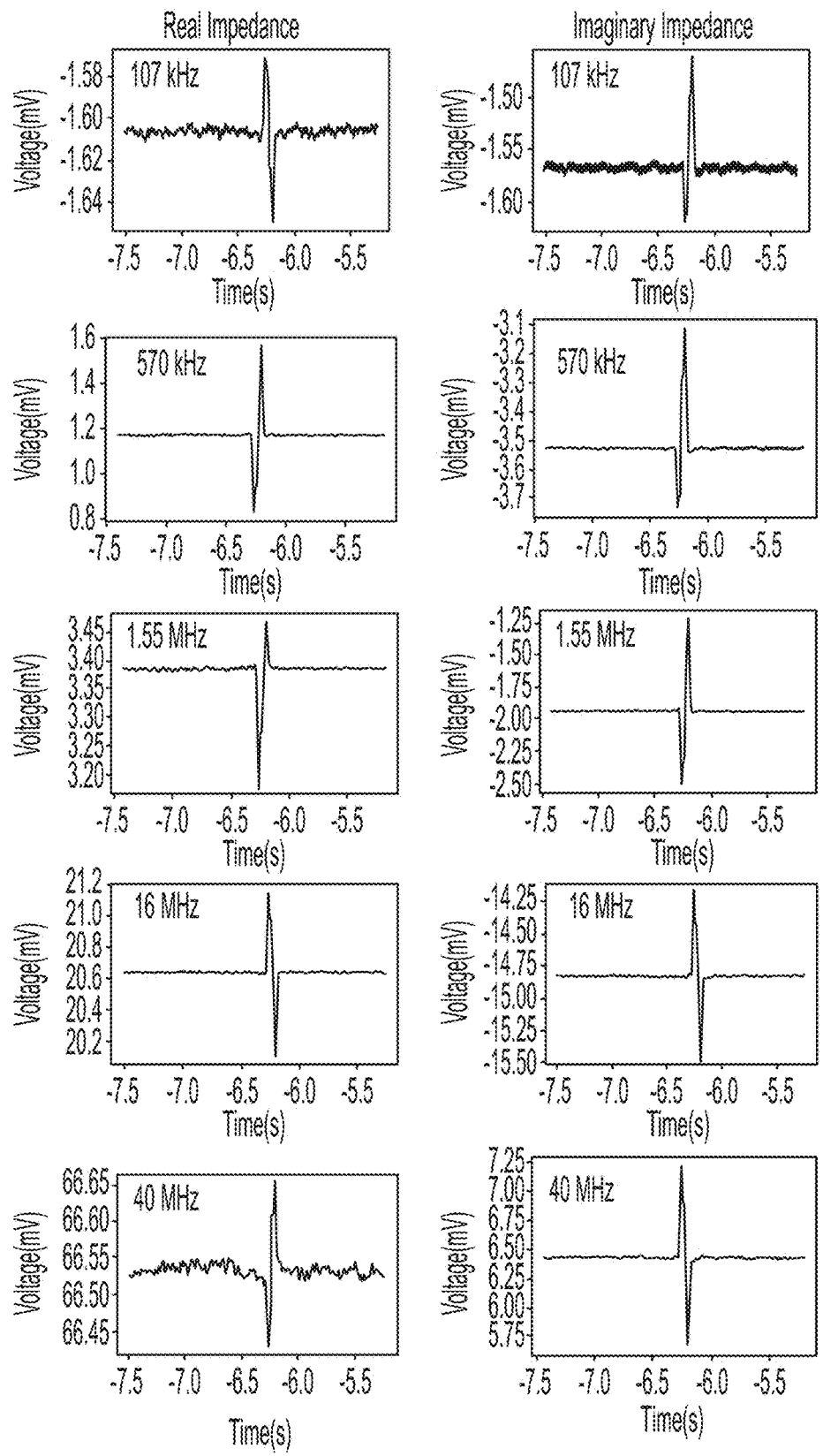
FIG. 19 shows the real and imaginary components of measured multiplexed impedance at current having 107 kHz, 570 kHz, 1.55 MHz, 16 MHz, and 40 MHz components for a eosinophil as it passes through the current at −6.19 seconds.
Figure 20A:
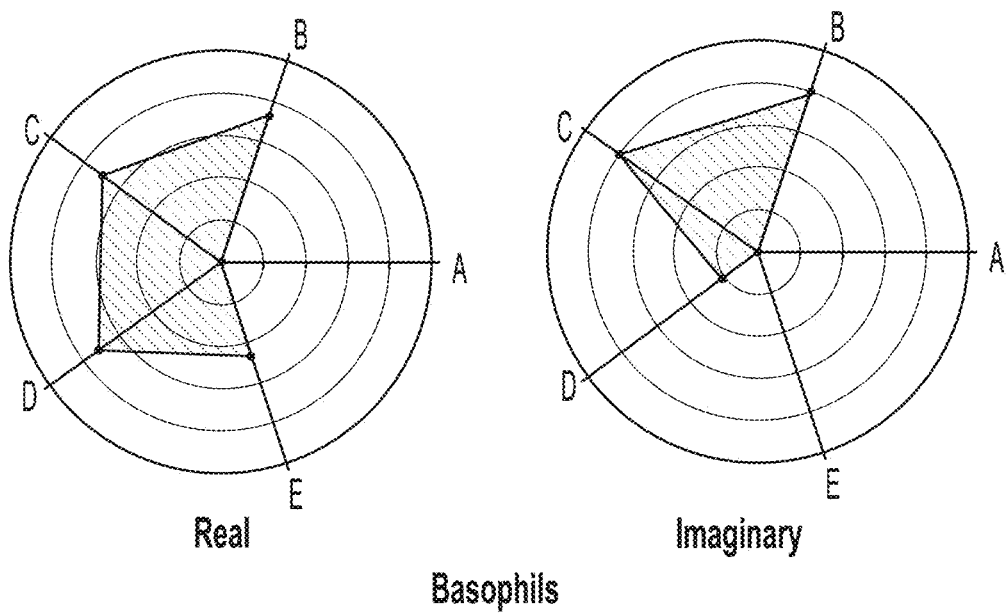
FIG. 20A-G shows plots of average normalized impedances for real and imaginary components at various currents (107 kHz, 570 kHz, 1.55 MHz, 16 MHz, and 40 MHz) for basophils (FIG. 20A), eosinophils (FIG. 20B), lymphocytes (FIG. 20C), monocytes (FIG. 20D, neutrophils (FIG. 20E), platelets (FIG. 20F), and red blood cells (FIG. 20G).
Figure 20B:
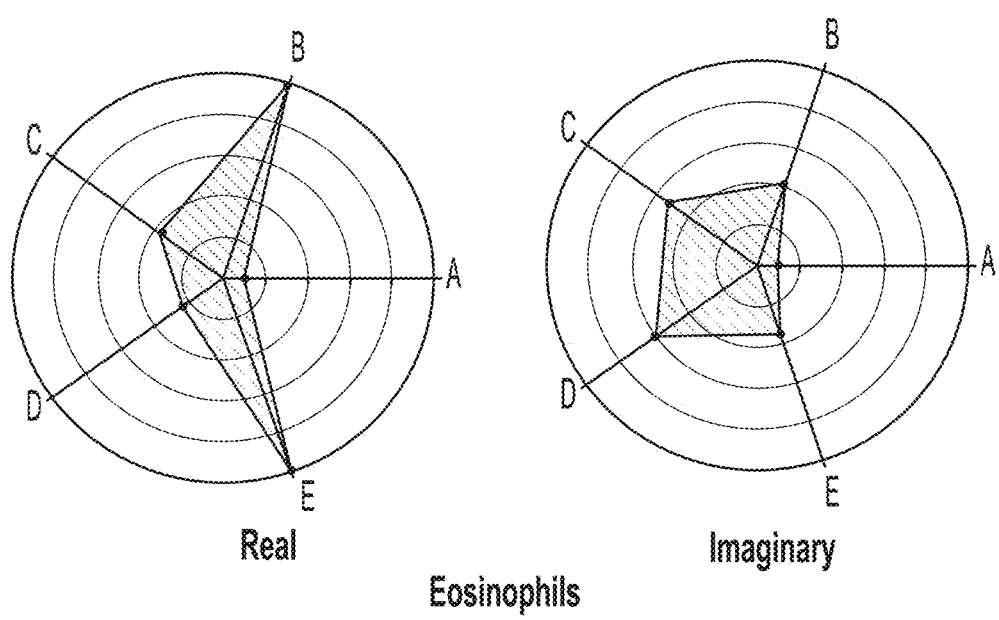
Figure 20C:
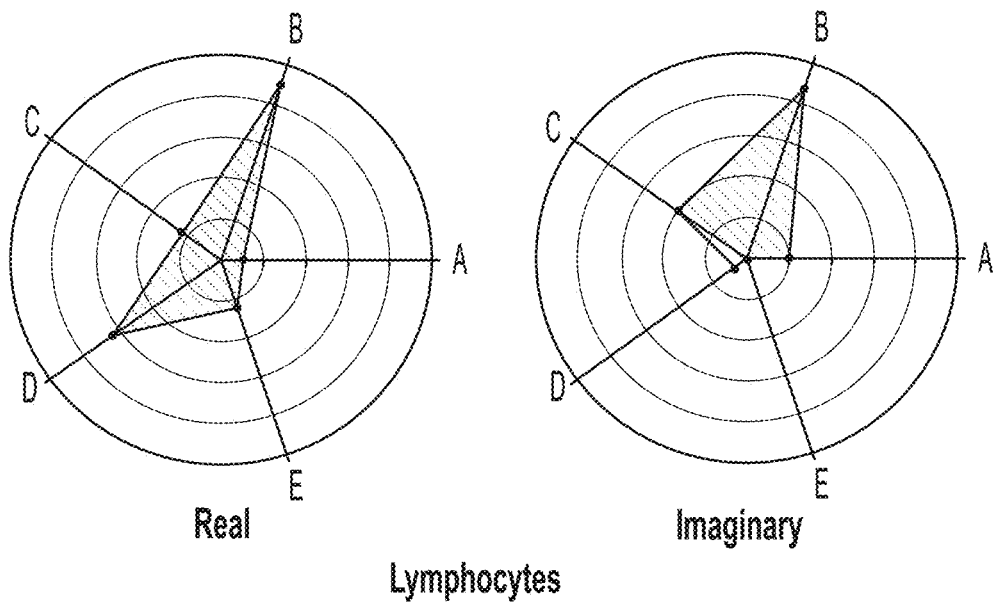
Figure 20D:
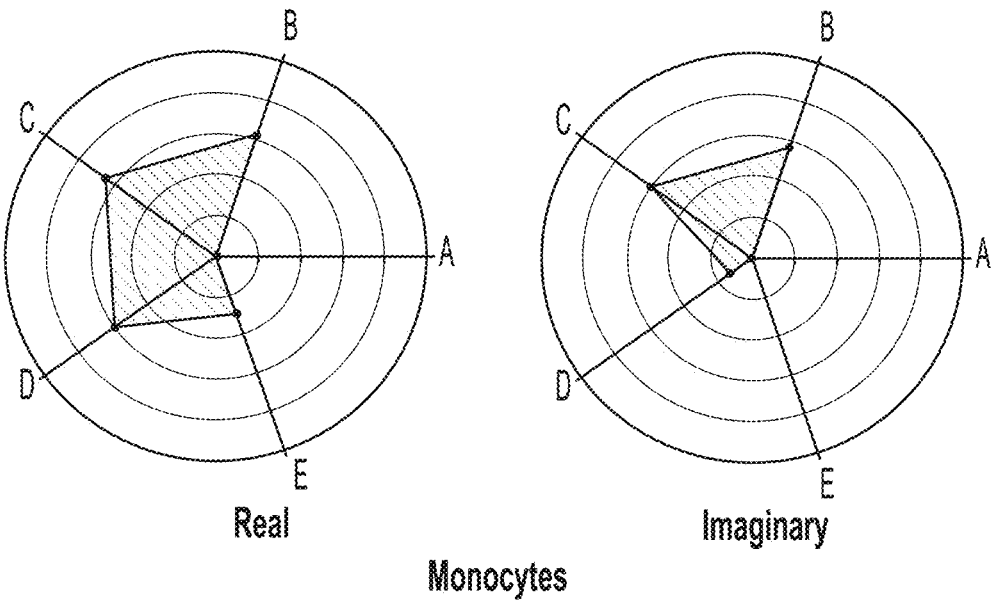
Figure 20E:
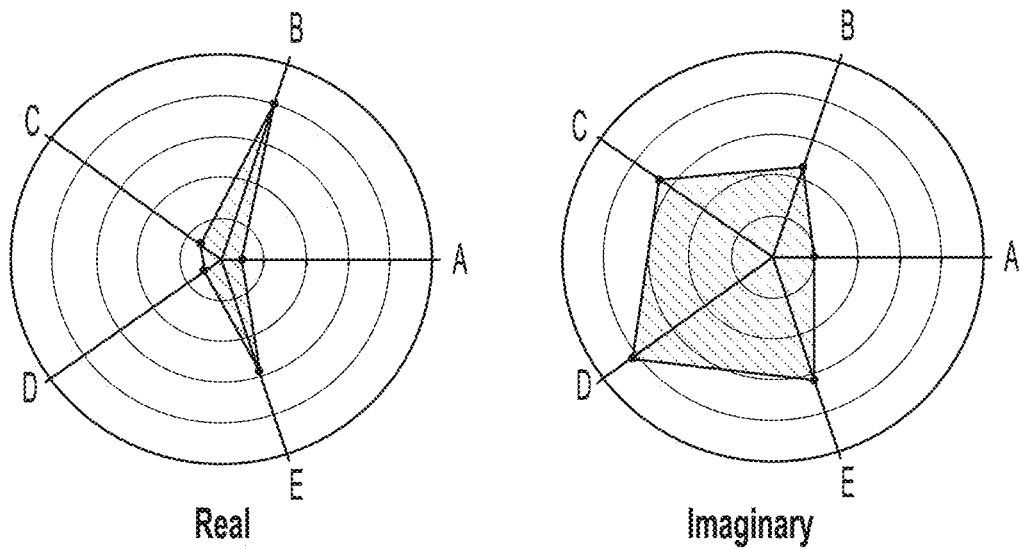
Figure 20F:
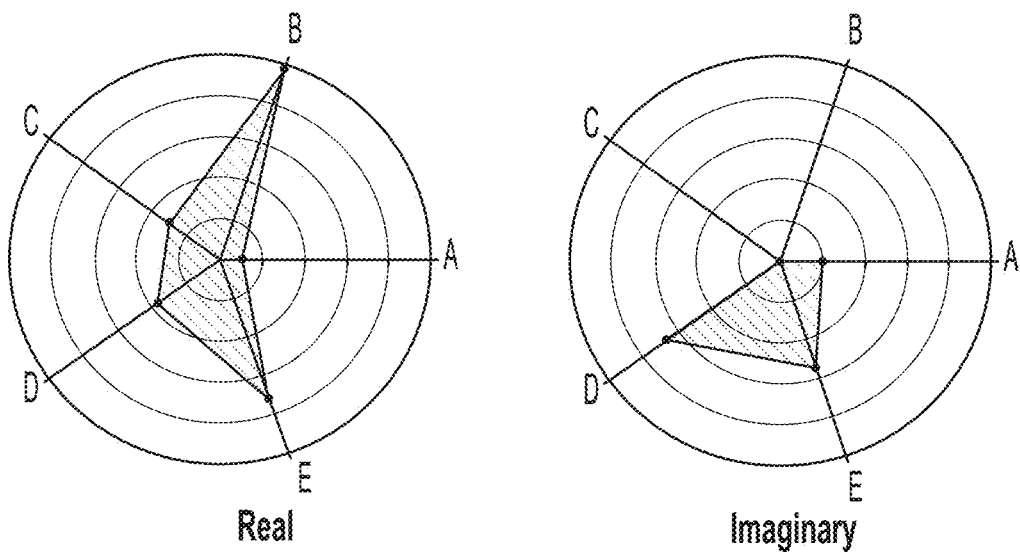
Figure 20G:
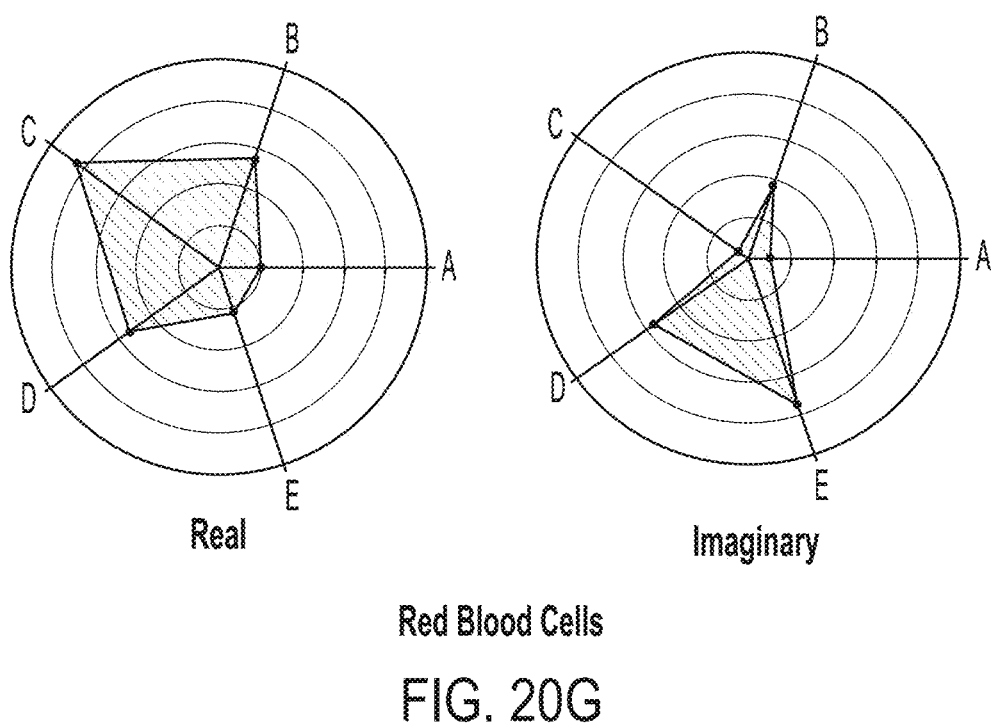

Example 2: Determination of Multiplexed Impedance Signatures for Various Cell Types Impedance signatures for red blood cells, platelets, eosinophils, basophils, neutrophils, monocytes, and lymphocytes were measured by isolating the various cell types and passing the cells through a flow cytometer channel sensor while measuring impedance. The different cell types were isolated using known techniques. Isolated cells were suspended in phosphate buffered saline, pH 7.4, and passed through the flow cytometer. A multiplexed current (0.35 $V_{pk}$) that included a low frequency component (30 kHz) for size detection, and five additional frequencies (107 kHz, 570 kHz, 1.55 MHz, 16 MHz, and 40 MHz) was passed through the flow sensor and real and imaginary components of the impedance were detected. The impedance signal was sampled at a rate of 460,000 samples per second, and the different impedance frequencies were filtered and demodulated using a bandpass filter (8th order, 5 Hz bandwidth). Exemplary real and imaginary impedances for a single eosinophil at all 5 frequencies are shown in FIG. 19, with the cell flowing through the current at −6.19 seconds. Similar plots were collected for the other cell types, although the data is not show. The impedance signals were normalized by dividing the magnitude at 107 kHz signal across all measurements (although the data could equally be normalized to any of the other frequencies), and average normalized impedances for real and imaginary impedance components at the five different frequencies for the different cell types are shown in FIG. 20A (basophils), FIG. 20B (eosinophils), FIG. 20C (lymphocytes), FIG. 20D (monocytes), FIG. 20E (neutrophils), FIG. 20F (platelets), FIG. 20G (red blood cells), and Table 1. In FIGS. 20A-20G, points A-E on the radar plot corresponds to frequencies 107 kHz, 570 kHz, 1.55 MHz, 16 MHz and 40 MHz respectively.

TABLE 1

Normalized Impedance Amplitude Signatures

| Cell Type | 107 kHz | | 570 kHz | | 1.55 MHz | | 16 MHz | | 40 MHz | |
|---|---|---|---|---|---|---|---|---|---|---|
| | Real | Imag. | Real | Imag. | Real | Imag. | Real | Imag. | Real | Imag. |
| Red Blood Cells | 1 | 1 | 2.72 | 3.78 | 4.26 | 0.58 | 2.70 | 5.49 | 1.12 | 7.57 |
| Platelets | 1 | 1 | 9.76 | 0 | 3.03 | 0 | 3.67 | 3.29 | 7.17 | 2.74 |
| Eosinophils | 1 | 1 | 9.72 | 4.22 | 3.73 | 5.22 | 2.34 | 5.99 | 10.06 | 3.53 |
| Basophils | 1 | 1 | 36.34 | 78.52 | 34.57 | 81.30 | 35.83 | 21.37 | 23.42 | 2.63 |
| Neutrophils | 1 | 1 | 7.93 | 2.35 | 1.22 | 3.3 | 1.01 | 4.11 | 5.74 | 3.14 |
| Monocytes | 1 | 1 | 63.03 | 57.20 | 64.77 | 60.21 | 58.81 | 13.07 | 28.93 | 1.98 |
| Lymphocytes | 1 | 1 | 8.96 | 4.37 | 2.30 | 2.01 | 6.39 | 0.41 | 2.47 | 0.05 |

These impedance signatures are determined in single environmental conditions such as pH, ionic concentrations of buffer etc. By tuning and modifying the environmental variables such as pH, ionic concentrations, the environmental conditions affect both the surface and bulk properties of the cells, as well as measurements under these conditions. Therefore, additional impedance signatures can be collected under different buffer conditions to provide more unique characteristics of the various cell types.

Example 3: Sorting Particle Sizes in a Flow Sensor

Figure 21A:
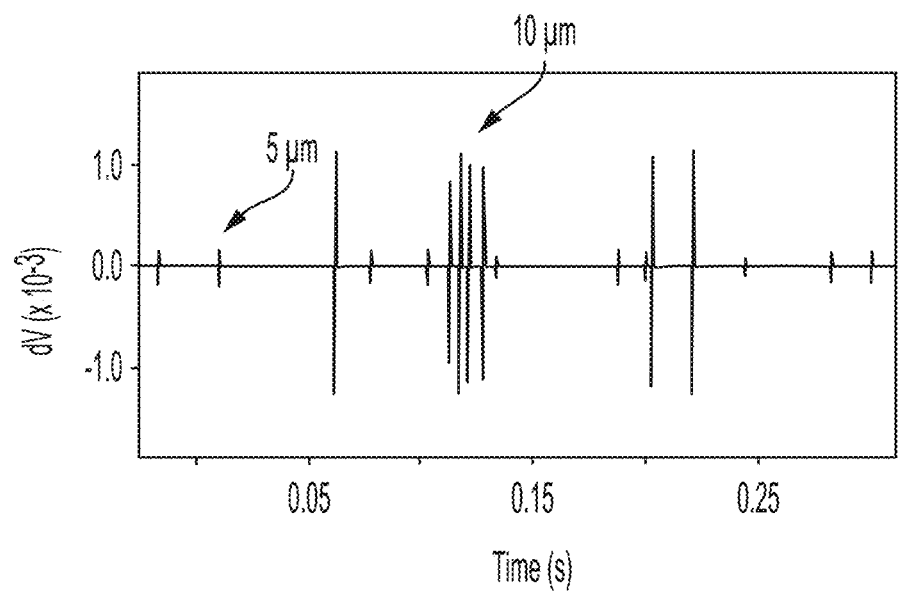
FIG. 21A shows a normalized voltage differential signal from 5 µm and 10 µm polystyrene beads flowing through a channel sensor.
Figure 21B:
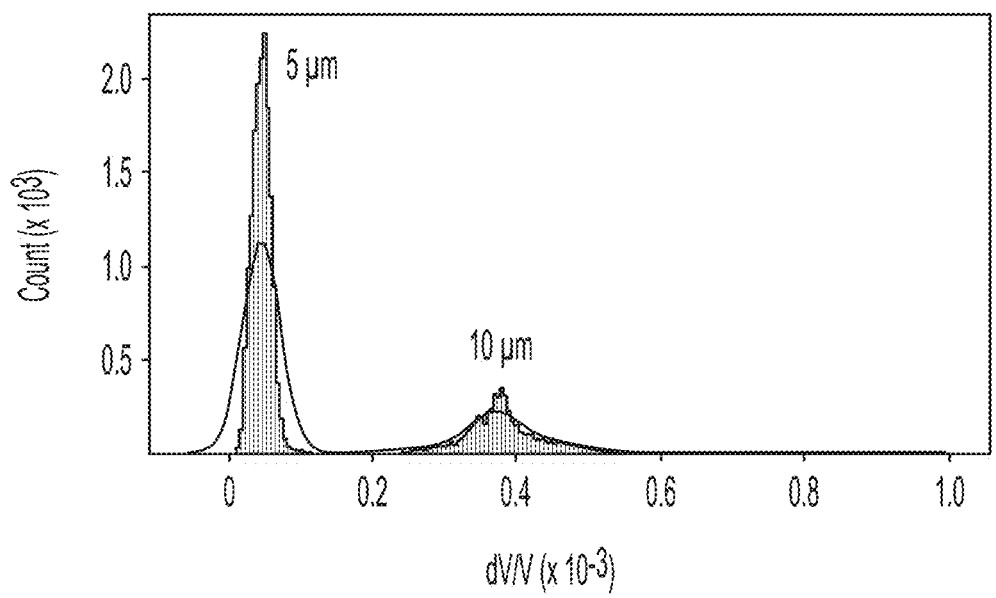
FIG. 21B shows a histogram of bead counts against measured voltage differential for 5 µm and 10 µm polystyrene beads flowing through a channel sensor. The results demonstrate that the polystyrene beads can be classified according to size based on the impedance attributable to the beads passing through a channel sensor.

A mixture of 5 µm and 10 µm polystyrene beads suspended in 1×PBS solution were pumped through a channel sensor at a constant flow rate of 2.5 µL/min. The channel sensor included a microchannel (length 1 mm, width and height of 20 µm), with three electrodes positioned along the length of the microchannel spaced 12.5 µm apart. An alternating current (0.5 Vpp, 100 kHz) passed between the electrodes as the beads flowed through the channel, and a voltage change was measured. The voltage differential signal was normalized (with baseline removed and signal demodulated from the alternating current so that the measured voltage was proportional to the impedance for a fixed alternating current signal). Exemplary normalized voltage signal over time is shown in FIG. 21A, with exemplary signals from a 5 µm bead and a 10 µm bead indicated. Smaller pulses correspond to the 5 µm beads, and larger pulses correspond to the 10 µm beads as they passed through the microchannel. A histogram of the voltage differential signals is shown in FIG. 21B, and demonstrates classification of two different bead sizes.

Example 4: Clustering of Different Cell Types

Figure 22A:
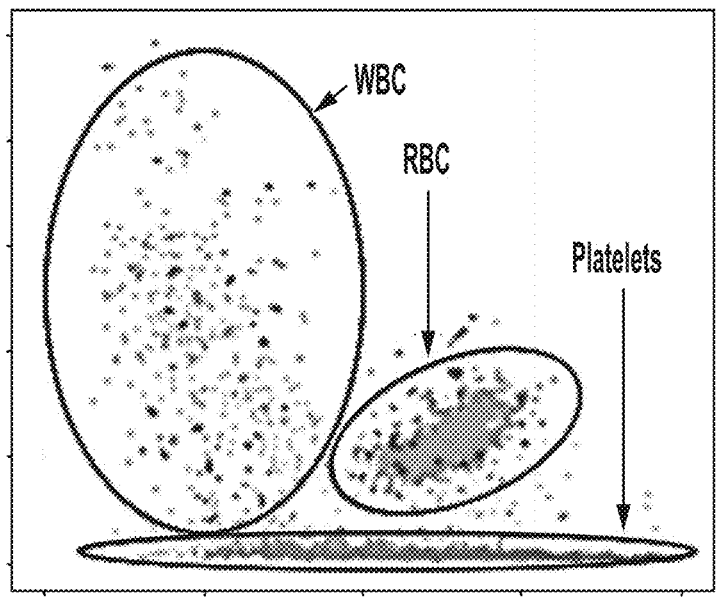
FIG. 22A shows clustering of white blood cells (WBC), red blood cells (RBC), and platelets by a machine learning model that sorts particles based on impedance signatures.
Figure 22B:
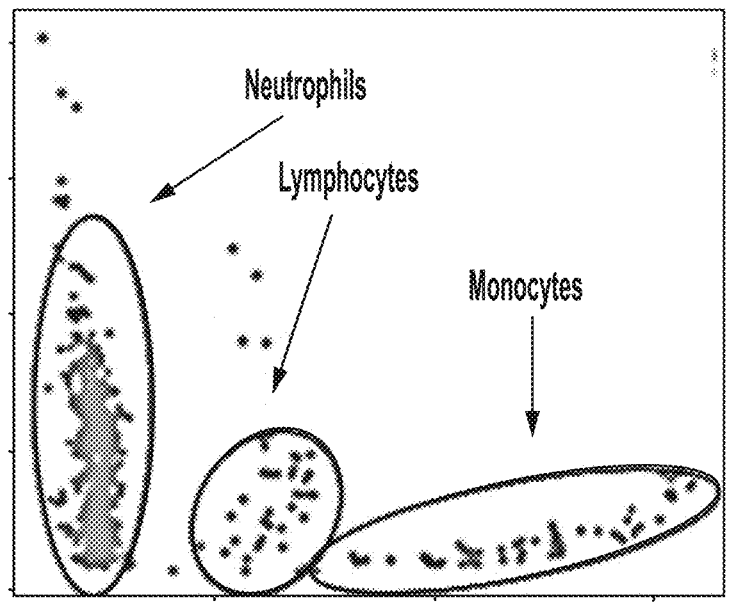
FIG. 22B shows clustering of neutrophils, lymphocytes, and monocytes by a machine learning model that sorts particles based on impedance signatures.
Figure 22C:
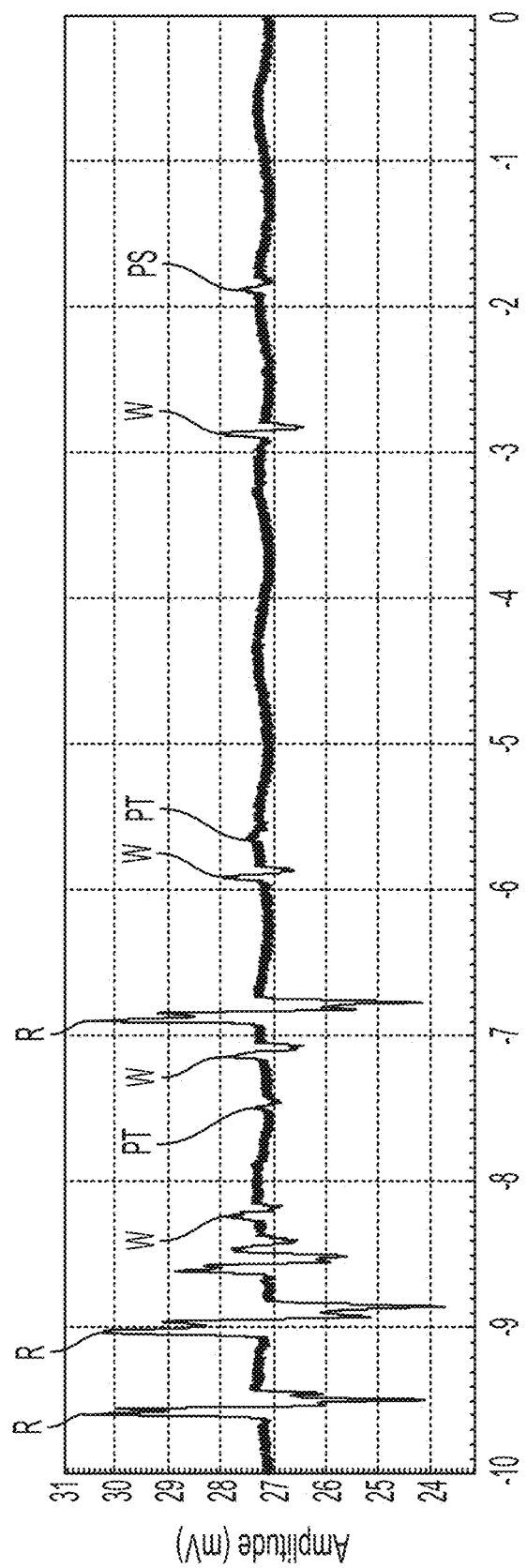
FIG. 22C shows a component voltage differential signal over time as diluted whole blood is passed through the sensor. Using a machine learning model, the particles that passed through the sensor were labeled as a red blood cells (R), white blood cells (W), platelets (P), or polystyrene beads (PS) based on the attributed impedance signature for the particles.

Impedance signatures were previously collected for all individual cells purified from whole blood taken from a healthy male as described in Example 2. This data formed the labelled data set that allowed identification of individual cell groups and clusters. Whole blood samples from healthy adults were diluted in 1×PBS to reduce the concentration of the cells and measured with the flow sensor. This unknown sample data were clustered across the multiple parameters into separate clusters. A labelled data set from previously collected data set was then used to further refine these clusters into categories or cell types. A combination of both unsupervised and supervised learning method (i.e. a semi-supervised learning technique) was used to refine the classification. The trained model clustered the impedance signatures into platelets, red blood cells (RBC), and white blood cells (WBC), as shown in FIG. 22A. In FIG. 22A, the classified cells are plotted and shown for 107 kHz. At the same time, the same trained model allows white blood cells to be further refined and clustered based on the impedance signatures to distinguish neutrophils, lymphocytes and monocytes, as shown in FIG. 22B. FIG. 22B, shows a plot of the cells types at 1.55 MHz An exemplary single signal is shown against time as the particles flow through the sensor in FIG. 22C, with each peak identified according to cell type (R indicates a red blood cell, W indicates a white blood cell, PT indicates a platelet, and PS indicates a 5 µm polystyrene bead, added to whole blood to demonstrate differentiation capability).

After clustering the impedance signatures, a count for each cell type could be obtained. The measured count is shown in Table 2, along with a reference range for a healthy adult male.

TABLE 2

| Cell Type | Measured Count | Reference Range |
|---|---|---|
| Platelets ($\times 10^6/\mu L$) | 0.18 | 0.13-0.32 |
| Red Blood cells ($\times 10^6/\mu L$) | 5.4 | 4.35-5.72 |
| White Blood Cells ($\times 10^3/\mu L$) | 5.3 | 3.4-9.65 |

Example 5: Measurement of Hemoglobin in a Red Blood Cell Lysate

Hemoglobin (Hb) content of a red blood cell lysate was measured using a metal oxide semiconductor capacitor (MOSCap) sensor configured for hemoglobin detection. A Hb-specific aptamer with a thiol group on the 5' end of the aptamer was bound to the electrode. The Hb-specific aptamer-modified electrode can be referred to as the "detection region" of the sensor. Whole blood was mixed with a red blood cell lysis reagent, and the lysate was positioned to the detection region. The lysate was allowed to incubate at the detection region, which allowed hemoglobin in the lysate to bind to the surface-bound Hb-specific aptamers. The detection region was then washed three times using a wash buffer to remove unbound portions of the lysate. A second Hb-specific aptamer conjugated to glucose oxidase (GOx) was moved to the detection region, and the GOx-conjugated aptamer bound the hemoglobin bound to the surface-bound aptamers. Unbound GOx-conjugated aptamers was then removed by washing the detection region. Glucose in buffer was introduced into the detection region, which the GOx uses to produce hydrogen peroxide and gluconic acid. The gluconic acid lowered the pH of the buffer, which was moved into an adjacent region of the sensor to the pH-sensitive MOScap sensor. Changes in the pH of the buffer were proportional to the concentration of hemoglobin in the sample. The hemoglobin concentration was determined based on a calibration data using known concentrations of purified hemoglobin.

What is claimed is:

1. A system, comprising
   (a) a cartridge configured to analyze a biological sample, the cartridge comprising:
      (i) a sensor comprising:
         a first channel segment;
         a second channel segment;
         a pore or a channel fluidly connecting the first channel segment and the second channel segment;
         an electrode pair configured to apply a multiplexed electrical current or voltage to the pore or channel; and
         an electrode pair configured to detect impedance at a plurality of frequencies within the pore or channel, wherein the electrode pair configured to apply the multiplexed electrical current and the electrode pair configured to detect the impedance are the same electrode pair or different electrode pairs; and
      (ii) a device interface electrically connected to the sensor; and
   (b) a device configured to interface with and operate the cartridge, comprising one or more processors and a non-transitory computer-readable storage medium storing one or more programs configured to be executed by the one or more processors, the one or more programs comprising instructions for determining a cell count based on a detected impedance, wherein the detected impedance comprises at least a first multivariate impedance pattern at a first frequency and a second multivariate impedance pattern at a second frequency.

2. The system of claim 1, wherein the electrode pair configured to apply the multiplexed electrical current and the electrode pair configured to detect the impedance are the same electrode pair.

3. The system of claim 1, wherein the first multivariate impedance pattern and the second multivariate impedance pattern each comprise a real component and an imaginary component of the impedance.

4. The system of claim 1, wherein the first multivariate impedance pattern and the second multivariate impedance pattern each comprise a magnitude component and phase component of the impedance.

5. The system of claim 1, wherein the first multivariate impedance pattern and the second multivariate impedance pattern comprises one or more of an impedance peak height, an impedance peak width, an impedance peak area, or an impedance peak half-width peak height.

6. The system of claim 1, wherein the system is configured to differentiate between different types of cells.

7. The system of claim 6, wherein the system is configured to differentiate between red blood cells, white blood cells, and platelets.

8. The system of claim 6, wherein the system is configured to differentiate between two or more of eosinophils, basophils, neutrophils, monocytes, and lymphocytes.

9. The system of claim 6, wherein the one or more programs comprises a machine learning model to differentiate between the different types of cells.

10. The system of claim 1, wherein the electrode pair configured to apply the multiplexed electrical current and the electrode pair configured to detect the impedance are different electrode pairs.

11. The system of claim 1, wherein the electrode pair is in direct contact with an inner portion of the channel.

12. The system of claim 1, wherein the electrode pair configured to detect impedance comprises a first electrode within the first channel segment, and a second electrode within the second channel segment.

13. The system of claim 1, wherein the sensor comprises the channel, and wherein the electrode pair configured to detect impedance is positioned within the channel.

14. The system of claim 1, wherein the electrode pair comprises a first electrode proximal to the first channel segment, and a second electrode proximal to the second channel segment.

15. The system of claim 1, wherein the electrode pair comprises a first electrode on an upper surface of the channel, and a second electrode on a lower surface of the channel, and wherein the first electrode is positioned above the second electrode.

16. The system of claim 1, wherein the sensor further comprises an electrode pair configured to detect liquid flow within the sensor.

17. The system of claim 1, wherein the sensor comprises one or more isolation electrodes.

18. The system of claim 1, wherein the multiplexed electrical current comprises a plurality of alternating current components at different frequencies.

19. The system of claim 1, wherein the multiplexed electrical current comprises a (1) a direct current component or a low-frequency alternating current, and (2) a plurality of alternating current components at different frequencies.

20. The system of claim 19, wherein the plurality of alternating current components comprises at least three alternating current components.

21. The system of claim 19, wherein the plurality of alternating current components comprises a first alternating current at about 10 kHz to about 100 kHz, a second alternating current at about 100 kHz to about 700 kHz, a third alternating at about 700 kHz to about 5 MHz and a fourth alternating current greater than about 5 MHz.

22. The system of claim 19, wherein the plurality of alternating current components comprises at least five alternating current components.

23. The system of claim 22, wherein the plurality of alternating current components comprises a first alternating current at about 50 kHz to about 250 kHz, a second alternating current at about 250 kHz to about 700 kHz, a third alternating at about 700 kHz to about 5 MHz, a fourth alternating current at about 5 MHz to about 20 MHz, and a fifth alternating current at about 20 MHz to about 150 MHz.

24. The system of claim 19, wherein the plurality of alternating current components comprises at least two different alternating current components comprising one or more alternating current below 1 MHz and one or more alternating current above 1 MHz.

25. The system of claim 1, wherein the electrode pair configured to detect impedance is configured to detect impedance at a sampling rate of about 100 kHz or more.

26. The system of claim 1, wherein the system is configured to distinguish normal cell populations from abnormal cell populations.

27. A system, comprising
(a) a cartridge configured to analyze a biological sample, the cartridge comprising:
  (i) a sensor comprising:
    a first channel segment;
    a second channel segment;
    a pore or a channel fluidly connecting the first channel segment and the second channel segment;
    an electrode pair configured to apply a multiplexed electrical current or voltage to the pore or channel; and
    an electrode pair configured to detect impedance at a plurality of frequencies within the pore or channel, wherein the electrode pair configured to apply the multiplexed electrical current and the electrode pair configured to detect the impedance are the same electrode pair or different electrode pairs; and
  (ii) a device interface electrically connected to the sensor; and
(b) a device configured to interface with and operate the cartridge, comprising one or more processors and a non-transitory computer-readable storage medium storing one or more programs configured to be executed by the one or more processors, the one or more programs comprising instructions for differentiating between different types of cells based on the detected impedance using a machine learning model, wherein the detected impedance comprises at least a magnitude component and a phase component of impedance at a first frequency and a magnitude component and a phase component of impedance at a second frequency.

28. The system of claim 27, wherein the system is configured to differentiate between red blood cells, white blood cells, and platelets.

29. The system of claim 27, wherein the system is configured to differentiate between eosinophils, basophils, neutrophils, monocytes, and lymphocytes.

30. The system of claim 27, wherein the system is configured to distinguish normal cell populations from abnormal cell populations.

* * * * *